US007612153B2

(12) United States Patent
Breitenkamp et al.

(10) Patent No.: US 7,612,153 B2
(45) Date of Patent: Nov. 3, 2009

(54) HETEROBIFUNCTIONAL POLY(ETHYLENE GLYCOL) AND USES THEREOF

(75) Inventors: Kurt Breitenkamp, Northampton, MA (US); Kevin Sill, Tampa, FL (US); Habib Skaff, Tampa, FL (US)

(73) Assignee: Intezyne Technologies, Inc., Tampa, FL (US)

( * ) Notice: Subject to any disclaimer, the term of this patent is extended or adjusted under 35 U.S.C. 154(b) by 321 days.

(21) Appl. No.: 11/256,735

(22) Filed: Oct. 24, 2005

(65) Prior Publication Data
US 2006/0142506 A1    Jun. 29, 2006

Related U.S. Application Data

(60) Provisional application No. 60/621,866, filed on Oct. 25, 2004.

(51) Int. Cl.
*C08F 283/10* (2006.01)
*C08G 59/14* (2006.01)
*C08L 63/00* (2006.01)

(52) U.S. Cl. .................. 525/523; 525/482; 549/352; 549/223; 549/482; 548/518; 548/473; 546/255; 562/498; 556/449

(58) Field of Classification Search ............... 525/482, 525/523; 549/352, 223, 482; 548/518, 473; 546/255; 562/498; 556/449
See application file for complete search history.

(56) References Cited

U.S. PATENT DOCUMENTS

| | | | | |
|---|---|---|---|---|
| 5,455,027 | A | 10/1995 | Zalipsky et al. | 424/78.17 |
| 5,686,110 | A | 11/1997 | Greenwald et al. | 424/486 |
| 5,756,593 | A | 5/1998 | Martinez et al. | 525/403 |
| 5,808,096 | A | 9/1998 | Zalipsky | 548/520 |
| 5,824,701 | A | 10/1998 | Greenwald et al. | 514/449 |
| 6,127,355 | A | 10/2000 | Greenwald et al. | 514/183 |
| 6,180,095 | B1 | 1/2001 | Greenwald et al. | 424/85.1 |
| 6,251,382 | B1 | 6/2001 | Greenwald et al. | 424/78.17 |
| 6,448,369 | B1 | 9/2002 | Bentley et al. | 528/425 |
| 6,608,076 | B1 | 8/2003 | Greenwald et al. | 514/285 |
| 6,649,778 | B1 | 11/2003 | Zhao et al. | 549/510 |
| 6,703,446 | B2 | 3/2004 | Schwindeman et al. | 525/272 |
| 6,720,391 | B2 | 4/2004 | Schwindeman et al. | 525/355 |
| 6,737,505 | B2 | 5/2004 | Bentley et al. | 528/425 |
| 6,777,387 | B2 | 8/2004 | Greenwald et al. | 514/8 |
| 6,894,025 | B2 | 5/2005 | Harris | 514/2 |
| 6,899,867 | B2 | 5/2005 | Bentley et al. | 424/78.02 |
| 7,026,440 | B2 | 4/2006 | Bentley et al. | 528/407 |
| 7,033,583 | B2 | 4/2006 | Choe et al. | 424/78.1 |
| 2004/0116649 | A1 | 6/2004 | Kozlowski | |
| 2005/0031576 | A1 | 2/2005 | McManus et al. | |
| 2005/0036978 | A1 | 2/2005 | Kozlowski | |
| 2005/0054816 | A1 | 3/2005 | McManus et al. | |
| 2005/0119193 | A1 | 6/2005 | Motoyama | |
| 2005/0214250 | A1 | 9/2005 | Harris et al. | |
| 2008/0280998 | A1 | 11/2008 | Bonora et al. | |

FOREIGN PATENT DOCUMENTS

WO    WO 2005/033181    4/2005

OTHER PUBLICATIONS

Yoon et al; The photochemistry—biradical intermediates; Amercian Chemical society (2004), 126(4), 1110-1124; Chem Abstract 140: 217172.*
Kikuchi et al; Preparation of pyrimidine—accelerators; Nishhin Flour Milling Co., Ltd., Japan; 1996, Chem Abstract 124: 232479.*
Vidaluc et al; Flexible—evaluation; Amercian Chemical society; (1995), 38(15), 2969-73; Chem Abstract 123: 111638.*
Akiyama et al; N-hydroxy amides—oligo(ethyleneoxy)arms; Physical organic Chemistry (1972-1999) (1989), (9), 1213-18, Chem Abstract 112:178261.*
Clinton et al; Sulfur containing amines; Journal of the Amercian Chemical society; (1948), 70, 950-5, VChem Abstract 42: 27477.*
Akiyama, et al., "Selective Synthesis Of Heterobifunctional Poly(ethylene glycol) Derivatives Containing Both Mercapto and Acetal Terminals.", *Bioconjugate Chem.* 11: 947-950, 2000.
Akiyama, et al., "Synthesis Of Heterotelechelic Poly(ethylene glycol) Derivatives Having α-Benzaldehyde And ω-Pyridyl Disulfide Groups By Ring Opening Polymerization Of Ethylene Oxide Using 4-(Diethoxymethyl)benzyl Alkoxide As A Novel Initiator.", *Bioconjugate Chem.* 15: 424-427, 2004.
Akiyama, et al., "Synthesis Of Poly(ethylene glycol)-*Block*-Poly(ethylenimine) Possessing An Acetal Group At The PEG End.", *Macromolecules* 33: 5841-5845, 2000.
Bettinger, et al., "Convenient Polymer-Supported Synthetic Route To Heterobifunctional Polyethylene Glycols.", *Bioconjugate Chem.* 9: 842-846, 1998.
Cammas, et al., "Heterobifunctional Poly(ethylene Oxide): Synthesis Of α-Hydroxy-ω-Amino PEOs With The Same Molecular Weights.", *Bioconjugate Chem.* 6: 226-230, 1995.
Dombi, et al., "Oligonucleotide Arrays From Aldehyde-Bearing Glass With Coated Background.", *Synthesis* 6: 816-824, 2002.
Glaied, et al., "Oxazoline-Terminated Macromonomers By The Alkylation Of 2-Methyl-2-Oxazoline.", *Journal of Polymer Science: Part A: Polymer Chem.* 43: 2440-2447, 2005.
Heroguez, et al., "Synthesis Of α-Norbornenylpoly(ethylene oxide) Macromonomers And Their Ring-Opening Metathesis Polymerization.", *Macromolecules* 29(13): 4459-4464, 1996.

(Continued)

*Primary Examiner*—Duc Truong
(74) *Attorney, Agent, or Firm*—Choate Hall & Stewart LLP; Andrea L. C. Robidoux

(57) ABSTRACT

The present invention provides bifunctional polymers, methods of preparing the same, and intermediates thereto. These compounds are useful in a variety of applications including the PEGylation of biologically active molecules. The invention also provides methods of using said compounds and compositions thereof.

23 Claims, No Drawings

OTHER PUBLICATIONS

Huang, et al., "The Kinetics Of The Attachment Of Polymer Chains To Reactive Latex Particles And The Resulting Latex Stabilization," *J. of Polymer Sci.*, 23: 795-799, 1985.

Kazanskii, et al., "Strictly Monofunctional Methyl Ethers Of Poly(ethylene glycol) And The Related Methacrylate Macromonomers.", *Polymer Science Ser. A.* 42(6): 585-595, 2000.

Kim, et al., "Heterobifunctional Poly(ethylene oxide)," *Polymer Bulletin*, 33: 1-6, 1994.

Li and Kao, "Synthesis Of Polyethylene Glycol (PEG) Derivatives And PEGylated-Peptide Biopolymer Conjugates.", *Biomacromolecules* 4: 1055-1067, 2003.

Link, et al., "Presentation And Detection Of Azide Functionality In Bacterial Cell Surface Proteins.", *J. Am. Chem. Soc.* XXXX(XXX): A-E.

Mongondry, et al., "Mild Synthesis Of Amino-Poly(ethylene glycol)s. Application To Steric Stabilization Of Clays.", *Macromol. Rapid Commun.* 24: 681-685, 2003.

Nagasaki, et al., "Primary Amino-Terminal Heterobifunctional Poly(ethylene Oxide). Facile Synthesis of Poly(ethylene Oxide) With A Primary Amino Group At One End And A Hydroxyl Group At The Other End.", *Bioconjugate Chem.* 6: 702-704, 1995.

Nagasaki, et al., "Synthesis Of Heterotelechelic Poly(ethylene glycol) Macromonomers. Preparation Of Poly(ethylene glycol) Possessing A Methacryloyl Group At One End And A Formyl Group At The Other End.", *Macromolecules* 30: 6489-6493, 1997.

Nakamura, et al., "Synthesis of Heterobifunctional Poly(ethylene glycol) With A Reducing Monosaccharide Residue At One End.", *Bioconjugate Chem.* 9: 300-303, 1998.

Parrish, et al., "Bio-Tailored Amphiphilic Graft Copolymers.", *Polymer Preprints* 46(1): 126, 2005.

Parrish, et al., "PEG- And Peptide-Grafted Aliphatic Polyesters By Click Chemistry.", *J. Am. Chem. Soc.* 127(20): 7404-7410, 2005.

Parrish, et al., "PEG- And Peptide-Tailored Aliphatic Polyesters Synthesized By 'Click' Cycloaddition Chemistry.", *Polymer Preprints* 46(1): 292-293, 2005.

Reed and Janda, "A One-Step Synthesis Of Monoprotected Polyethylene Glycol Ethers," *J. Org. Chem.*, 65: 5843-5845, 2000.

Ryoo, et al., "Efficient Methods Of Converting Hydroxyl Groups Into Amino Groups In Poly(ethylene glycol)-Grafted Polystyrene Resin.", *Journal of Combinatorial Chem.* 4(3): 187-190, 2002.

Senyo, et al., "Syntheses of Poly(ethylene oxide) Macromonomers Carrying Tertiary Amine And Quaternary Ammonium End Groups.", *Polymer Journal* 35(6): 513-518, 2003.

Shen, et al., "One-Step Synthesis of $\alpha$-p-Vinylphenylalkyl-$\omega$-Hydroxy Poly(ethylene Oxide) Macromonomers By Anionic Polymerization Initiated From p-Vinylphenylalkanols.", *Polymer* 44: 3221-3228, 2003.

Zhang, et al., "Synthesis Of Heterobifunctional Poly(ethylene glycol) With A Primary Amino Group At One End And A Carboxylate Group At The Other End.", *Reactive & Functional Polymers* 56: 17-25, 2003.

* cited by examiner

HETEROBIFUNCTIONAL POLY(ETHYLENE GLYCOL) AND USES THEREOF

CROSS-REFERENCE TO RELATED APPLICATIONS

This application claims priority to U.S. provisional application Ser. No. 60/621,866, filed Oct. 25, 2004, the entirety of which is hereby incorporated herein by reference.

FIELD OF THE INVENTION

The present invention relates to the field of polymer chemistry and more particularly to functionalized polymers, uses thereof, and intermediates thereto.

BACKGROUND OF THE INVENTION

Poly(ethylene glycol), also known as PEG, is useful in a variety of technological areas and is generally known by the formula HO—$CH_2CH_2$O—($CH_2CH_2$O)$_n$—$CH_2CH_2$—OH, wherein n typically ranges from about 3 to about 4000. In particular, there is great interest in utilizing PEG, and derivatives thereof, in the pharmaceutical and biomedical fields. This interest stems from the fact that PEG is nontoxic, biocompatible, non-immunogenic, soluble in water and other solvents, and is amenable to a variety of therapeutic applications including pharmaceutical formulations and drug delivery systems, among others.

One such area of interest relates to "PEGylation" which refers to the modification of other molecules, especially biomolecules, using PEG and derivatives thereof. PEGylation is often utilized in order to impart the desirable characteristics of PEG to a particular molecule. Such molecules have included proteins, dyes, peptides, hydrogels, and drugs, to name but a few. In the case of drugs, the formation of drug-polymer conjugates is also of interest. In addition, PEGylation has been utilized to attach PEG to other groups such as surfaces and cells.

The two terminal hydroxyl groups of PEG are readily available for chemical modification (e.g., for coupling to a protein or drug). However, this process requires the further functionalization of the PEG terminus in order to affect coupling to another molecule. Furthermore, because PEG contains two terminal hydroxyl groups it is often necessary to protect one of those hydroxyl groups in order to functionalize the other hydroxyl group. Thus, the current process of PEGylation typically requires multiple steps and results are often unpredictable.

Accordingly, it would be advantageous to provide heterobifunctionalized PEG's which are useful for PEGylation and are readily obtained directly from the polymerization reaction.

DETAILED DESCRIPTION OF CERTAIN EMBODIMENTS OF THE INVENTION

1. General Description of the Invention:

The present invention provides a method for preparing a compound of formula I:

$$R^1\diagdown\diagup O\diagdown(O\diagdown)_n\diagdown R^2 \qquad \text{I}$$

wherein:
n is 10-2500;
$R^1$ is —$X(CH_2CH_2Y)_m(CH_2)_nR^3$, wherein:
   X is —O—, —S—, —C≡C—, or —$CH_2$—;
   each Y is independently —O— or —S—;
   m is 0-10;
   n is 0-10; and
   $R^3$ is —$N_3$, —CN, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
$R^2$ is halogen, $N_3$, CN, a mono-protected amine, a di-protected amine, a protected hydroxyl, a protected aldehyde, a protected thiol, —$NHR^4$, —$N(R^4)_2$, —$SR^4$, —$O(CH_2CH_2O)_q(CH_2)_rR^5$, —$OC(O)R^4$, or —$OS(O)_2R^4$;
q and r are each independently 0-4;
each $R^4$ is independently an optionally substituted group selected from aliphatic, a 5-8-membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or:
   two $R^4$ on the same nitrogen atom are taken together with said nitrogen atom to form an optionally substituted 4-7-membered saturated, partially unsaturated, or aryl ring having 1-4 heteroatoms independently selected from nitrogen, oxygen, or sulfur; and
$R^5$ is hydrogen, halogen, $N_3$, CN, a mono-protected amine, a di-protected amine, a protected aldehyde, a protected hydroxyl, a protected carboxylic acid, a protected thiol, or an optionally substituted group selected from aliphatic, a 5-8-membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, from a compound of formula II:

$$R^1\diagdown\diagup O\diagdown(O\diagdown)_n\diagdown O^{\ominus}\!\!\oplus OM \qquad \text{II}$$

wherein:
M is the cation of a suitable metal;
n is 10-2500;
$R^1$ is —$X(CH_2CH_2Y)_m(CH_2)_nR^3$, wherein:
   X is —O—, —S—, —C≡C—, or —$CH_2$—;
   each Y is independently —O— or —S—;
   m is 0-10;
   n is 0-10; and
   $R^3$ is —$N_3$, —CN, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

comprising the step of terminating the living polymer chain-end of the compound of formula II with a suitable polymerization terminator to afford a compound of formula I.

Another aspect of the present invention provides a method for preparing a compound of formula I:

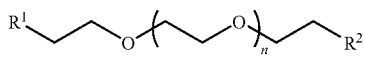

I wherein:
n is 10-2500;
$R^1$ is —$X(CH_2CH_2Y)_m(CH_2)_nR^3$, wherein:
  X is —O—, —S—, —C≡C—, or —CH$_2$—;
  each Y is independently —O— or —S—;
  m is 0-10;
  n is 0-10; and
  $R^3$ is —$N_3$, —CN, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
$R^2$ is halogen, $N_3$, CN, a mono-protected amine, a di-protected amine, a protected hydroxyl, a protected aldehyde, a protected thiol, —$NHR^4$, —$N(R^4)_2$, —$SR^4$, —$O(CH_2CH_2O)_q(CH_2)_rR^5$, —$OC(O)R^4$, or —$OS(O)_2R^4$;
q and r are each independently 0-4;
each $R^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or:
  two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur; and
$R^5$ is hydrogen, halogen, CN, a mono-protected amine, a di-protected amine, a protected aldehyde, a protected hydroxyl, a protected carboxylic acid, a protected thiol, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, from a compound of formula II:

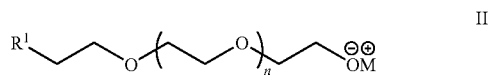

II wherein:
M is the cation of a suitable metal;
n is 10-2500;
$R^1$ is —$X(CH_2CH_2Y)_m(CH_2)_nR^3$, wherein:
  X is —O—, —S—, —C≡C—, or —CH$_2$—;
  each Y is independently —O— or —S—;
  m is 0-10;
  n is 0-10; and
  $R^3$ is —$N_3$, —CN, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

comprising the steps of:
(1) providing a polymerization initiator of formula $HX(CH_2CH_2Y)_m(CH_2)_nR^3$, wherein:
  X is —O—, —S—, —C≡C—, or —CH$_2$—;
  each Y is independently —O— or —S—;
  m is 0-10;
  n is 0-10; and
  $R^3$ is —$N_3$, —CN, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
(2) polymerizing ethylene oxide onto said polymerization initiator to provide a compound of formula II; and
(3) terminating the living polymer chain-end of the compound of formula II with a suitable polymerization terminator to afford a compound of formula I.

2. Definitions:

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the phrase "living polymer chain-end" refers to the terminus resulting from a polymerization reaction which maintains the ability to react further with additional monomer or with a polymerization terminator.

As used herein, the term "termination" refers to attaching a terminal group to a living polymer chain-end by reacting the living polymer chain-end with a polymerization terminator. Alternatively, the term "termination" may refer to the attachment of a terminal group to a hydroxyl end, or derivative thereof, of the polymer chain.

As used herein, the term "polymerization terminator" is used interchangeably with the term "polymerization terminating agent" and refers to compounds that react with a living polymer chain-end to afford a polymer with a terminal group. Alternatively, the term "polymerization terminator" may refer to a compound that may react with a hydroxyl end, or derivative thereof, of the polymer chain to afford a polymer with a terminal group.

As used herein, the term "polymerization initiator" refers to a compound, or anion thereof, which reacts with ethylene oxide in a manner which results in polymerization thereof. In certain embodiments, the polymerization initiator is the anion of a functional group which initiates the polymerization of ethylene oxide.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R$^+$)— as in N-substituted pyrrolidinyl.

The term "unsaturated", as used herein, means that a moiety has one or more units of unsaturation.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•$$_2$, —NO$_2$, —SiR$^•$$_3$, —OSiR$^•$$_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A suitable tetravalent substituent that is bound to vicinal substitutable methylene carbons of an "optionally substituted" group is the dicobalt hexacarbonyl cluster represented by

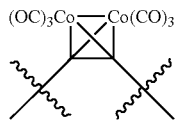

when depicted with the methylenes which bear it.

Suitable substituents on the aliphatic group of R* include halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†$$_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted C$_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

A "crown ether moiety" is the radical of a crown ether. A crown ether is a monocyclic polyether comprised of repeating units of —$CH_2CH_2O$—. Examples of crown ethers include 12-crown-4, 15-crown-5, and 18-crown-6.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

As used herein, the term "detectable moiety" is used interchangeably with the term "label" and relates to any moiety capable of being detected (e.g., primary labels and secondary labels). A "detectable moiety" or "label" is the radical of a detectable compound.

"Primary" labels include radioisotope-containing moieties (e.g., moieties that contain $^{32}$P, $^{33}$P, $^{35}$S, or $^{14}$C), mass-tags, and fluorescent labels, and are signal-generating reporter groups which can be detected without further modifications.

Other primary labels include those useful for positron emission tomography including molecules containing radioisotopes (e.g. $^{18}$F) or ligands with bound radioactive metals (e.g. $^{62}$Cu). In other embodiments, primary labels are contrast agents for magnetic resonance imaging such as gadolinium, gadolinium chelates, or iron oxide (e.g $Fe_3O_4$ and $Fe_2O_3$) particles. Similarly, semiconducting nanoparticles (e.g. cadmium selenide, cadmium sulfide, cadmium telluride) are useful as fluorescent labels. Other metal nanoparticles (e.g colloidal gold) also serve as primary labels.

"Secondary" labels include moieties such as biotin, or protein antigens, that require the presence of a second compound to produce a detectable signal. For example, in the case of a biotin label, the second compound may include streptavidin-enzyme conjugates. In the case of an antigen label, the second compound may include an antibody-enzyme conjugate. Additionally, certain fluorescent groups can act as secondary labels by transferring energy to another compound or group in a process of nonradiative fluorescent resonance energy transfer (FRET), causing the second compound or group to then generate the signal that is detected.

Unless otherwise indicated, radioisotope-containing moieties are optionally substituted hydrocarbon groups that contain at least one radioisotope. Unless otherwise indicated, radioisotope-containing moieties contain from 1-40 carbon atoms and one radioisotope. In certain embodiments, radioisotope-containing moieties contain from 1-20 carbon atoms and one radioisotope.

The term "mass-tag" as used herein refers to any compound that is capable of being uniquely detected by virtue of its mass using mass spectrometry (MS) detection techniques. Examples of mass-tags include electrophore release tags such as N-[3-[4'-[(p-methoxytetrafluorobenzyl)oxy]phenyl]-3-methylglyceronyl]-isonipecotic acid, 4'-[2,3,5,6-tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "fluorescent label", "fluorescent group", "fluorescent compound", "fluorescent dye", and "fluorophore", as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, anthracene, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), carbazole, Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "substrate", as used herein refers to any material or macromolecular complex to which a functionalized end-group of a PEG can be attached. Examples of commonly used substrates include, but are not limited to, glass surfaces, silica surfaces, plastic surfaces, metal surfaces, surfaces containing a metallic or chemical coating, membranes (e.g., nylon, polysulfone, silica), micro-beads (e.g., latex, polystyrene, or other polymer), porous polymer matrices (e.g., polyacrylamide gel, polysaccharide, polymethacrylate), macromolecular complexes (e.g., protein, polysaccharide).

3. Description of Exemplary Embodiments:

In certain embodiments, the present invention provides a method for preparing a compound of formula I, as described above, wherein the $R^1$ and $R^2$ groups of formula I are different from each other.

In other embodiments, the present invention provides a method for preparing a compound of formula I, as described above, wherein only one of the $R^3$ moiety of the $R^1$ group, or the $R^2$ group, of formula I is a protected hydroxyl.

In yet other embodiments, the present invention provides a method for preparing a compound of formula I, as described above, wherein neither the $R^3$ moiety of the $R^1$ group, nor the $R^2$ group, of formula I is a suitably protected hydroxyl group.

In yet other embodiments, the present invention provides a method for preparing a compound of formula I, as described above, wherein neither the $R^3$ moiety of the $R^1$ group, nor the $R^2$ group, of formula I is methyl.

According to another embodiment, the present invention provides a method for preparing compounds of formula I, as described above, wherein said compounds have a polydispersity index ("PDI") of about 1.0 to about 1.2. According to another embodiment, the present invention provides a method for preparing compounds of formula I, as described above, wherein said compounds have a polydispersity index ("PDI") of about 1.03 to about 1.15. According to yet another embodiment, the present invention provides a method for preparing compounds of formula I, as described above, wherein said compounds have a polydispersity index ("PDI") of about 1.10 to about 1.12.

In certain embodiments, n is about 225. In other embodiments, n is about 200 to about 300. In still other embodiments, n is about 200 to about 250. In still other embodiments, n is about 100 to about 150. In still other embodiments, n is about 400 to about 500.

As described generally above, $R^1$ is —X(CH$_2$CH$_2$Y)$_m$(CH$_2$)$_n$R$^3$, wherein X is —O—, —S—, —C≡C—, or —CH$_2$—; each Y is independently —O— or —S—; m is 0-10; n is 0-10; and $R^3$ is —N$_3$, —CN, a mono-protected amine, a di-protected amine, a protected aldehyde, a protected hydroxyl, a protected carboxylic acid, a protected thiol, a 9-30-membered crown ether, an optionally substituted aliphatic group, an optionally substituted 5-8-membered saturated, partially unsaturated, or aryl ring having 0-4 heteroatoms independently selected from nitrogen, oxygen, or sulfur, an optionally substituted 8-10-membered saturated, partially unsaturated, or aryl bicyclic ring having 0-5 heteroatoms independently selected from nitrogen, oxygen, or sulfur, or a detectable moiety.

In certain embodiments, the $R^3$ moiety of the $R^1$ group of either of formula I or II is —N$_3$. In certain embodiments, $R^1$ is other than 2-azidoethoxy.

In other embodiments, the $R^3$ moiety of the $R^1$ group of either of formula I or II is —CN.

In certain embodiments, the $R^3$ moiety of the $R^1$ group of either of formula I or II is an optionally substituted aliphatic group. Examples include t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said $R^3$ moiety is an optionally substituted alkyl group. In other embodiments, said $R^3$ moiety is an optionally substituted alkynyl or alkenyl group. When said $R^3$ moiety is a substituted aliphatic group, suitable substituents on $R^3$ include CN, N$_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the $R^1$ group is 2-(N-methyl-N-(ethynylcarbonyl)amino)ethoxy, 4-ethynylbenzyloxy, or 2-(4-ethynylphenoxy)ethoxy. In certain embodiments, $R^1$ is other than propargyloxy, 1-(but-3-yn)oxy, 3-t-butyldimethylsilylpropargyloxy, 3-triisopropylsilylpropargyloxy, 1-(6-t-butyldimethylsilylhex-5-yn)oxy, or 1-(6-triisopropylsilylhex-5-yn)oxy.

In certain embodiments, the $R^3$ moiety of the $R^1$ group of either of formula I or II is an optionally substituted aryl group. Examples include optionally substituted phenyl and optionally substituted pyridyl. When said $R^3$ moiety is a substituted aryl group, suitable substituents on $R^3$ include CN, N$_3$, NO$_2$, —CH$_3$, —CH$_2$N$_3$, —CH=CH$_2$, —C≡CH, Br, I, F, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl. In certain embodiments, $R^1$ is other than 4-azidomethylbenzyloxy.

In other embodiments, the $R^3$ moiety of the $R^1$ group of either of formula I or II is a protected hydroxyl group. In certain embodiments the protected hydroxyl of the $R^3$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ether, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the $R^3$ moiety of the $R^1$ group of either of formula I or II is a mono-protected or di-protected amino group. In certain embodiments $R^3$ is a mono-protected amine. In certain embodiments $R^3$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^3$ is a di-protected amine. Exemplary di-protected amines include dibenzylamine, di-allylamine, phthalimide, maleimide, succinimide, pyrrole, 2,2,5,5-tetramethyl-[1,2,5]azadisilolidine, and azide. In certain embodiments, the $R^3$ moiety is phthalimido. In other embodiments, the $R^3$ moiety is mono- or di-benzylamino or mono- or di-allylamino. In certain embodiments, the $R^1$ group is 2-dibenzylaminoethoxy. In still other embodiments, the $R^1$ group is other than 2-t-butoxycarbonylamino-ethoxy.

In other embodiments, the $R^3$ moiety of the $R^1$ group of either of formula I or II is a protected aldehyde group. In certain embodiments the protected aldehydo moiety of $R^3$ is an acyclic acetal, a cyclic acetal, a hydrazone, or an imine. Exemplary $R^3$ groups include dimethyl acetal, diethyl acetal, diisopropyl acetal, dibenzyl acetal, bis(2-nitrobenzyl) acetal, 1,3-dioxane, 1,3-dioxolane, and semicarbazone. In certain embodiments, $R^3$ is an acyclic acetal or a cyclic acetal. In other embodiments, $R^3$ is a dibenzyl acetal.

In yet other embodiments, the $R^3$ moiety of the $R^1$ group of either of formula I or II is a protected carboxylic acid group. In certain embodiments, the protected carboxylic acid moiety of $R^3$ is an optionally substituted ester selected from $C_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of $R^3$ is an oxazoline or an ortho ester. Examples of such protected carboxylic acid moieties include oxazolin-2-yl and 2-methoxy-[1,3]dioxin-2-yl. In certain embodiments, the $R^1$ group is oxazolin-2-ylmethoxy or 2-oxazolin-2-yl-1-propoxy. In certain embodiments, $R^1$ is other than 2-methoxy-[1,3]dioxin-2-ylmethoxy.

According to another embodiments, the $R^3$ moiety of the $R^1$ group of either of formula I or II is a protected thiol group. In certain embodiments, the protected thiol of $R^3$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, $R^3$ is an optionally substituted thioether selected from alkyl, benzyl, or triphenylmethyl, or trichloroethoxycarbonyl thioester. In certain embodmients, $R^3$ is —S—S-pyridin-2-yl, —S—SBn, —S—SCH$_3$, or —S—S(p-ethynylbenzyl). In other embodmients, $R^3$ is —S—S-pyridin-2-yl. In still other embodiments, the $R^1$ group is 2-triphenylmethylsulfanyl-ethoxy.

In certain embodiments, the $R^3$ moiety of the $R^1$ group of either of formula I or II is a crown ether. Examples of such crown ethers include 12-crown-4, 15-crown-5, and 18-crown-6.

In still other embodiments, the $R^3$ moiety of the $R^1$ group of either of formula I or II is a detectable moiety. According to one aspect of the invention, the $R^3$ moiety of the $R^1$ group of either of formula I or II is a fluorescent moiety. Such fluorescent moieties are well known in the art and include coumarins, quinolones, benzoisoquinolones, hostasol, and Rhodamine dyes, to name but a few. Exemplary fluorescent moieties of the $R^3$ group of $R^1$ include anthracen-9-yl, pyren-4-yl, 9-H-carbazol-9-yl, the carboxylate of rhodamine B, and the carboxylate of coumarin 343.

In certain embodiments, the $R^3$ moiety of the $R^1$ group of either of formula I or II is a group suitable for Click chemistry. Click reactions tend to involve high-energy ("spring-loaded") reagents with well-defined reaction coordinates, that give rise to selective bond-forming events of wide scope. Examples include nucleophilic trapping of strained-ring electrophiles (epoxide, aziridines, aziridinium ions, episulfonium ions), certain carbonyl reactivity (e.g., the reaction between aldehydes and hydrazines or hydroxylamines), and several cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

Compounds of formula I or II having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of formula I to a macromolecule via Click chemistry. Yet another embodiment of the present invention provides a macromolecule conjugated to a compound of formula I via the $R^1$ group.

After conjugation to a biomolecule, drug, cell, substrate, or the like, the other end-group functionality, corresponding to the $R^2$ moiety of formula I, can be used to attach targeting groups for cell-specific delivery including, but not limited to, detectable moieties, such as fluorescent dyes, covalent attachment to surfaces, and incorporation into hydrogels.

According to one embodiment, the $R^3$ moiety of the $R^1$ group of either of formula I or II is an azide-containing group. According to another embodiment, the $R^3$ moiety of the $R^1$ group of either of formula I or II is an alkyne-containing group. In certain embodiments, the $R^3$ moiety of the $R^1$ group of either of formula I or II has a terminal alkyne moiety. In other embodiments, the $R^3$ moiety of the $R^1$ group of either of formula I or II is an alkyne moiety having an electron withdrawing group. Accordingly, in such embodiments, the $R^3$ moiety of the $R^1$ group of either of formula I or II is

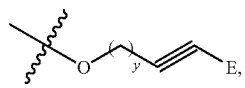

wherein E is an electron withdrawing group and y is 0-6. Such electron withdrawing groups are known to one of ordinary skill in the art. In certain embodiments, E is an ester. In other embodiments, the $R^3$ moiety of the $R^1$ group of either of formula I or II is

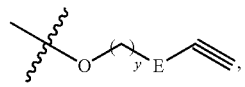

wherein E is an electron withdrawing group, such as a —C(O)O— group and y is 0-6.

In certain embodiments, the methods of the present invention are performed in a suitable medium. According to one embodiment, a suitable medium for the preparation of compounds of formula I includes a polar aprotic solvent or a mixture thereof. Examples of polar aprotic solvents include, but are not limited to, DMF, DMSO, THF, hexamethylphosphoramide, glyme, diglyme, MTBE, N-methylpyrrolidone, and acetonitrile.

As described above, one step in the preparation of a compound of either of formula I or II comprises providing a polymerization initiator of formula HX(CH$_2$CH$_2$Y)$_m$(CH$_2$)$_n$R$^3$, wherein X, Y, m, n, and $R^3$ are as defined above and described in classes and sub-classes above and herein. One of ordinary skill in the art would recognize that the polymerization initiator of formula HX(CH$_2$CH$_2$Y)$_m$(CH$_2$)$_n$R$^3$ provides the $R^1$ group of formula I or II. Accordingly, embodiments directed to the $R^3$ moiety of said $R^1$ group of formula I or II, as set forth above and herein, are also directed to the $R^3$ moiety of the polymerization initiator of formula v.

Exemplary $R^1$ groups of formula I or II, and corresponding polymerization initiators of formula HX(CH$_2$CH$_2$Y)$_m$(CH$_2$)$_n$R$^3$, are set forth in Table 1, below.

TABLE 1

Representative R¹ Groups and Polymerization Initiators

| R¹ Groups | Polymerization Initiators |
|---|---|
| a (methoxy) | a' (methanol) |
| b (ethoxy) | b' (ethanol) |
| c (propoxy) | c' (propanol) |
| d (butoxy) | d' (butanol) |
| e (pentoxy) | e' (pentanol) |
| f (hexoxy) | f' (hexanol) |
| g (N₃-CH₂CH₂-O-) | g' (N₃-CH₂CH₂-OH) |
| h (Bn₂N-CH₂CH₂-O-) | h' (Bn₂N-CH₂CH₂-OH) |
| i (Allyl₂N-CH₂CH₂-O-) | i' (Allyl₂N-CH₂CH₂-OH) |
| j (Boc-NH-CH₂CH₂-O-) | j' (Boc-NH-CH₂CH₂-OH) |
| k (Phthalimido-CH₂CH₂-O-) | k' (Phthalimido-CH₂CH₂-OH) |

TABLE 1-continued
Representative R¹ Groups and Polymerization Initiators
| R¹ Groups | Polymerization Initiators |
|---|---|
| 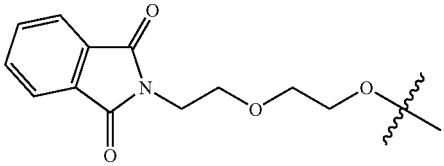 l | 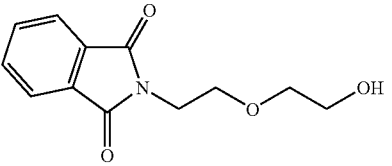 l' |
| 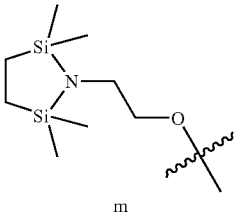 m | 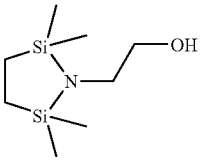 m' |
| 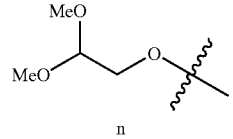 n | 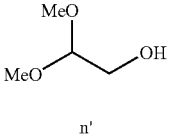 n' |
| 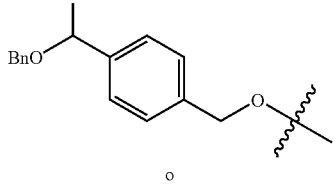 o | 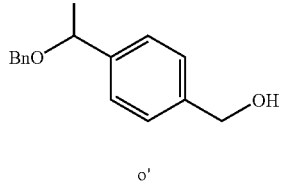 o' |
| 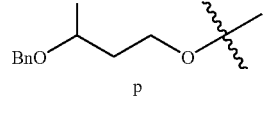 p | 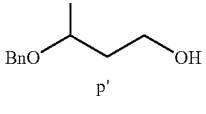 p' |
| 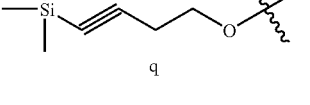 q | 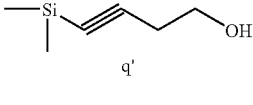 q' |
| 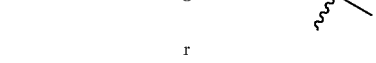 r | 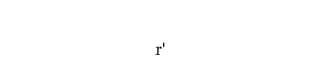 r' |
| 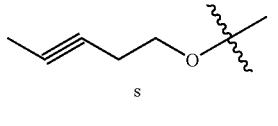 s | 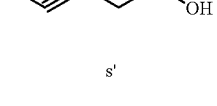 s' |
| 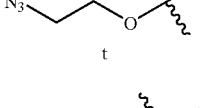 t | 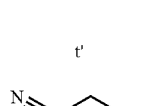 t' |
| 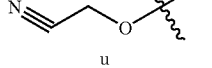 u | 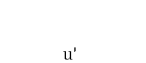 u' |

TABLE 1-continued
Representative R[1] Groups and Polymerization Initiators
| R[1] Groups | Polymerization Initiators |
|---|---|
| 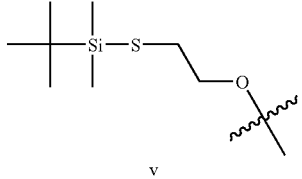 v | 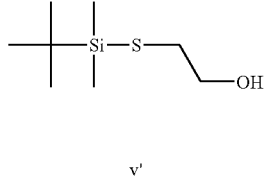 v' |
| 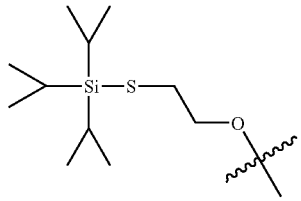 w | 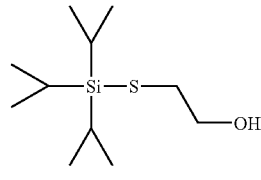 w' |
| 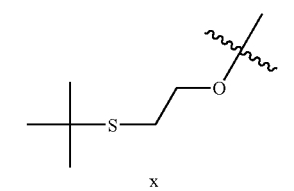 x | 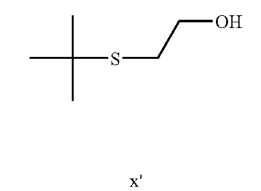 x' |
| 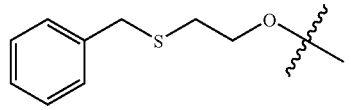 y | 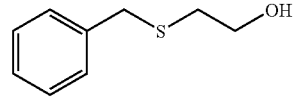 y' |
| 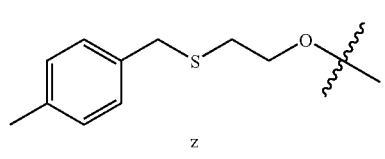 z | 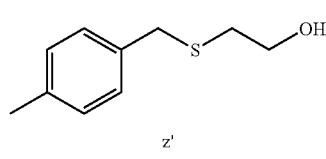 z' |
| 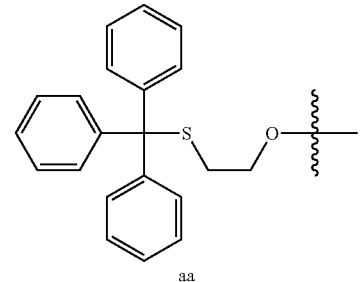 aa | 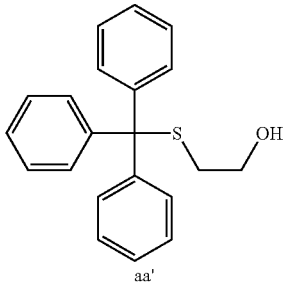 aa' |
| 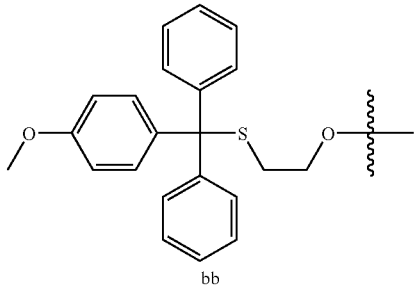 bb | 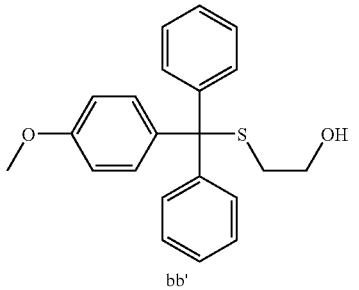 bb' |

TABLE 1-continued
Representative R¹ Groups and Polymerization Initiators
| R¹ Groups | Polymerization Initiators |
|---|---|
| 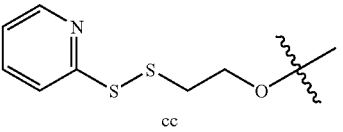 cc | 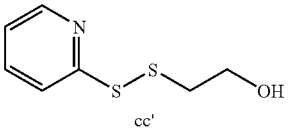 cc' |
| 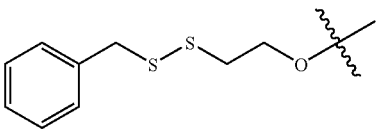 dd | 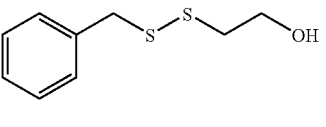 dd' |
| 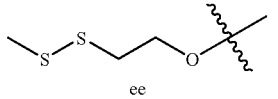 ee | 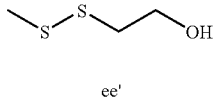 ee' |
| 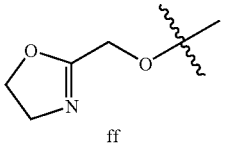 ff | 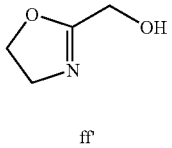 ff' |
| 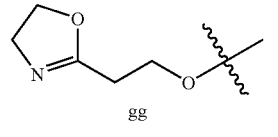 gg | 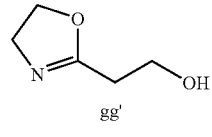 gg' |
| 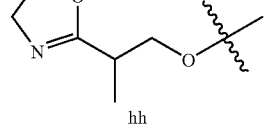 hh | 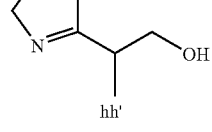 hh' |
| 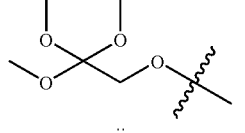 ii | 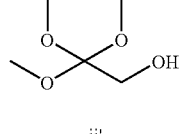 ii' |
| 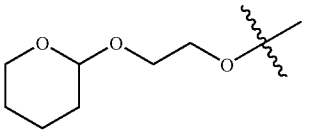 jj | 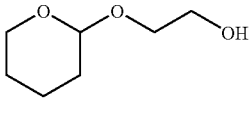 jj' |
| 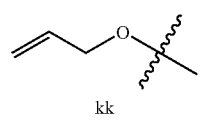 kk | 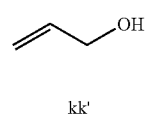 kk' |
| 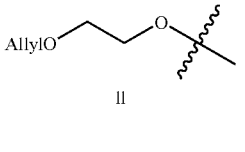 ll | 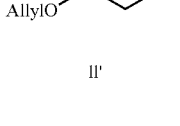 ll' |

TABLE 1-continued
Representative R¹ Groups and Polymerization Initiators
| R¹ Groups | Polymerization Initiators |
|---|---|
| 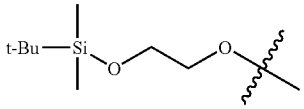 mm | 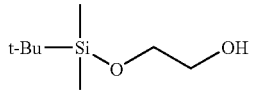 mm' |
| 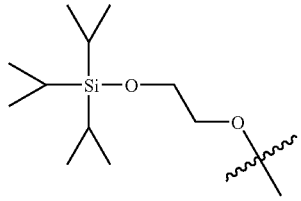 nn | 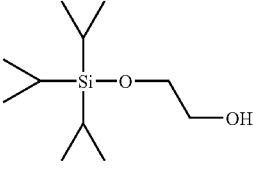 nn' |
| 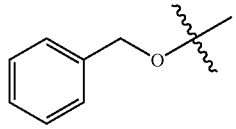 oo | 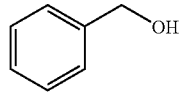 oo' |
| 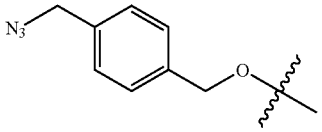 pp | 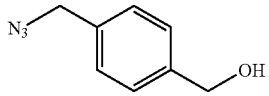 pp' |
| 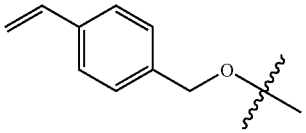 qq | 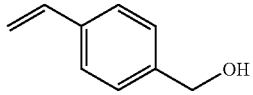 qq' |
| 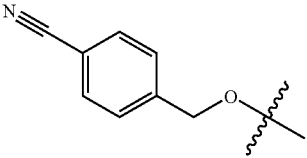 rr | 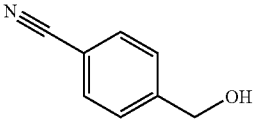 rr' |
| 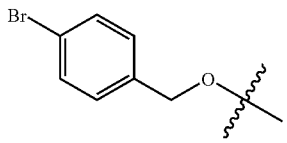 ss | 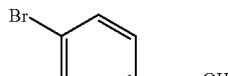 ss' |
| 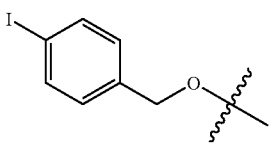 tt | 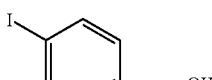 tt' |

TABLE 1-continued
Representative R¹ Groups and Polymerization Initiators
| R¹ Groups | Polymerization Initiators |
|---|---|
| 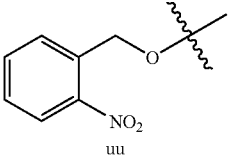 uu | 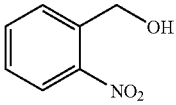 uu' |
| 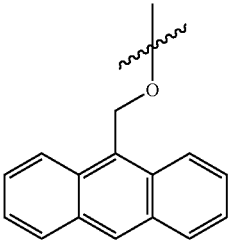 vv | 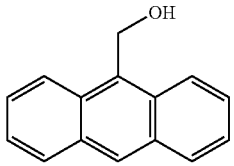 vv' |
| 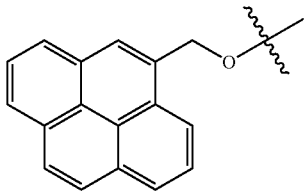 ww | 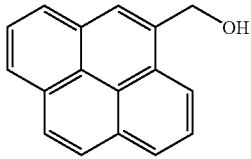 ww' |
| 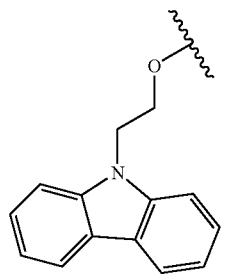 xx | 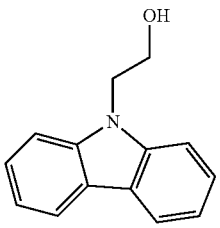 xx' |
| 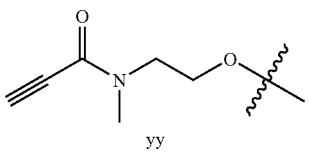 yy | 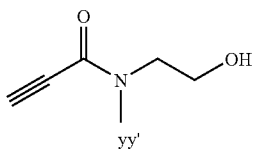 yy' |
| 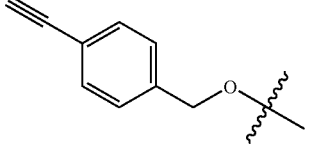 zz | 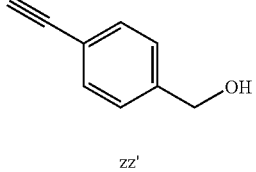 zz' |
| 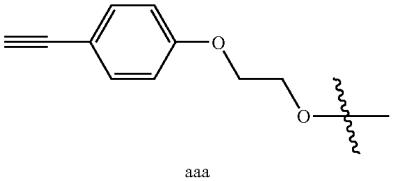 aaa | 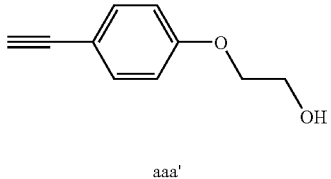 aaa' |

TABLE 1-continued

Representative R¹ Groups and Polymerization Initiators

| R¹ Groups | Polymerization Initiators |
|---|---|
| bbb | bbb' |
| ccc | ccc' |
| ddd | ddd' |
| eee | eee' |
| fff | fff' |
| ggg | ggg' |

TABLE 1-continued
Representative R¹ Groups and Polymerization Initiators
| R¹ Groups | Polymerization Initiators |
|---|---|
| 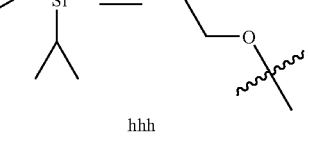 hhh | 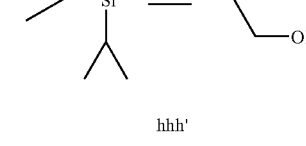 hhh' |
| 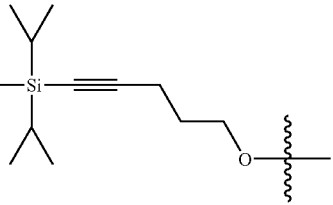 iii | 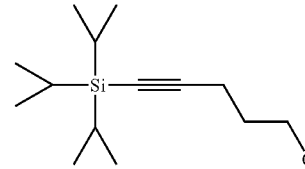 iii' |
|  jjj | 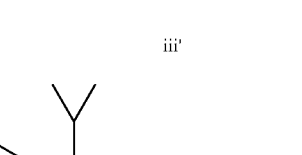 jjj' |
| 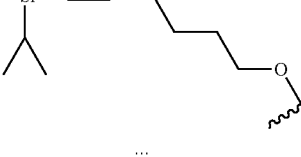 kkk |  kkk' |
| 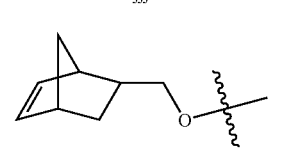 lll | 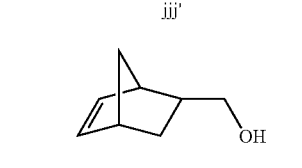 lll' |
| 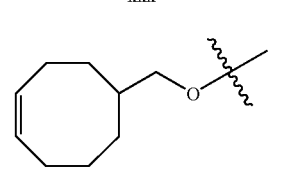 mmm | 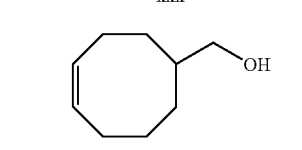 mmm' |
| 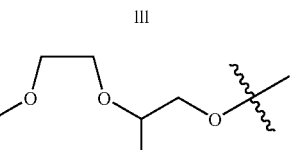 nnn | 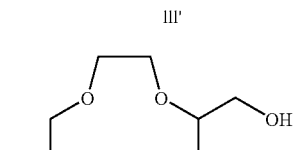 nnn' |

TABLE 1-continued

Representative R¹ Groups and Polymerization Initiators

| R¹ Groups | Polymerization Initiators |
|---|---|
| ooo | ooo' |
| ppp | ppp' |
| qqq | qqq' |
| rrr | rrr' |
| sss | sss' |
| ttt | ttt' |
| uuu | uuu' |

In certain embodiments, the $R^1$ group of either of formula I or II is selected from any of those $R^1$ groups depicted in Table 1, supra. In other embodiments, the $R^1$ group of either of formula I or II is group k or l. In yet other embodiments, the $R^1$ group of either of formula I or II is n, o, cc, dd, ee, ff, hh, h, ii, jj, ll, or uu. In still other embodiments, the $R^1$ group of either of formula I or II is h, aa, yy, zz, or aaa.

According to another aspect of the present invention, the $R^1$ group of either of formula I or II is q, r, s, or t.

According to another aspect of the present invention, the $R^1$ group of either of formula I or II is other than j, q, t, ii, pp, ggg, hhh, iii, or jjj.

In other embodiments, the initiator is selected from those set forth in Table 2 below.

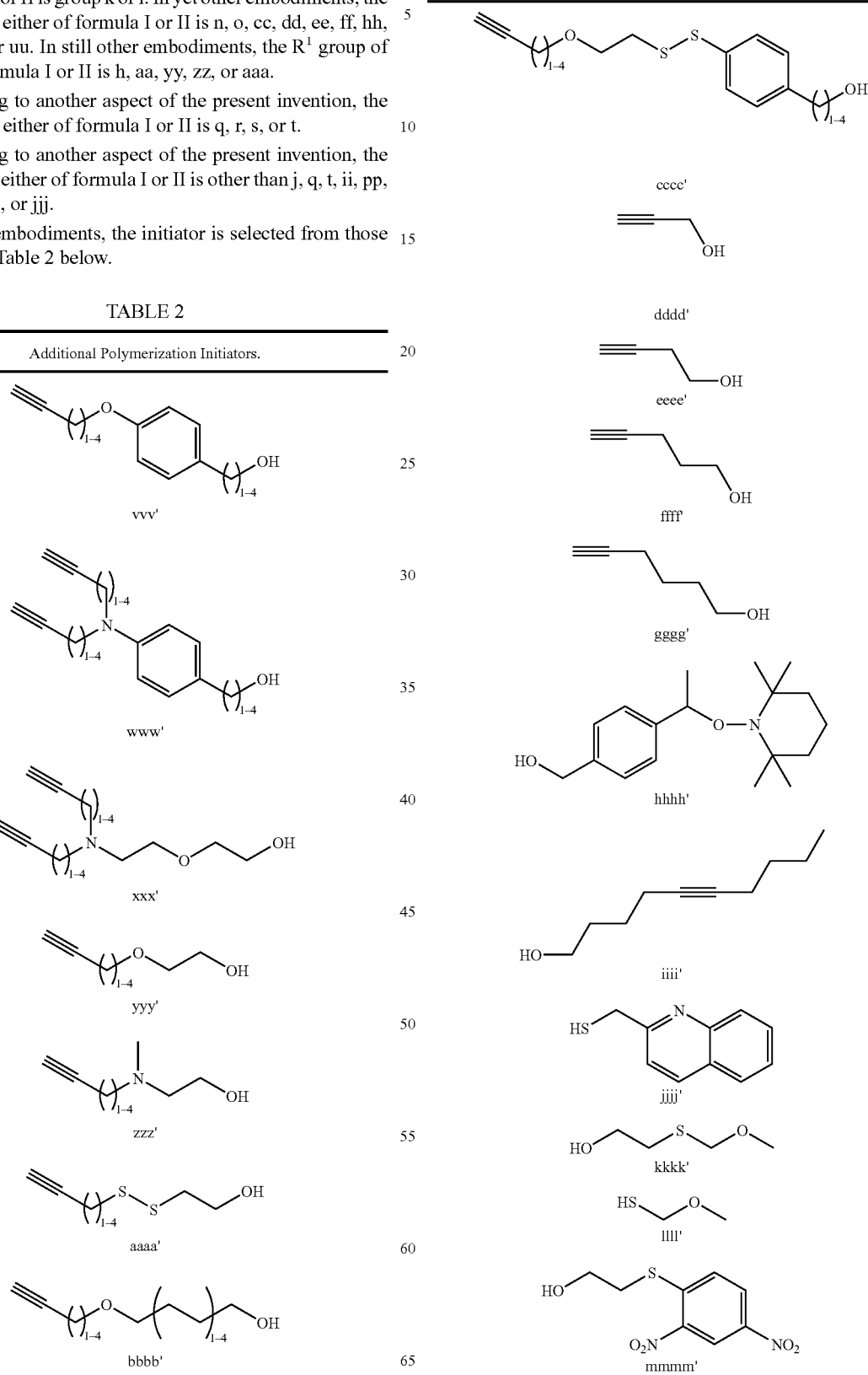

TABLE 2-continued

Additional Polymerization Initiators.

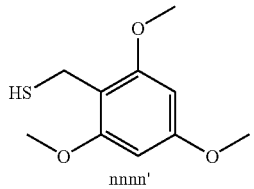

nnnn'

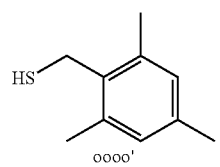

oooo'

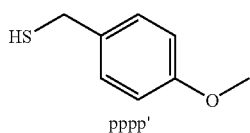

pppp'

In other embodiments, the polymerization initiator is selected from any of those polymerization initiating groups depicted in Table 1, supra. In other embodiments, the polymerization initiator is selected from any of those depicted in Table 2, supra. In still other embodiments, the polymerization initiator is group k' or l'. In still other embodiments, the polymerization initiator is n', o', cc', dd', ee', ff', hh', h', ii', jj', ll', or uu'. In yet other embodiments, the polymerization initiator is h', aa', yy', zz', or aaa'.

According to another aspect of the present invention, the polymerization initiator is q', r', s', or t'.

According to another aspect of the present invention, the polymerization initiator is other than j', q', t', ii', pp', ggg', hhh', iii', or jjj'.

The M moiety of formula II is the cation of a metal capable, with its corresponding anion, of affecting the polymerization of ethylene oxide. In certain embodiments, M is $K^+$, $Cs^+$, $Na^+$, $Al^{(3+)}$, or $Y^+$. In other embodiments, M is $K^+$ or $Na^+$. According to another aspect of the present invention, M is $K^+$. In other embodiments M is a transition metal such as Sn, Pb, Zn, Cd, Cu, Pd, Mn, Cr, Mo, W, Fe, Co or organometallic complexes of these metals. In yet other embodiments, M is a rare-earth metal such as Sc, La, Pr, Nd, Sm, Eu, Gd, Dy, Yb or organometallic complexes of these metals.

As defined generally above, the $R^2$ group of formula I is halogen, $N_3$, CN, a mono-protected amine, a di-protected amine, a protected hydroxyl, a protected aldehyde, a protected thiol, $-NHR^4$, $-N(R^4)_2$, $-SR^4$, $-O(CH_2CH_2O)_q$ $(CH_2)_rR^5$, $-OC(O)R^4$, or $-OS(O)_2R^4$, wherein q and r are each independently 0-4, each $R^4$ is independently an optionally substituted group selected from aliphatic, a 5-8-membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two $R^4$ on the same nitrogen atom are taken together with said nitrogen atom to form an optionally substituted 4-7-membered saturated, partially unsaturated, or aryl ring having 1-4 heteroatoms independently selected from nitrogen, oxygen, or sulfur; and $R^5$ is hydrogen, halogen, CN, a mono-protected amine, a di-protected amine, a protected aldehyde, a protected hydroxyl, a protected carboxylic acid, a protected thiol, or an optionally substituted group selected from aliphatic, a 5-8-membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, In certain embodiments, the $R^2$ group of formula I is $-N_3$.

In other embodiments, the $R^2$ group of formula I is $-CN$.

In other embodiments, the $R^2$ group of formula I is $-Br$, $-Cl$, $-F$, or $-I$.

In certain embodiments, the $R^2$ group of formula I is $-OS(O)_2R^4$, wherein $R^4$ is an optionally substituted aliphatic group, or an optionally substituted 5-8-membered aryl ring. Exemplary $R^4$ groups include p-tolyl and methyl. In certain embodiments, $R^2$ is p-toluenesulfonyloxy or methanesulfonyloxy.

In certain embodiments, the $R^2$ group of formula I is $-OR^4$ wherein $R^4$ is an optionally substituted aliphatic group. One exemplary $R^4$ group is 5-norbornen-2-yl-methyl. According to yet another aspect of the present invention, the $R^2$ group of formula I is $-OR^4$ wherein $R^4$ is a $C_{1-6}$ aliphatic group substituted with $N_3$. Examples include $-CH_2N_3$. In some embodiments, $R^4$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, $R^4$ is an optionally substituted $C_{2-6}$ alkenyl group. Examples include vinyl, allyl, crotyl, 2-propenyl, and but-3-enyl. When $R^4$ group is a substituted aliphatic group, suitable substituents on $R^4$ include $N_3$, CN, and halogen. In certain embodiments, $R^4$ is $-CH_2CN$, $-CH_2CH_2CN$, $-CH_2CH(OCH_3)_2$, 4-(bis-benzyloxymethyl)phenylmethyl, and the like.

According to another aspect of the present invention, the $R^2$ group of formula I is $-OR^4$ wherein $R^4$ is an optionally substituted $C_{2-6}$ alkynyl group. Examples include $-CC\equiv CH$, $-CH_2C\equiv CH$, $-CH_2C\equiv CCH_3$, and $-CH_2CH_2C\equiv CH$. In certain embodiments, $R^2$ is propargyloxy.

In other embodiments, the $R^2$ group of formula I is $-OC(O)R^4$ wherein $R^4$ is an optionally substituted aliphatic group. Examples include methyl, ethyl, propyl, butyl, pentyl, hexyl, acetylenyl, propargyl, but-3-ynyl, vinyl, crotyl, 2-propenyl, azidomethyl, 5-norbornen-2-yl, octen-5-yl, triisopropylsilylacetylenyl, 4-vinylphenyl, 4-dipropargylaminophenyl, 4-propargyloxyphenyl, 4-(2-propargyldisulfanyl)methylphenyl, and 2-(propargyloxycarbonyl)ethyl.

In certain embodiments, the $R^2$ group of formula I is $-OR^4$ wherein $R^4$ is an optionally substituted 5-8-membered aryl ring. In certain embodiments, R4 is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^2$ is 4-t-butoxycarbonylaminophenoxy, 4-azidomethylphenoxy, or 4-propargyloxyphenoxy.

In certain embodiments, the $R^2$ group of formula I is —$OR^4$ wherein $R^4$ is an optionally substituted phenyl ring. Suitable substituents on the $R^4$ phenyl ring include halogen; —$(CH_2)_{0-4}R°$; —$(CH_2)_{0-4}OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$(CH_2)_{0-4}SC(O)R°$; —$(CH_2)_{0-4}C(O)NR°_2$; —$C(S)NR°_2$; —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; $SiR°_3$; wherein each independent occurrence of $R°$ is as defined herein supra. In other embodiments, the $R^2$ group of formula I is —$OR^4$ wherein $R^4$ is phenyl substituted with one or more optionally substituted $C_{1-6}$ aliphatic groups. In still other embodiments, $R^4$ is phenyl substituted with vinyl, allyl, acetylenyl, —$CH_2N_3$, —$CH_2CH_2N_3$, —$CH_2C≡CCH_3$, or —$CH_2C≡CH$.

In certain embodiments, the $R^2$ group of formula I is —$OR^4$ wherein $R^4$ is phenyl substituted with $N_3$, $N(R°)_2$, $CO_2R°$, or $C(O)R°$ wherein each $R°$ is independently as defined herein supra.

In other embodiments, the $R^2$ group of formula I is a protected hydroxyl group. In certain embodiments the protected hydroxyl of the $R^2$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl) ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ether, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the $R^2$ group of formula I is —$N(R^4)_2$ wherein each $R^4$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^2$ group of formula I is —$N(R^4)_2$ wherein the two $R^4$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two $R^4$ groups are taken together to form a 5-6-membered saturated or partially unsaturated ring having one nitrogen wherein said ring is substituted with one or two oxo groups. Such $R^2$ groups include, but are not limited to, phthalimide, maleimide and succinimide.

In certain embodiments, the $R^2$ group of formula I is a mono-protected or di-protected amino group. In certain embodiments $R^2$ is a mono-protected amine. In certain embodiments $R^2$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^2$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^2$ moiety is phthalimido. In other embodiments, the $R^2$ moiety is mono- or di-benzylamino or mono- or di-allylamino.

In other embodiments, the $R^2$ group of formula I is a protected aldehyde group. In certain embodiments the protected aldehydo moiety of $R^2$ is an acyclic acetal, a cyclic acetal, a hydrazone, or an imine. Exemplary $R^2$ groups include dimethyl acetal, diethyl acetal, diisopropyl acetal, dibenzyl acetal, bis(2-nitrobenzyl) acetal, 1,3-dioxane, 1,3-dioxolane, and semicarbazone. In certain embodiments, $R^2$ is an acyclic acetal or a cyclic acetal. In other embodiments, $R^2$ is a dibenzyl acetal.

In yet other embodiments, the $R^2$ group of formula I is a protected carboxylic acid group. In certain embodiments, the protected carboxylic acid moiety of $R^2$ is an optionally substituted ester selected from $C_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of $R^2$ is an oxazoline or an ortho ester. Examples of such protected carboxylic acid moieties include oxazolin-2-yl and 2-methoxy-[1,3]dioxin-2-yl.

According to another embodiment, the $R^2$ group of formula I is a protected thiol group. In certain embodiments, the protected thiol of $R^2$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, $R^2$ is an optionally substituted thioether selected from alkyl, benzyl, or triphenylmethyl, or trichloroethoxycarbonyl thioester. In certain embodmients, $R^3$ is —S—S-pyridin-2-yl, —S—SBn, —S—$SCH_3$, or —S—S(p-ethynylbenzyl). In certain embodiments, $R^3$ is —S—S-pyridin-2-yl.

In still other embodiments, the $R^2$ group of formula I is a detectable moiety. According to another aspect of the invention, the $R^2$ group of formula I is a fluorescent moiety. Such fluorescent moieties are well known in the art and include coumarins, quinolones, benzoisoquinolones, hostasol, and Rhodamine dyes, to name but a few. Exemplary fluorescent moieties comprising $R^2$ include anthracen-9-yl-methoxy, pyren-4-yl-methoxy, 2-(9-H-carbazol-9-yl)-ethoxy, the carboxylate of rhodamine B, and the carboxylate of coumarin 343.

In certain embodiments, the $R^2$ group of formula I is a group suitable for Click chemistry. One of ordinary skill in the art would recognize that certain $R^2$ groups of the present invention are suitable for Click chemistry.

Compounds of formula I having $R^2$ groups suitable for Click chemistry are useful for conjugating said compounds to biological systems such as proteins, viruses, and cells, to name but a few. After conjugation to a biomolecule, drug, cell, substrate, or the like, the other end-group functionality, corresponding to the $R^1$ moiety of formulae I and II, can be used to attach targeting groups for cell specific delivery including, but not limited to, fluorescent dyes, covalent attachment to surfaces, and incorporation into hydrogels. Thus, another embodiment of the present invention provides a method of conjugating the $R^2$ group of a compound of formula I to a macromolecule via Click chemistry. Yet another embodiment of the present invention provides a macromolecule conjugated to a compound of formula I via the $R^2$ group.

According to one embodiment, the $R^2$ group of formula I is an azide-containing group. According to another embodiment, the $R^2$ group of formula I is an alkyne-containing group.

In certain embodiments, the $R^2$ group of formula I has a terminal alkyne moiety. In other embodiments, the $R^2$ group of formula I is an alkyne-containing moiety having an electron withdrawing group. Accordingly, in such embodiments, the $R^2$ group of formula I is

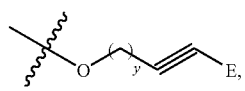

wherein E is an electron withdrawing group and y is 0-6. Such electron withdrawing groups are known to one of ordinary skill in the art. In certain embodiments, E is an ester. In other embodiments, the $R^2$ group of formula I is

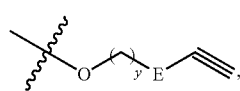

wherein E is an electron withdrawing group, such as a —C(O)O— group and y is 0-6.

Exemplary $R^2$ groups of formula I are set forth in Table 3, below.

TABLE 3

Representative $R^2$ Groups

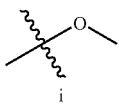

i

TABLE 3-continued

Representative $R^2$ Groups

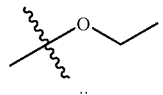

ii

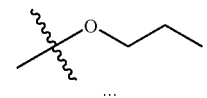

iii

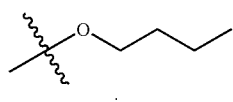

iv

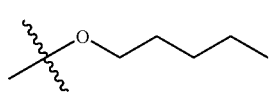

v

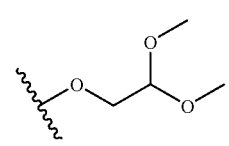

vi

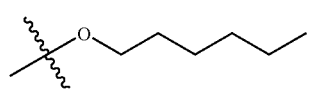

vii

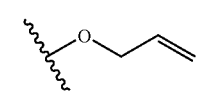

viii

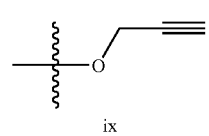

ix

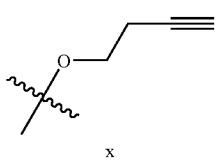

x

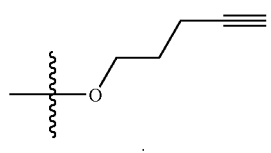

xi

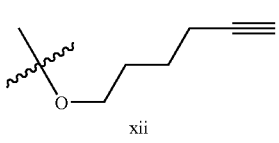

xii

TABLE 3-continued

Representative R² Groups xiii xiv xv xvi xvii xviii xix xx xxi

TABLE 3-continued

Representative R² Groups xxii xxiii xxiv xxv xvi xvii xviii xxix xxx

TABLE 3-continued
Representative R² Groups
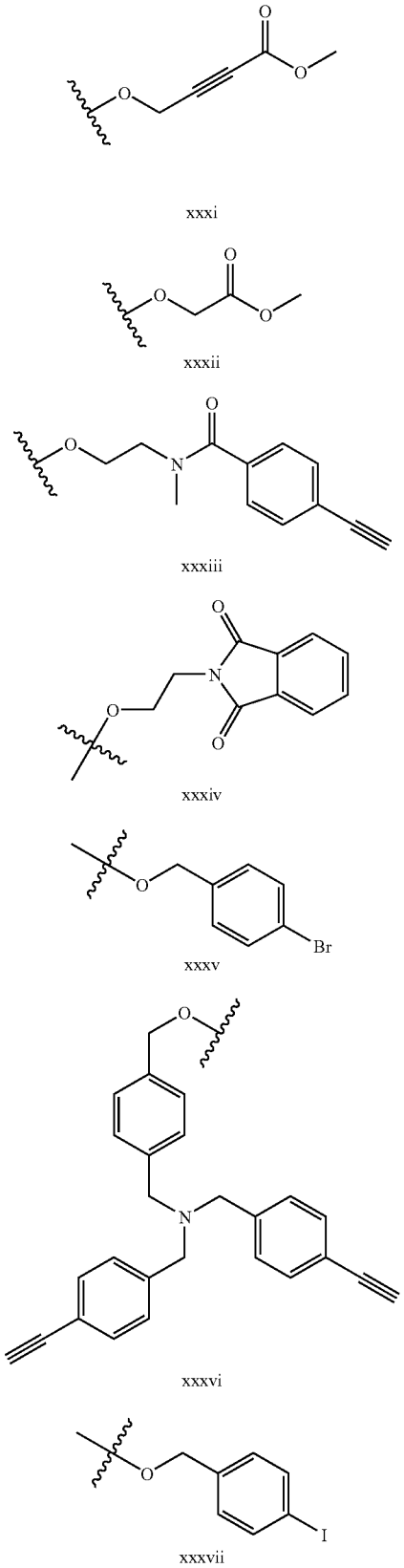
xxxi
xxxii
xxxiii
xxxiv
xxxv
xxxvi
xxxvii
TABLE 3-continued
Representative R² Groups
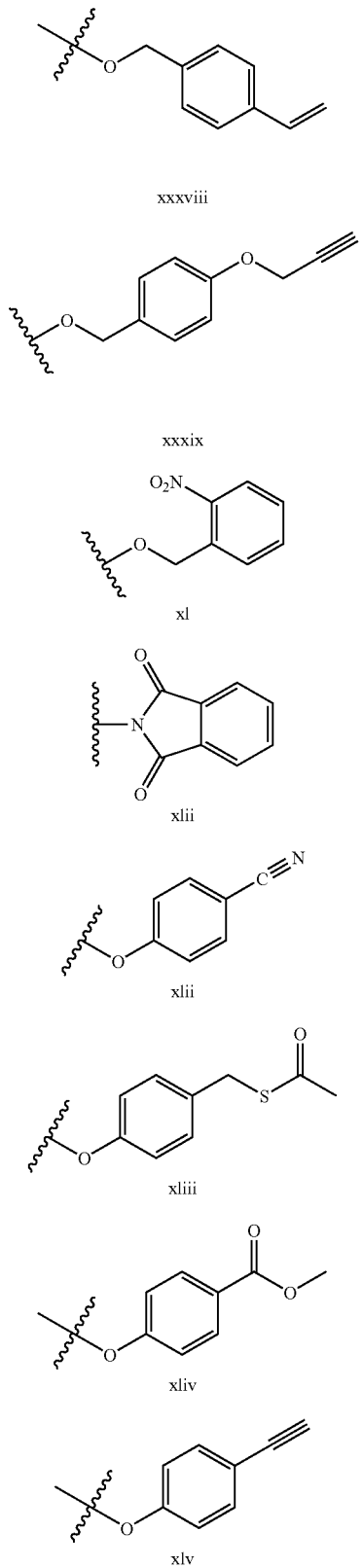
xxxviii
xxxix
xl
xlii
xlii
xliii
xliv
xlv TABLE 3-continued
Representative R² Groups
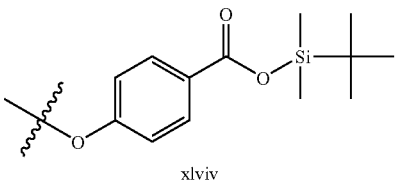
xlviv
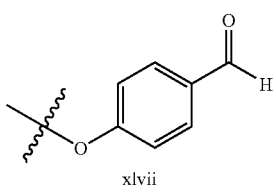
xlvii
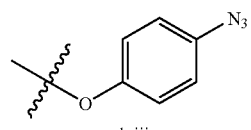
xlviii
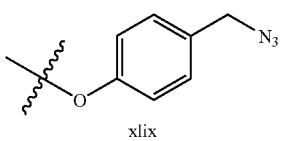
xlix
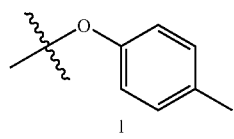
l
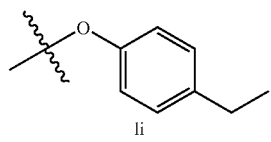
li
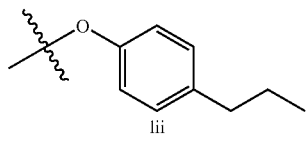
lii
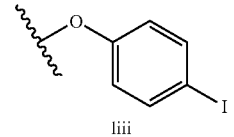
liii
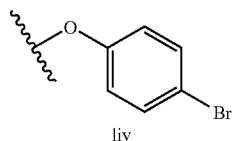
liv
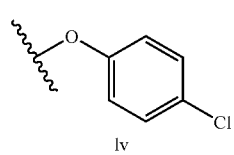
lv
TABLE 3-continued
Representative R² Groups
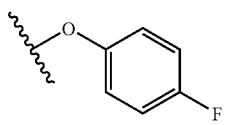
lvi
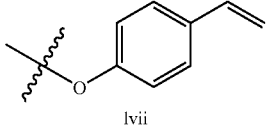
lvii
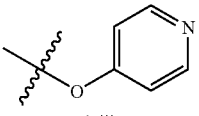
lviii
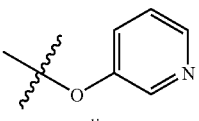
lix
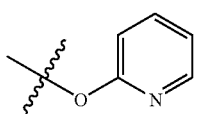
lx
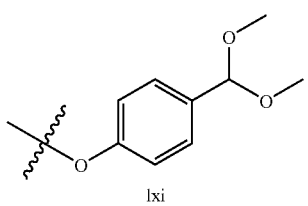
lxi
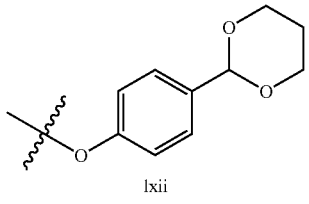
lxii
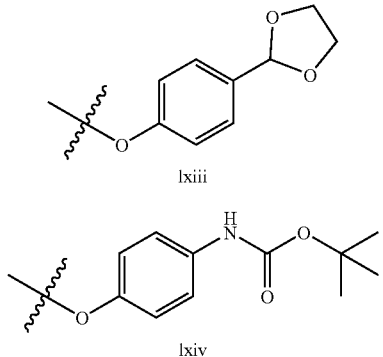
lxiii
lxiv TABLE 3-continued
Representative R² Groups
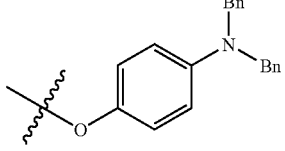
lxi
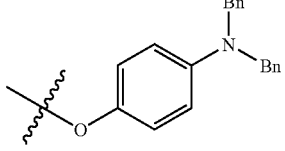
lxii
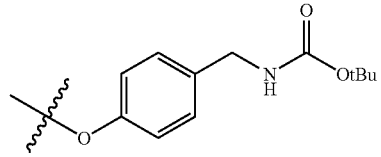
lxiii
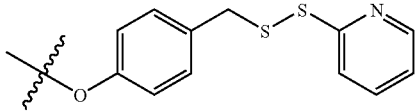
lxiv
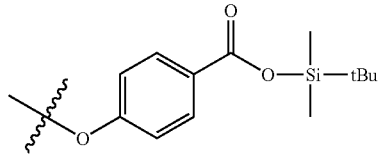
lxv
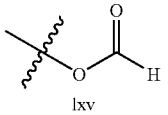
lxvi
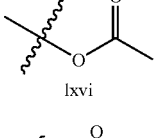
lxvii
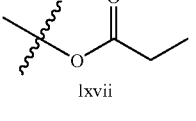
lxviii
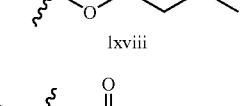
lxix
TABLE 3-continued
Representative R² Groups
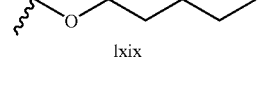
lxx
lxxi
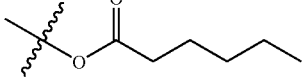
lxxii
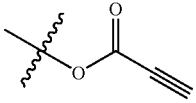
lxxiii
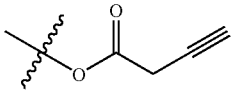
lxxiv
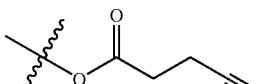
lxxv
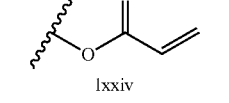
lxxvi
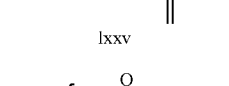
lxxvii
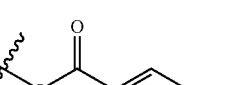
lxxviii
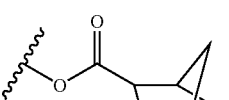
lxxix TABLE 3-continued Representative R² Groups lxxx, lxxxi, lxxxii, lxxxiii, lxxxiv, lxxxv, lxxxvi, lxxxvii, lxxxviii, lxxxix, xc, xci, xcii, xciii, xciv, xcv, xcvi

TABLE 3-continued

Representative R² Groups

[Structures shown: xcvii, xcviii, xcix, c, ci, cii]

In certain embodiments, the R² group of formula I is selected from any of those R² groups depicted in Table 3, supra. In other embodiments, the R² group of formula I is group xlii or xxiv. In yet other embodiments, the R² group of formula I is xix, xvii, xviii, xxix, xxxii, xlviv, xlvii, or xlviii.

According to another aspect of the present invention, the R² group of formula I is ix, xxii, xxx, xxxi, xlv, xlviii, xlix, lxxi.

As described above, one step in the preparation of a compound of formula I comprises terminating the living polymer chain-end of the compound of formula II with a suitable polymerization terminator to afford a compound of formula I. One of ordinary skill in the art would recognize that the polymerization terminator provides the R² group of formula I. Accordingly, embodiments directed to the R² group of formula I, as set forth above and herein, are also directed to the suitable polymerization terminator itself, and similarly, embodiments directed to the suitable polymerization terminator, as set forth above and herein, are also directed to the R² group of formula I.

As described generally above and herein, the present invention provides a method of preparing a compound of formula I:

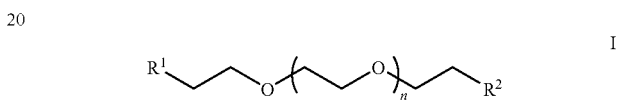
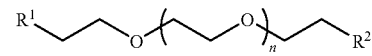

wherein:
n is 10-2500;
R¹ is —X(CH₂CH₂Y)ₘ(CH₂)ₙR³, wherein:
  X is —O—, —S—, —C≡C—, or —CH₂—;
  each Y is independently —O— or —S—;
  m is 0-10;
  n is 0-10; and
  R³ is —N₃, —CN, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
R² is halogen, N₃, CN, a mono-protected amine, a di-protected amine, a protected hydroxyl, a protected aldehyde, a protected thiol, —NHR⁴, —N(R⁴)₂, —SR⁴, —O(CH₂CH₂O)_q(CH₂)ᵣR⁵, —OC(O)R⁴, or —OS(O)₂R⁴;
q and r are each independently 0-4;
each R⁴ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or:
  two R⁴ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur; and
R⁵ is hydrogen, halogen, N₃, CN, a mono-protected amine, a di-protected amine, a protected aldehyde, a protected hydroxyl, a protected carboxylic acid, a protected thiol, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, from a compound of formula II:

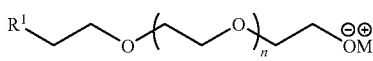

wherein:

M is the cation of a suitable metal;

n is 10-2500;

$R^1$ is $-X(CH_2CH_2Y)_m(CH_2)_nR^3$, wherein:

X is $-O-$, $-S-$, $-C\equiv C-$, or $-CH_2-$;

each Y is independently $-O-$ or $-S-$;

m is 0-10;

n is 0-10; and $R^3$ is $-N_3$, $-CN$, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, comprising the step of terminating the living polymer chain-end of the compound of formula II with a suitable polymerization terminator to afford a compound of formula I.

One of ordinary skill in the art would recognize that the above method is a "one-pot" synthesis of compounds of formula I that utilizes the living polymer chain-end to incorporate the $R^2$ group of formula I. One of ordinary skill in the art would also recognize that compounds of formula I may alternatively be prepared in a multi-step fashion. For example, the living polymer chain-end of a compound of formula II may be quenched to afford an hydroxyl group which may then be further derivatized, according to known methods, to afford a compound of formula I.

Accordingly, the present invention also provides a method for preparing a compound of formula I:

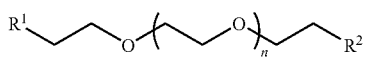

wherein:

n is 10-2500;

$R^1$ is $-X(CH_2CH_2Y)_m(CH_2)_nR^3$, wherein:

X is $-O-$, $-S-$, $-C\equiv C-$, or $-CH_2-$;

each Y is independently $-O-$ or $-S-$;

m is 0-10;

n is 0-10; and $R^3$ is $-N_3$, $-CN$, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

$R^2$ is halogen, $N_3$, CN, a mono-protected amine, a di-protected amine, a protected hydroxyl, a protected aldehyde, a protected thiol, $-NHR^4$, $-N(R^4)_2$, $-SR^4$, $-O(CH_2CH_2O)_q(CH_2)_rR^5$, $-OC(O)R^4$, or $-OS(O)_2R^4$;

q and r are each independently 0-4;

each $R^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or:

two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur; and $R^5$ is hydrogen, halogen, $N_3$, CN, a mono-protected amine, a di-protected amine, a protected aldehyde, a protected hydroxyl, a protected carboxylic acid, a protected thiol, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, from a compound of formula II:

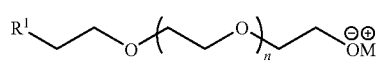

wherein:

M is the cation of a suitable metal;

n is 10-2500;

$R^1$ is $-X(CH_2CH_2Y)_m(CH_2)_nR^3$, wherein:

X is $-O-$, $-S-$, $-C\equiv C-$, or $-CH_2-$;

each Y is independently $-O-$ or $-S-$;

m is 0-10;

n is 0-10; and $R^3$ is $-N_3$, $-CN$, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

comprising the steps of:
(1) providing a polymerization initiator of formula $HX(CH_2CH_2Y)_m(CH_2)_nR^3$, wherein:
X is —O—, —S—, —C≡C—, or —CH$_2$—;
each Y is independently —O— or —S—;
m is 0-10;
n is 0-10; and
$R^3$ is —N$_3$, —CN, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
(2) polymerizing ethylene oxide onto said polymerization initiator to provide a compound of formula II;
(3) quenching said compound of formula II to afford a compound of formula III:

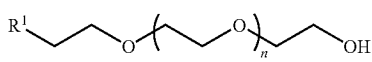

III wherein:
n is 10-2500;
$R^1$ is —$X(CH_2CH_2Y)_m(CH_2)_nR^3$, wherein:
X is —O—, —S—, —C≡C—, or —CH$_2$—;
each Y is independently —O— or —S—;
m is 0-10;
n is 0-10;
$R^3$ is —N$_3$, —CN, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety; and
(4) derivatizing the hydroxyl group of the compound of formula III with a suitable polymer terminating agent to afford a compound of formula I.

One of ordinary skill in the art will recognize that a variety of polymerization terminating agents are suitable for the present invention. Such polymerization terminating agents include any $R^2$-containing group capable of reacting with the living polymer chain-end of a compound of formula II to afford a compound of formula I. Such polymerization terminating agents also include those capable of reacting with either the hydroxyl group of a compound of formula III, or with an activated derivative thereof, to afford a compound of formula I. Thus, polymerization terminating agents include anhydrides, suitable Mitsunobu reactants, and groups that contain a suitable leaving group L that is subject to nucleophilic displacement.

A "suitable leaving group that is subject to nucleophilic displacement" is a chemical group that is readily displaced by a desired incoming chemical moiety. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyloxy (mesyloxy), tosyloxy, triflyloxy, nitro-phenylsulfonyloxy (nosyloxy), and bromo-phenylsulfonyloxy (brosyloxy).

According to an alternate embodiment, the suitable leaving group may be generated in situ within the reaction medium. For example, a leaving group may be generated in situ from a precursor of that compound wherein said precursor contains a group readily replaced by said leaving group in situ.

Derivatization of the hydroxyl group of formula III can be achieved using methods known to one of ordinary skill in the art to obtain a variety of compounds. For example, said hydroxyl group may be transformed to a protected hydroxyl group, or, alternatively, to a suitable leaving group. Hydroxyl protecting groups are well known and include those described above and herein with respect to the $R^1$ and $R^2$ groups of formula I. Such transformations are known to one skilled in the art and include, among others, those described herein.

Alternatively, when the $R^2$ group of formula I is a protected functional group, such as a protected amino, protected thiol, protected carboxylate, protected acetylene, protected aldehyde, etc., the protecting group is removed and that functional group may be derivatized or protected with a different protecting group. It will be appreciated that the removal of any protecting group of the $R^2$ group of formula I is performed by methods suitable for that protecting group. Such methods are described in detail in Green.

According to another embodiment, the present invention provides a compound of formula IV:

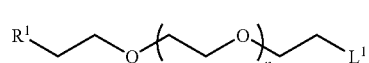

IV wherein:
n is 10-2500;
$R^1$ is —$X(CH_2CH_2Y)_m(CH_2)_nR^3$, wherein:
X is —O—, —S—, —C≡C—, or —CH$_2$—;
each Y is independently —O— or —S—;
m is 0-10;
n is 0-10;
$R^3$ is —N$_3$, —CN, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety; and $L^1$ is a suitable leaving group;
provided that:
(a) $L^1$ is not —OMs when $R^3$ is $(EtO)_2CH$—, Bn-, or MeOC(O)—;
(b) when $R^3$ is CN— or $CH_3C(O)$—, then $L^1$ is not —OTs; and
(c) $L^1$ is not bromo when $R^2$ is unsubstituted phenyl and $R^1$ is

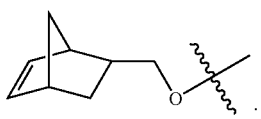

Suitable $L^1$ leaving groups of formula IV include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyloxy (mesyloxy), tosyloxy, triflyoxy, nitro-phenylsulfonyloxy (nosyloxy), and bromo-phenylsulfonyloxy (brosyloxy).

It will be appreciated that after the hydroxyl group of formula III is converted to a suitable leaving group, a variety of functional groups may be incorporated to form a compound of formula I. For example, said leaving group by be displaced by halides, amines, imides, alcohols, phenols, thiols, carboxylic acids, sulfonic acids, and azide to form a compound of formula I. One of ordinary skill in the art would also recognize that these groups may be activated in order to affect said displacement.

One of ordinary skill in the art would recognize that a variety of $R^2$ groups can be incorporated to form a compound of formula I by utilizing the appropriate polymerization terminating agent. These polymerization terminating agents may be used for the "one-pot" method by reacting with the living polymer chain-end of a compound of formula II:

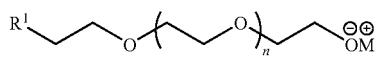

II wherein $R^1$, n, and M are as defined above and herein. Such polymerization terminating agents include those having a leaving group and others capable of reacting with the living polymer chain-end.

Alternatively, these polymerization terminating agents may be used for the multi-step method by reacting with the hydroxyl end of a compound of formula III:

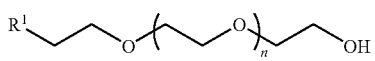

III wherein $R^1$ and n are as defined above and herein. Such polymerization terminating agents include anhydrides, those amenable to Mitsunobu coupling, and those having a leaving group i.e. capable of nucleophilic displacement by the hydroxyl group of the living polymer chain-end.

In certain embodiments, the $R^2$ group of formula I is incorporated by derivatization of the hydroxyl group of formula III via Mitsunobu coupling. The Mitsunobu reaction is a mild method for achieving formal substitution of the hydroxyl group using azodicarboxylic esters/amides and triphenylphosphine (TPP) or trialkylphosphines or phosphites. In addition, other azo compounds have been developed as alternatives to the traditional azodicarboxylic esters diethylazodicarboxylate (DEAD) and diisopropylazodicarboxylate (DIAD). These include dibenzyl azodicarboxylate (DBAD), N,N,N',N'-tetramethylazodicarbonamide (TMAD), and dipiperidyl azodicarboxylate (DPAD). Mitsunobu coupling provides access to terminal groups including, but not limited to, halides, azide, amines, esters, ethers, thioethers and isothiocyanates. Accordingly, it will be appreciated that a variety of compounds of formula I are obtained by the derivatization of the hydroxyl group of formula III by Mitsunobu reaction.

In certain embodiments, the polymerization terminating agent is one that is capable of Mistunobu coupling. These include optionally substituted phenols, optionally substituted thiophenols, cyclic imides, carboxylic acids, azide, and other reagents capable of Mitsunobu coupling. Such Mitsunobu terminating agents include, but are not limited to, those set forth in Table 4, below.

TABLE 4

Representative Mitsunobu Polymerization Terminating Agents

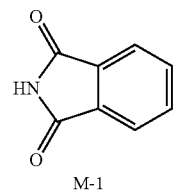

M-1

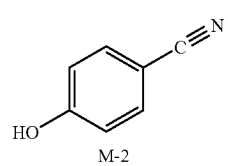

M-2

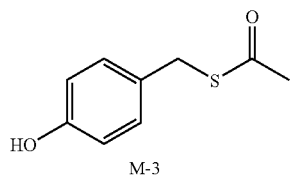

M-3

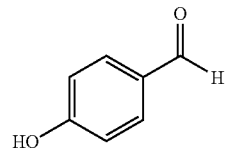

M-4

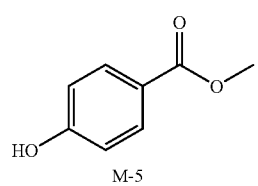

M-5

TABLE 4-continued
Representative Mitsunobu Polymerization Terminating Agents
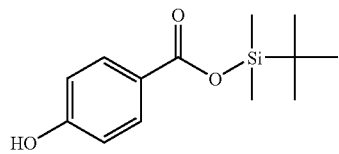
M-6
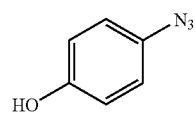
M-7
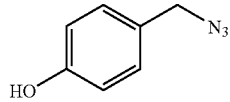
M-8
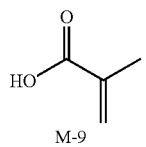
M-9
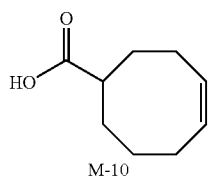
M-10
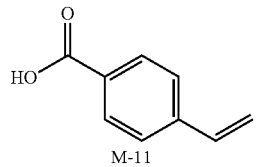
M-11
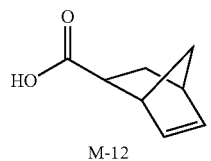
M-12
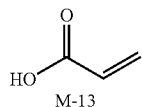
M-13
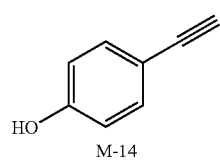
M-14
TABLE 4-continued
Representative Mitsunobu Polymerization Terminating Agents
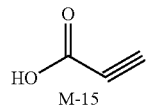
M-15
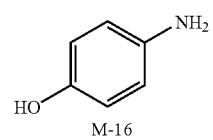
M-16
M-17
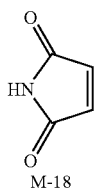
M-18
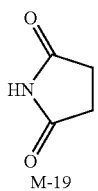
M-19
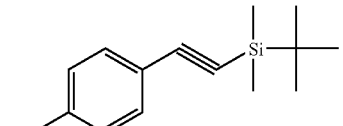
M-20
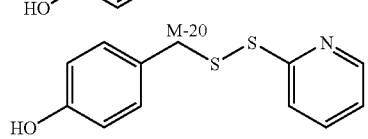
M-21
M-22
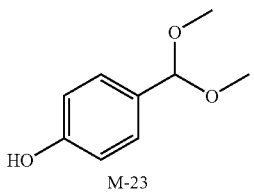
M-23
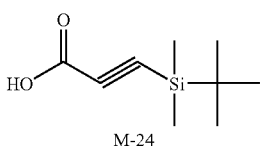
M-24

TABLE 4-continued
Representative Mitsunobu Polymerization Terminating Agents
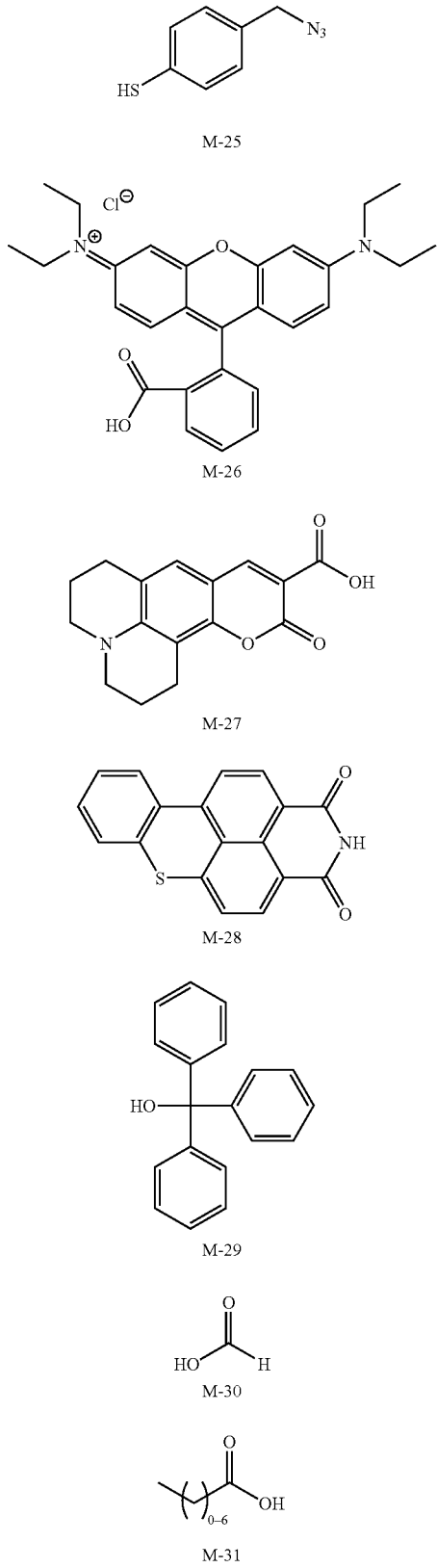
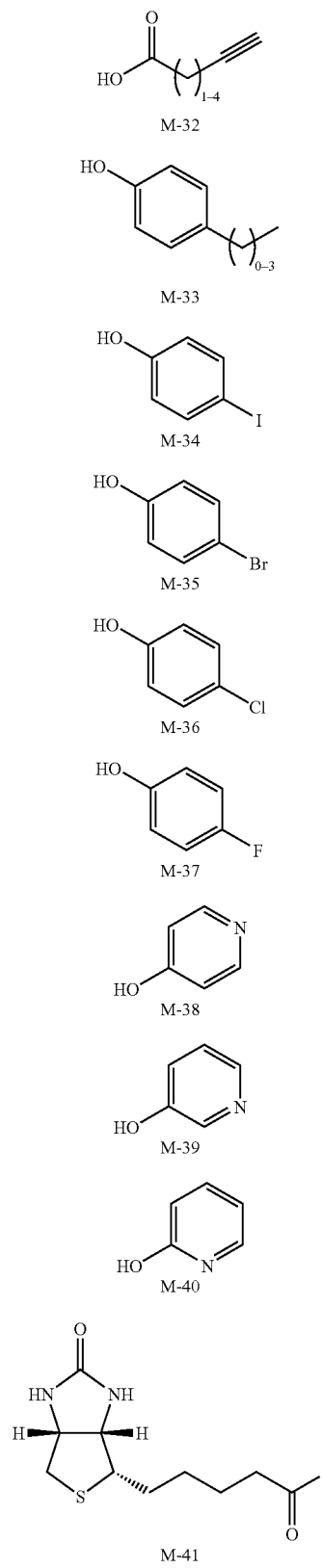

TABLE 4-continued
Representative Mitsunobu Polymerization Terminating Agents
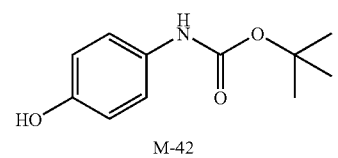
M-42
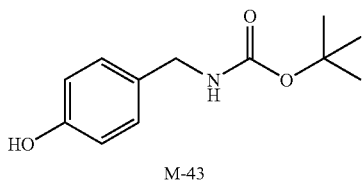
M-43
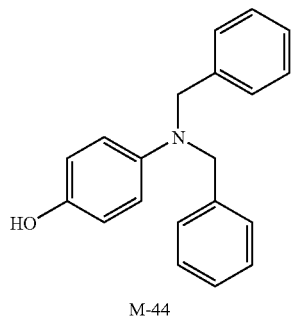
M-44
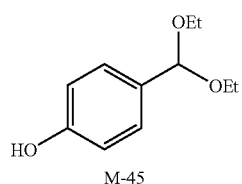
M-45
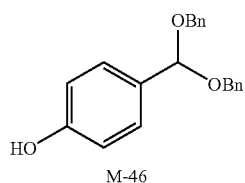
M-46
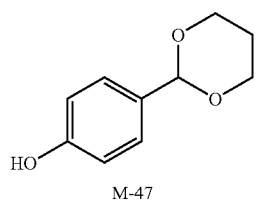
M-47
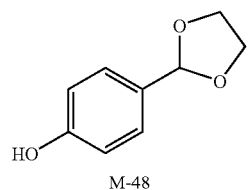
M-48
TABLE 4-continued
Representative Mitsunobu Polymerization Terminating Agents
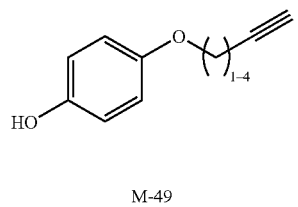
M-49
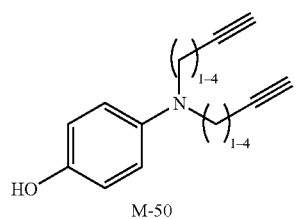
M-50
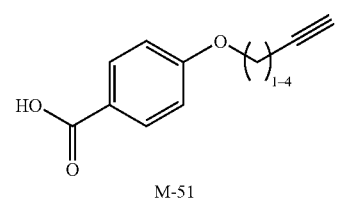
M-51
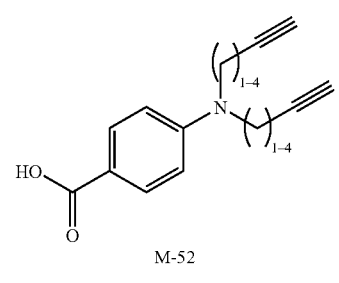
M-52
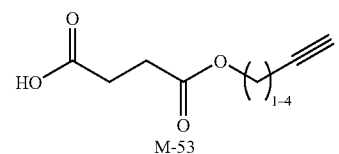
M-53
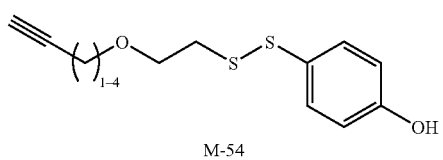
M-54
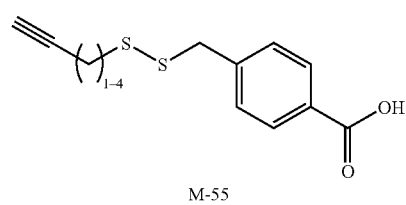
M-55
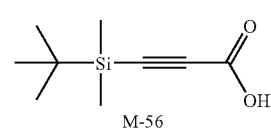
M-56

TABLE 4-continued

Representative Mitsunobu Polymerization Terminating Agents

M-57

M-58

M-59

NaBr
M-60
NaI
M-61
H—N₃
M-62
Na—N₃
M-63

M-64

M-65

M-66

M-67

M-68

M-69

M-70

M-71

M-72

M-73

M-74

M-75

TABLE 4-continued

Representative Mitsunobu Polymerization Terminating Agents

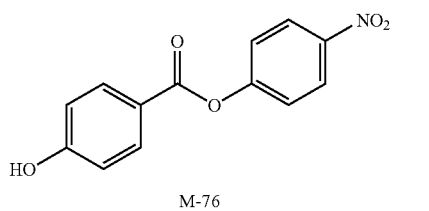

M-76

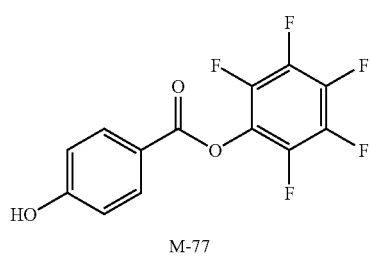

M-77

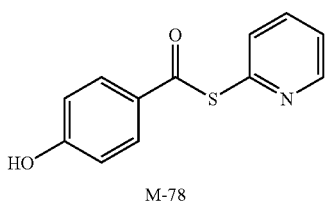

M-78

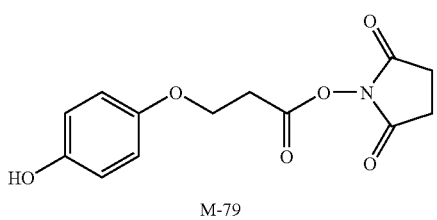

M-79

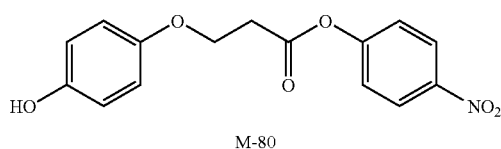

M-80

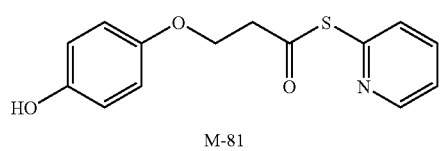

M-81

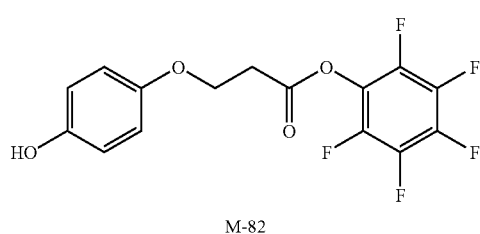

M-82

TABLE 4-continued

Representative Mitsunobu Polymerization Terminating Agents

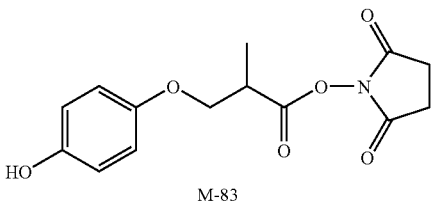

M-83

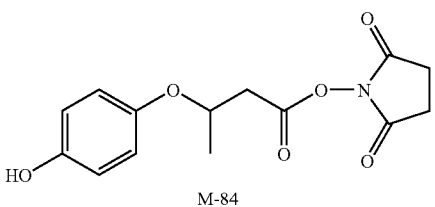

M-84

In other embodiments, the $R^2$ group of formula I is incorporated by derivatization of the hydroxyl group of formula III via anhydride coupling. One of ordinary skill in the art would recognize that anhydride polymerization terminating agents containing an azide, an aldehyde, a protected hydroxyl, an alkyne, and other groups, may be used to incorporate said azide, said aldehyde, said protected hydroxyl, said alkyne, and other groups into the $R^2$ group of compounds of formula I. It will also be appreciated that such anhydride polymerization terminating agents are also suitable for terminating the living polymer chain-end of a compound of formula II. Such anhydride polymerization terminating agents include, but are not limited to, those set forth in Table 5, below.

TABLE 5

Representative Anhydride Polymerization Terminating Agents

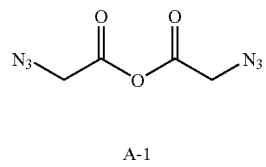

A-1

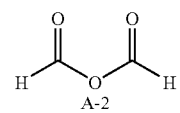

A-2

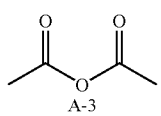

A-3

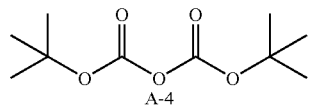

A-4

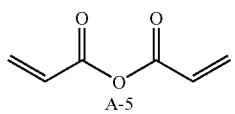

A-5

TABLE 5-continued

Representative Anhydride Polymerization Terminating Agents

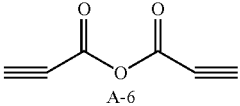
A-6

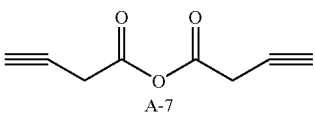
A-7

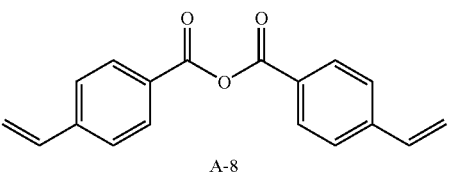
A-8

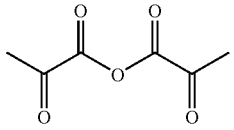
A-9

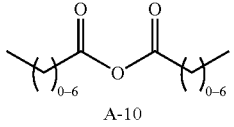
A-10

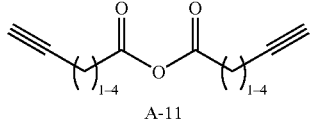
A-11

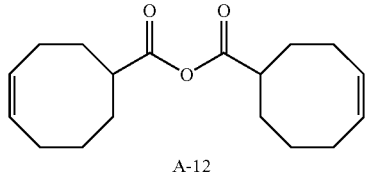
A-12

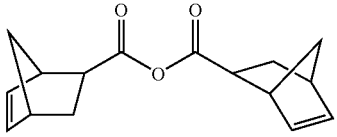
A-13

In other embodiments, the $R^2$ group of formula I is incorporated by derivatization of the hydroxyl group of formula III via reaction with a polymerization terminating agent having a suitable leaving group. It will also be appreciated that such polymerization terminating agents are also suitable for terminating the living polymer chain-end of a compound of formula II. Examples of these polymerization terminating agents include, but are not limited to, those set forth in Table 6, below.

TABLE 6

Representative Polymerization Termination Agents

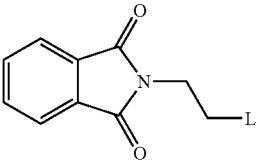
L-1

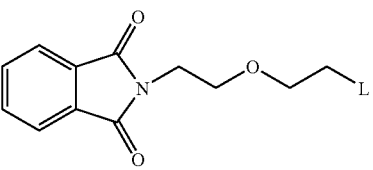
L-2

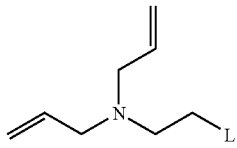
L-3

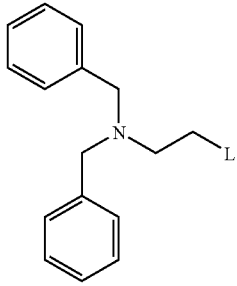
L-4

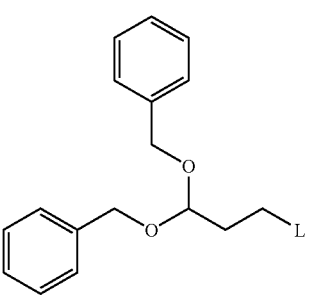
L-5

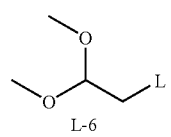
L-6

TABLE 6-continued
Representative Polymerization Termination Agents
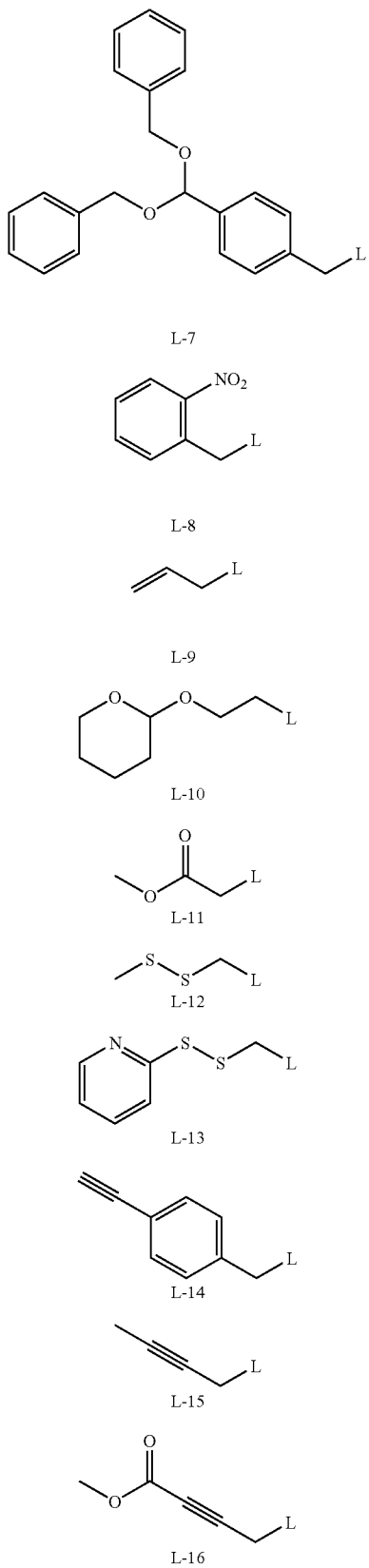
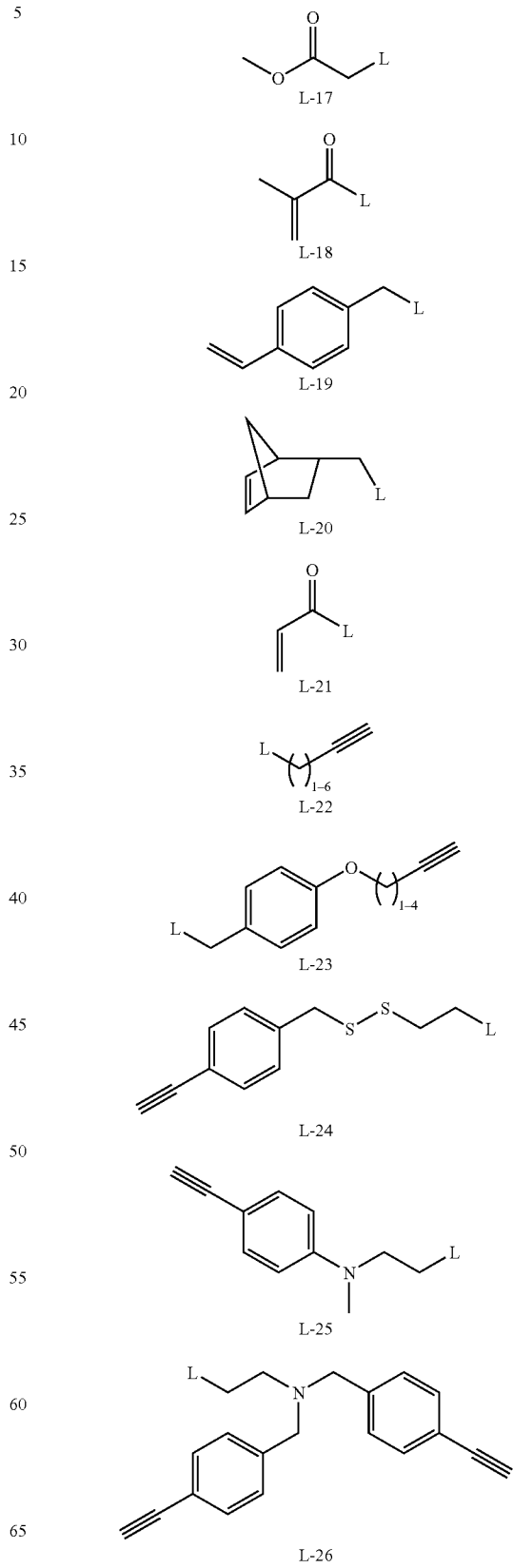

TABLE 6-continued
Representative Polymerization Termination Agents
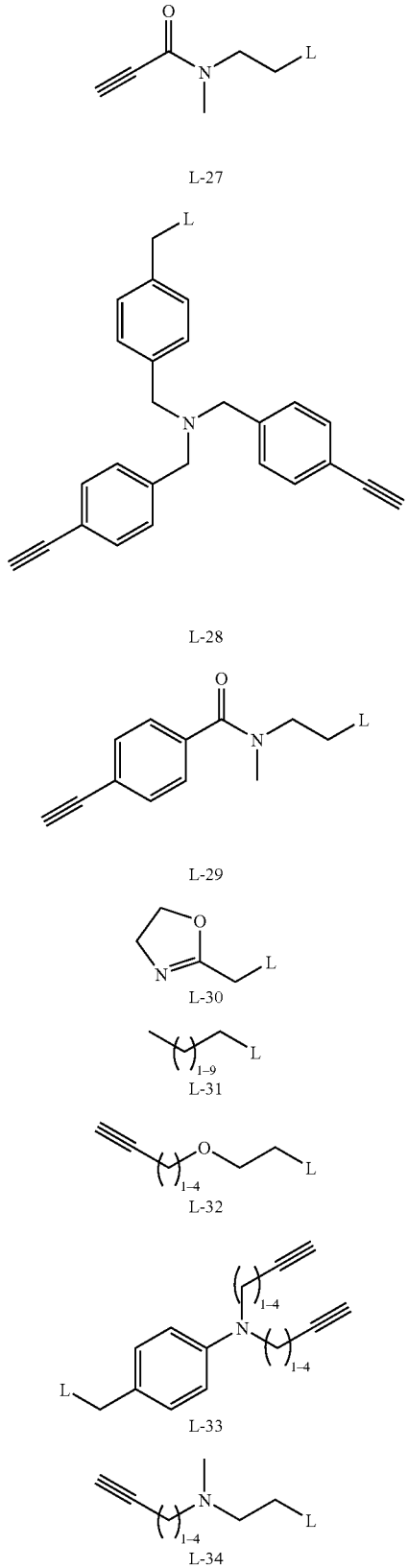
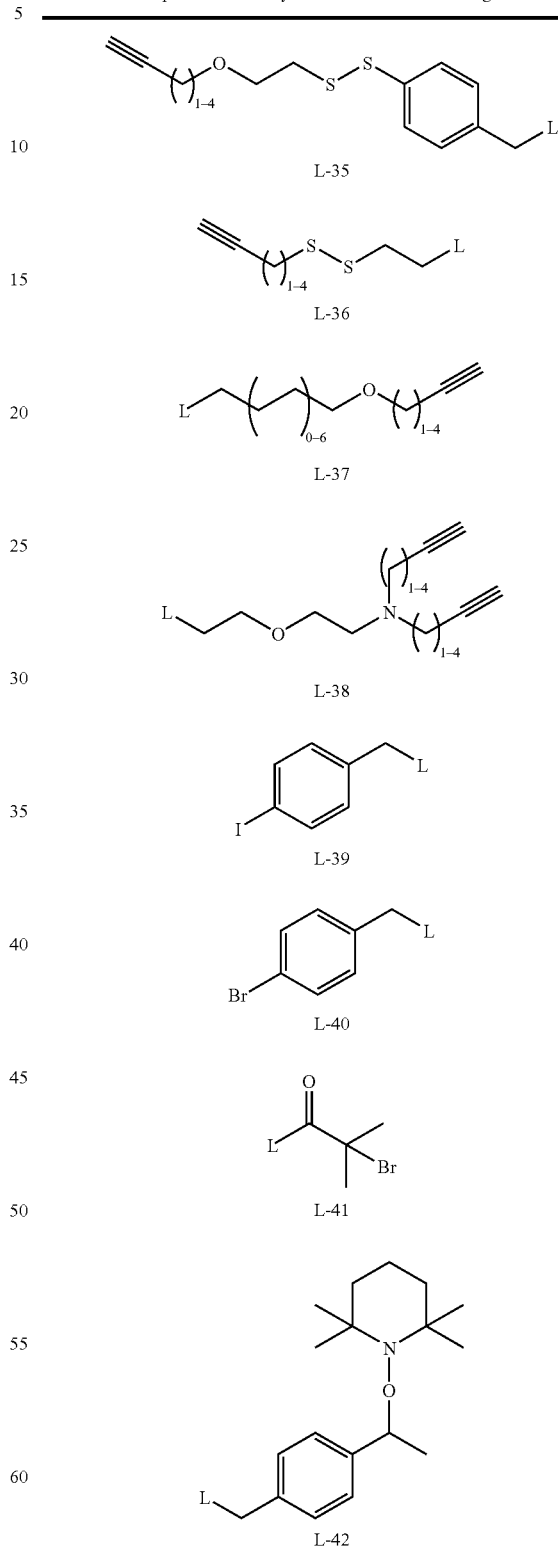
wherein each L is a suitable leaving group as defined above and in classes and subclasses as described above and herein.

According to another embodiment, the present invention provides a compound of formula I':

wherein:
n is 10-2500;
$R^1$ is —X(CH$_2$CH$_2$Y)$_m$(CH$_2$)$_n$R$^3$, wherein:
  X is —O—, —S—, —C≡C—, or —CH$_2$—;
  each Y is independently —O— or —S—;
  m is 0-10;
  n is 0-10; and
  $R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
$R^2$ is halogen, N$_3$, CN, a mono-protected amine, a di-protected amine, a protected hydroxyl, a protected aldehyde, a protected thiol, —NHR$^4$, —N(R$^4$)$_2$, —SR$^4$, —O(CH$_2$CH$_2$O)$_q$(CH$_2$)$_r$R$^5$, —OC(O)R$^4$, or —OS(O)$_2$R$^4$;
q and r are each independently 0-4;
each $R^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or:
  two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur; and
$R^5$ is hydrogen, halogen, N$_3$, CN, a mono-protected amine, a di-protected amine, a protected aldehyde, a protected hydroxyl, a protected carboxylic acid, a protected thiol, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety.

In certain embodiments, the present invention provides a compound of formula I', as described above, wherein the $R^1$ and $R^2$ groups of formula I' are different from each other.

In yet other embodiments, the present invention provides a compound of formula I', as described above, wherein only one of the $R^3$ moiety of the $R^1$ group or the $R^2$ group of formula I' is a suitably protected hydroxyl.

In yet other embodiments, the present invention provides a compound of formula I', as described above, wherein neither the $R^3$ moiety of the $R^1$ group nor the $R^2$ group of formula I' is a suitably protected hydroxyl.

In yet other embodiments, the present invention provides a method for preparing a compound of formula I', as described above, wherein the $R^3$ moiety of the $R^1$ group is not methyl and the R group of formula I' is not —Omethyl.

As described generally above, the $R^1$ group of formula I' is —X(CH$_2$CH$_2$Y)$_m$(CH$_2$)$_n$R$^3$, wherein X is —O—, —S—, —C≡C—, or —CH$_2$—, each Y is independently —O— or —S—, m is 0-10, n is 0-10; and $R^3$ is —N$_3$, —CN, a mono-protected amine, a di-protected amine, a protected aldehyde, a protected hydroxyl, a protected carboxylic acid, a protected thiol, a 9-30-membered crown ether, an optionally substituted aliphatic group, an optionally substituted 5-8-membered saturated, partially unsaturated, or aryl ring having 0-4 heteroatoms independently selected from nitrogen, oxygen, or sulfur, an optionally substituted 8-10-membered saturated, partially unsaturated, or aryl bicyclic ring having 0-5 heteroatoms independently selected from nitrogen, oxygen, or sulfur, or a detectable moiety.

In certain embodiments, the $R^3$ moiety of the $R^1$ group of formula I' is —N$_3$. In certain embodiments, $R^1$ is other than 2-azidoethoxy.

In certain embodiments, the $R^3$ moiety of the $R^1$ group of formula I' is —CN.

In certain embodiments, the $R^3$ moiety of the $R^1$ group of formula I' is an optionally substituted aliphatic group. Examples include t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said $R^3$ moiety is an optionally substituted alkyl group. In other embodiments, said $R^3$ moiety is an optionally substituted alkynyl or alkenyl group. When said $R^3$ moiety is a substituted aliphatic group, suitable substituents on $R^3$ include CN, N$_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, or 2-propargyldisulfanyl. In certain embodiments, the $R^1$ group is 2-(N-methyl-N-(ethynylcarbonyl)amino)ethoxy, 4-ethynylbenzyloxy, or 2-(4-ethynylphenoxy)ethoxy. In certain embodiments, $R^1$ is other than propargyloxy, 1-(but-3-yn)oxy, 3-t-butyldimethylsilylpropargyloxy, 3-triisopropylsilylpropargyloxy, 1-(6-t-butyldimethylsilyl-hex-5-yn)oxy, or 1-(6-triisopropylsilylhex-5-yn)oxy.

In certain embodiments, the $R^3$ moiety of the $R^1$ group of formula I' is an optionally substituted aryl group. Examples include optionally substituted phenyl, and optionally substituted pyridyl. When said $R^3$ moiety is a substituted aliphatic group, suitable substituents on $R^3$ include CN, N$_3$, NO$_2$, —CH$_3$, —CH$_2$N$_3$, —CH=CH$_2$, —C≡CH, Br, I, F, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl. In certain embodiments, $R^1$ is other than 4-azidomethylbenzyloxy.

In other embodiments, the $R^3$ moiety of the $R^1$ group of formula I' is a protected hydroxyl group. In certain embodiments the protected hydroxyl of the $R^3$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ether, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ethers. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the $R^3$ moiety of the $R^1$ group of formula I' is a mono-protected or di-protected amino group. In certain embodiments $R^3$ is a mono-protected amine. In certain embodiments $R^3$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^3$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^3$ moiety is phthalimido. In certain embodiments, the $R^1$ group is 2-dibenzylaminoethoxy. In still other embodiments, the $R^1$ group is other than 2-t-butoxycarbonylamino-ethoxy.

In other embodiments, the $R^3$ moiety of the $R^1$ group of formula I' is a protected aldehyde group. In certain embodiments the protected aldehydo moiety of $R^3$ is an acyclic acetal, a cyclic acetal, a hydrazone, or an imine. Exemplary $R^3$ groups include dimethyl acetal, diethyl acetal, diisopropyl acetal, dibenzyl acetal, bis(2-nitrobenzyl) acetal, 1,3-dioxane, 1,3-dioxolane, and semicarbazone. In certain embodiments, $R^3$ is an acyclic acetal or a cyclic acetal. In other embodiments, $R^3$ is a dibenzyl acetal.

In yet other embodiments, the $R^3$ moiety of the $R^1$ group of formula I' is a protected carboxylic acid group. In certain embodiments, the protected carboxylic acid moiety of $R^3$ is an optionally substituted ester selected from $C_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of $R^3$ is an oxazoline or an ortho ester. Examples of such protected carboxylic acid moieties include oxazolin-2-yl and 2-methoxy-[1,3]dioxin-2-yl. In certain embodiments, the $R^1$ group is oxazolin-2-ylmethoxy or 2-oxazolin-2-yl-1-propoxy. In certain embodiments, $R^1$ is other than 2-methoxy-[1,3]dioxin-2-ylmethoxy.

According to another embodiment, the $R^3$ moiety of the $R^1$ group of formula I' is a protected thiol group. In certain embodiments, the protected thiol of $R^3$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, $R^3$ is an optionally substituted thioether selected from alkyl, benzyl, or triphenylmethyl, or trichloroethoxycarbonyl thioester. In certain embodmients, $R^3$ is —S—S-pyridin-2-yl, —S—SBn, —S—SCH$_3$, or —S—S(p-ethynylbenzyl). In certain embodmients, $R^3$ is —S—S-pyridin-2-yl. In certain embodiments, the $R^1$ group is 2-triphenylmethylsulfanyl-ethoxy.

In certain embodiments, the $R^3$ moiety of the $R^1$ group of either of formula I' is a crown ether. Exemplary crown ethers that comprise the $R^3$ moiety of the $R^1$ include 12-crown-4, 15-crown 5, and 18-crown-6.

In still other embodiments, the $R^3$ moiety of the $R^1$ group of formula I' is a detectable moiety. According to another aspect of the invention, the $R^1$ group of formula I' is a fluorescent moiety. Such fluorescent moieties are well known in the art and include coumarins, quinolones, benzoisoquinolones, hostasol, and Rhodamine dyes to name but a few. Exemplary fluorescent moieties of the $R^3$ group of $R^1$ include anthracen-9-yl, pyren-4-yl, 9-H-carbazol-9-yl, the carboxylate of rhodamine B, and the carboxylate of coumarin 343.

In certain embodiments, the $R^3$ moiety of the $R^1$ group of formula I' is a group suitable for Click chemistry. One of ordinary skill in the art would recognize that certain $R^3$ moieties of the present invention are suitable for Click chemistry.

Compounds of formula I' having $R^3$ moieties suitable for Click chemistry are useful for conjugating said compounds to biological systems such as proteins, viruses, and cells, to name but a few. After conjugation to a biomolecule, drug, cell, or the like, the other end-group functionality, corresponding to the $R^2$ moiety of formula I', can be used to attach targeting groups for cell specific delivery including, but not limited to, detectable groups, covalent attachment to surfaces, and incorporation into hydrogels.

In certain embodiments, the $R^3$ group of formula I' is —N$_3$, —CN, or an optionally substituted aliphatic group.

In other embodiments, the $R^3$ group of formula I' is —N$_3$, —CN, or an alkynyl group.

According to one embodiment, the $R^3$ moiety of the $R^1$ group of formula I' an azide-containing group.

According to another embodiment, the $R^3$ moiety of the $R^1$ group of formula I' is an alkyne-containing group. In certain embodiments, the $R^3$ moiety of the $R^1$ group of formula I' has a terminal alkyne moiety. In other embodiments, $R^3$ moiety of the $R^1$ group of formula I' is an alkyne moiety having an electron withdrawing group. Accordingly, in such embodiments, the $R^3$ group of formula I' is

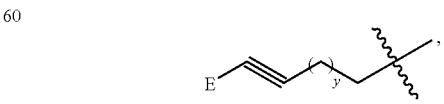

wherein E is an electron withdrawing group and y is 0-6. Such electron withdrawing groups are known to one of ordinary skill in the art. In certain embodiments, E is —C(O)O—. In other embodiments, the $R^3$ group of formula I' is

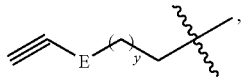

wherein E is an electron withdrawing group, such as a —C(O)O— group and y is 0-6.

In certain embodiments, the $R^1$ group of formula I' is selected from any of those $R^1$ groups depicted in Table 1, supra. In other embodiments, the $R^1$ group of formula I' is group k or l, wherein each group is as depicted in Table 1, supra. In yet other embodiments, the $R^1$ group of formula I' is n, o, cc, dd, ee, ff, hh, h, ii, jj, ll, or uu, wherein each group is as depicted in Table 1, supra. In still other embodiments, the $R^1$ group of formula I' is h, aa, yy, zz, or aaa, wherein each group is as depicted in Table 1, supra.

According to another aspect of the present invention, the $R^1$ group of formula I' is q, r, s, or t, wherein each group is as depicted in Table 1, supra.

According to another aspect of the present invention, the $R^1$ group of either of formula I' is other than j, q, t, ii, pp, ggg, hhh, iii, or jjj, wherein each group is as depicted in Table 1, supra.

As defined generally above, the $R^2$ group of formula I' is halogen, a mono-protected amine, a di-protected amine, a protected hydroxyl, a protected aldehyde, a protected thiol, —$NHR^4$, —$N(R^4)_2$, —$SR^4$, —$O(CH_2CH_2O)_q(CH_2)_rR^5$, —$OC(O)R^4$, or —$OS(O)_2R^4$, and each $R^4$ is independently hydrogen, a mono-protected amine, a di-protected amine, a protected aldehyde, a protected hydroxyl, a protected carboxylic acid, a protected thiol, an optionally substituted aliphatic group, an optionally substituted 5-8-membered saturated, partially unsaturated, or aryl ring having 0-4 heteroatoms independently selected from nitrogen, oxygen, or sulfur, an optionally substituted 8-10-membered saturated, partially unsaturated, or aryl bicyclic ring having 0-5 heteroatoms independently selected from nitrogen, oxygen, or sulfur, or a detectable moiety, or two $R^4$ on the same nitrogen atom are taken together with said nitrogen atom to form an optionally substituted 4-7-membered saturated, partially unsaturated, or aryl ring having 1-4 heteroatoms independently selected from nitrogen, oxygen, or sulfur.

In certain embodiments, the $R^2$ group of formula I' is —$N(R^4)_2$ wherein each $R^4$ is independently an optionally substituted group selected from aliphatic, phenyl, naphthyl, a 5-6-membered aryl ring having 1-4 heteroatoms independently selected from nitrogen, oxygen, or sulfur, or a 8-10-membered bicyclic aryl ring having 1-5 heteroatoms independently selected from nitrogen, oxygen, or sulfur, or a detectable moiety.

In other embodiments, the $R^2$ group of formula I' is —$N(R^4)_2$ wherein the two $R^4$ groups are taken together with said nitrogen atom to form an optionally substituted 4-7-membered saturated, partially unsaturated, or aryl ring having 1-4 heteroatoms independently selected from nitrogen, oxygen, or sulfur. According to another embodiment, the two $R^4$ groups are taken together to form a 5-6 membered saturated or partially unsaturated ring having one nitrogen wherein said ring is substituted with one or two oxo groups. Such $R^2$ groups include, but are not limited to, maleimide and succinimide.

In certain embodiments, the $R^2$ group of formula I' is —$N_3$. In certain embodiments, the $R^2$ group of formula I' is —CN.

In other embodiments, the $R^2$ group of formula I' is —Br, —Cl, —F, or —I.

In certain embodiments, the $R^2$ group of formula I' is —$OS(O)_2R^4$, wherein $R^4$ is an optionally substituted aliphatic group, or an optionally substituted 5-8 membered aryl ring. Exemplary $R^4$ groups include p-tolyl and methyl. In certain embodiments, $R^2$ is p-toluenesulfonyloxy or methanesulfonyloxy.

In certain embodiments, the $R^2$ group of formula I' is —$OR^4$ wherein $R^4$ is an optionally substituted aliphatic group. One exemplary $R^4$ group is 5-norbornen-2-yl-methyl. According to yet another aspect of the present invention, the $R^2$ group of formula I is —$OR^4$ wherein $R^4$ is a $C_{1-6}$ aliphatic group substituted with $N_3$. Examples include —$CH_2N_3$. In some embodiments, $R^4$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, $R^4$ is an optionally substituted $C_{2-6}$ alkenyl group. Examples include vinyl, allyl, crotyl, 2-propenyl, and but-3-enyl. When $R^4$ group is a substituted aliphatic group, suitable substituents on $R^4$ include $N_3$, CN, and halogens. Such $R^4$ aliphatic groups include, but are not limited to, —$CH_2CN$, —$CH_2CH_2CN$, —$CH_2CH(OCH_3)_2$, 4-(bisbenzyloxymethyl)phenylmethyl, and the like.

According to another aspect of the present invention, the $R^2$ group of formula I' is —$OR^4$ wherein $R^4$ is an optionally substituted $C_{2-6}$ alkynyl group. Examples include —CC≡CH, —$CH_2$C≡CH, —$CH_2$C≡$CCH_3$, and —$CH_2CH_2$C≡CH. In certain embodiments, $R^2$ is propargyloxy.

In other embodiments, the $R^2$ group of formula I' is —$OC(O)R^4$ wherein $R^4$ is an optionally substituted aliphatic group. Examples include methyl, ethyl, propyl, butyl, pentyl, hexyl, acetylenyl, propargyl, but-3-ynyl, vinyl, crotyl, 2-propenyl, azidomethyl, 5-norbornen-2-yl, octen-5-yl, triisopropylsilylacetylenyl, 4-vinylphenyl, 4-dipropargylaminophenyl, 4-propargyloxyphenyl, 4-(2-propargyldisulfanyl)methylphenyl, and 2-(propargyloxycarbonyl)ethyl.

In certain embodiments, the $R^2$ group of formula I' is —$OR^4$ wherein $R^4$ is an optionally substituted 5-8-membered aryl ring. In certain embodiments, $R^4$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^2$ is 4-t-butoxycarbonylaminophenoxy, 4-azidomethylphenoxy, or 4-propargyloxyphenoxy.

In certain embodiments, the $R^2$ group of formula I' is —$OR^4$ wherein $R^4$ is an optionally substituted phenyl ring. Suitable substituents on the $R^4$ phenyl ring include halogen; —$(CH_2)_{0-4}R^\circ$; —$(CH_2)_{0-4}OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with R°; —CH═CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —(CH$_2$)$_{0-4}$SC(O)R°; —(CH$_2$)$_{0-4}$C(O)NR°$_2$; —C(S)NR°$_2$; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; SiR°$_3$; wherein each independent occurrence of R° is as defined herein supra. In other embodiments, the R$^2$ group of formula I is —OR$^4$ wherein R$^4$ is phenyl substituted with one or more optionally substituted C$_{1-6}$ aliphatic groups. In still other embodiments, R$^4$ is phenyl substituted with vinyl, allyl, acetylenyl, —CH$_2$N$_3$, —CH$_2$CH$_2$N$_3$, —CH$_2$C≡CCH$_3$, or —CH$_2$C≡CH.

In certain embodiments, the R$^2$ group of formula I' is —OR$^4$ wherein R$^4$ is phenyl substituted with N$_3$, N(R°)$_2$, CO$_2$R°, or C(O)R° wherein each R° is independently as defined herein supra.

In other embodiments, the R$^2$ group of formula I' is a protected hydroxyl group. In certain embodiments the protected hydroxyl of the R$^2$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ethers, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ethers. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the R$^2$ group of formula I' is a mono-protected or di-protected amino group. In certain embodiments R$^2$ is a mono-protected amine. In certain embodiments R$^2$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments R$^2$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the R$^2$ moiety is phthalimido. In other embodiments, the R$^2$ moiety is mono- or di-benzylamino or mono- or di-allylamino.

In other embodiments, the R$^2$ group of formula I' is a protected aldehyde group. In certain embodiments the protected aldehydo moiety of R$^2$ is an acyclic acetal, a cyclic acetal, a hydrazone, or an imine. Exemplary R$^2$ groups include dimethyl acetal, diethyl acetal, diisopropyl acetal, dibenzyl acetal, bis(2-nitrobenzyl) acetal, 1,3-dioxane, 1,3-dioxolane, and semicarbazone. In certain embodiments, R$^2$ is an acyclic acetal or a cyclic acetal. In other embodiments, R$^2$ is a dibenzyl acetal.

In yet other embodiments, the R$^2$ group of formula I' is a protected carboxylic acid group. In certain embodiments, the protected carboxylic acid moiety of R$^2$ is an optionally substituted ester selected from C$_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of R$^2$ is an oxazoline or an ortho ester. Examples of such protected carboxylic acid moieties include oxazolin-2-yl and 2-methoxy-[1,3]dioxin-2-yl.

According to another embodiments, the R$^2$ group of formula I' is a protected thiol group. In certain embodiments, the protected thiol of R$^2$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, R$^2$ is an optionally substituted thioether selected from alkyl, benzyl, or triphenylmethyl, or trichloroethoxycarbonyl thioester. In certain embodmients, R$^3$ is —S—S-pyridin-2-yl, —S—SBn, —S—SCH$_3$, or —S—S(p-ethynylbenzyl). In certain embodmients, R$^3$ is —S—S-pyridin-2-yl.

In still other embodiments, the R$^2$ group of formula I' is a detectable moiety. According to another aspect of the invention, the R$^2$ group of formula I' is a fluorescent moiety. Such fluorescent moieties are well known in the art and include coumarins, quinolones, benzoisoquinolones, hostasol, and Rhodamine dyes to name but a few. Exemplary fluorescent moieties comprising R$^2$ include anthracen-9-yl-methoxy, pyren-4-yl-methoxy, 2-(9-H-carbazol-9-yl)-ethoxy, the carboxylate of rhodamine B, and the carboxylate of coumarin 343.

In certain embodiments, the R$^2$ group of formula I' is a group suitable for Click chemistry. One of ordinary skill in the art would recognize that certain R$^2$ groups of the present invention are suitable for Click chemistry.

Compounds of formula I' having R$^2$ groups suitable for Click chemistry are useful for conjugating said compounds to biological systems such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule.

After conjugation to a biomolecule, drug, cell, or the like, the other end-group functionality, corresponding to the R$^1$ moiety of formula I', can be used to attach targeting groups for cell specific delivery including, but not limited to, detectable groups, covalent attachment to surfaces, and incorporation into hydrogels.

According to one embodiment, the $R^2$ group of formula I' is an azide-containing group. According to another embodiment, the $R^2$ group of formula I' is an alkyne-containing group.

In certain embodiments, the $R^2$ group of formula I' has a terminal alkyne moiety. In other embodiments, the R group of formula I' is an alkyne-containing moiety having an electron withdrawing group. Accordingly, in such embodiments, the $R^2$ group of formula I' is

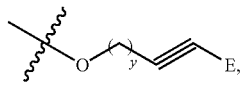

wherein E is an electron withdrawing group and y is 0-6. Such electron withdrawing groups are known to one of ordinary skill in the art. In certain embodiments, E is an ester. In other embodiments, the $R^2$ group of formula I' is

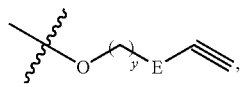

wherein E is an electron withdrawing group, such as a —C(O)O— group and y is 0-6.

According to another embodiment, the present invention provides compounds of formula I', as described above, wherein said compounds have a polydispersity index ("PDI") of about 1.0 to about 1.2. According to another embodiment, the present invention provides compounds of formula I', as described above, wherein said compound has a polydispersity index ("PDI") of about 1.03 to about 1.15. According to yet another embodiment, the present invention provides compounds of formula I', as described above, wherein said compound has a polydispersity index ("PDI") of about 1.10 to about 1.12. According to other embodiments, the present invention provides compounds of formula I' having a PDI of less than about 1.10.

In certain embodiments, n is about 225. In other embodiments, n is about 200 to about 300. In still other embodiments, n is about 200 to about 250. In still other embodiments, n is about 100 to about 150. In still other embodiments, n is about 400 to about 500.

In some embodiments, compounds of the present invention are capable of polymerizing additional unsaturated monomers by controlled free radical polymerization ("CFRP"), or "living" radical polymerization. One of ordinary skill in the art would recognize that CFRP can be used to polymerize unsaturated monomers in a fashion whereby chain transfer and termination reactions can be minimized resulting in the growth of one or more polymer blocks with predictable polymer length and polydispersity index (PDI). Vinyl monomers capable of undergoing CFRP include styrene, methyl methacrylate, acrylic acid, to name but a few.

In some embodiments, compounds of the present invention possess a stable, nitroxide free radical moiety (—O—N($R^°$)$_2$) capable of nitroxide mediated radical polymerization (NMRP). In other embodiments, compounds of the present invention perform reversible addition-fragmentation chain transfer polymerization (RAFT). RAFT agents typically possess dithioester or trithiocarbonate functionality, among others, and can polymerize a wide range of monomers including, but not limited to, styrene and acrylate derivatives. In still other embodiments, compounds of the present invention possess functionality capable of performing atom transfer radical polymerization (ATRP). These functionalities include those which are halogenated (e.g. bromine) and form stable free radicals capable of polymerizing a wide range of unsaturated compounds. In certain cases, additional catalytic reagents (e.g. transition metal catalysts and appropriate organic ligands) are optionally added to improve the kinetics of ATRP.

Without wishing to be bound by any particular theory, it is believed that in each of these controlled radical polymerizations, the radical chain end is trapped in a dormant state for a large majority of the polymerization. However, an equilibrium exists between this dormant state and an active radical chain end that is capable of polymerizing vinyl monomers. Thus a dynamic equilibrium exists that allows for the capping group to disassociate from the chain end, radically add one or more monomer units, then return to the protected state. The relevance of the protected state is that the number of active radicals in the polymerization at any given time is greatly reduced and termination events are nearly eliminated, giving rise to narrow (<1.2) polydispersity indicies and predictable molecular weights. Each polymerization technique has it's own respective strengths and shortcomings, and each offer varying degree of control over molecular weight and polydispersity. NMRP offers a very simple approach whereby typically no additional radical initiators or metals are used. However, the controlled polymerization of acrylate monomers is difficult. RAFT employs a dithioester or trithiocarbonate functionality as the chain transfer group following initiation with a radical source for the polymerization of a wide range of monomers including, but not limited to, styrene and acrylate derivatives. ATRP utilizes a halogen atom, typically bromine, as the radical capping group. A copper catalyst and amine ligands are used to disassociate the bromine from the secondary, tertiary, or benzyl carbon to generate the radical. ATRP also polymerizes a wide range of vinyl monomers and operates at lower temperatures (room temperature) than nitroxide or RAFT polymerizations.

According to one embodiment, the compounds of formulae I', are as defined herein provided that:
(a) when either of $R^1$ or $R^2$ is (EtO)$_2$CH—, then the other of $R^1$ or $R^2$ is not —S—S-pyridin-2-yl, —OBn, —OC(O)C(CH$_3$)=CH$_2$, or —OC(O)CH=CH—CH=CH-Ph;
(b) when either of $R^1$ or $R^2$ is —OBn, the other is not —OC(O)Cl;
(c) $R^1$ and $R^2$ are not simultaneously —OC(O)CH=CH$_2$;
(d) when either of $R^1$ or $R^2$ is —CN, then the other is not -phthalimido;
(e) when either of $R^1$ or $R^2$ is acetyl, then the other is not —CN or -phthalimido;

According to another embodiment, the compounds of formulae I', as defined herein, exclude one or more of the following groups of compounds:
(f) (alkyl)O-PEG-CH$_2$CH$_2$R$^2$, wherein $R^2$ is as defined above;
(g) (cycloalkyl)O-PEG-CH$_2$CH$_2$R$^2$, wherein $R^2$ is as defined above;
(h) HO-PEG-CH$_2$CH$_2$R$^2$, wherein $R^2$ is as defined above;
(i) $R^1$—CH$_2$CH$_2$—PEG-CH$_2$CH$_2$OH, wherein $R^1$ is as defined above;
(j) $R^1$—CH$_2$CH$_2$—PEG-CH$_2$CH$_2$NH$_2$, wherein $R^1$ is as defined above;

(k) (alkyl)O-PEG-OR$^a$ or (cycloalkyl)O-PEG-OR$^a$, wherein R$^a$ is CH$_2$CH(CH$_3$)CN, CH$_2$CH(CH$_3$)CONH$_2$, CH$_2$CH(CH$_3$)CO$_2$H, CH$_2$CH(CH$_3$)CO$_2$(N-succinimidyl), methanesulfonyl, CH$_2$CH$_2$C(CO$_2$Et)$_2$CH$_3$, CH$_2$CH$_2$C(CO$_2$H)$_2$CH$_3$, CH$_2$CH$_2$C(CH$_3$)CO$_2$H, or CH$_2$CH$_2$C(CH$_3$)CO$_2$(N-succinimidyl);

(l) BzO-PEG-R$^b$, wherein R$^b$ is O(methanesulfonyl), OH, NH$_2$, CH$_2$CO$_2$C(Me)$_3$, OCH$_2$CH(OEt)$_2$;

(m) HO-PEG-R$^c$, wherein R$^c$ is NH$_2$, OCH$_2$CO$_2$H, OCH$_2$CO$_2$Me, OCH$_2$CH(OEt)$_2$;

(n) (methanesulfonyl)O-PEG-OCH$_2$CO$_2$Me;

(o) H$_2$N-PEG-OCH$_2$CO$_2$H;

(p) Ph-CH=CH—CH=CH—CO$_2$-PEG-OCH$_2$CH(OEt)$_2$, (q) HO$_2$CCH$_2$CH$_2$CO$_2$-PEG-OCH$_2$CH(OEt)$_2$;

(r) CH$_2$CHC(O)O-PEG-R$^d$, wherein R$^d$ is p-toluenesulfonyl, cyano, glutarate, acryloyl, Si(OEt)$_3$, N-phthalimido, or CH$_2$CO$_2$H;

(s) R$^e$-PEG-R$^e$, wherein each R$^e$ is independently cyano, p-toluenesulfonyl, —CO$_2$H, N-phthalimido, —CH$_2$CH$_2$OAc, or —Si(OET)$_3$;

(t) R$^f$-PEG-Ac, wherein R$^f$ is cyano, p-toluenesulfonyl, N-phthalimido, or HO$_2$C—;

(u) R$^g$-PEG-OH, R$^g$-PEG-O(p-toluenesulfonyl), R$^g$-PEG-CH$_2$CH$_2$NMe$_2$, R$^g$-PEG-O(p-toluenesulfonyl), or R$^g$-PEG-OH, wherein each R$^g$ is phenyl substituted with a vinyl group;

(v) HO-PEG-S—S-pyridin-2-yl;

(w) cyano-CH$_2$CH$_2$-PEG-R$^h$, wherein R$^h$ is OH, O(p-toluenesulfonyl), N-phthalimido, NH$_2$;

(x) HO$_2$CCH$_2$CH$_2$-PEG-OH;

(y) (EtO)$_2$CHCH$_2$CH$_2$-PEG-R$^i$, wherein R$^i$ is methanesulfonyloxy, —SC(S)OEt, SH, or —CH$_2$CH$_2$OC(O)(CH$_3$)=CH$_2$;

(z) 4-(diethoxymethyl)benzyloxy-PEG-R$^j$, wherein R$^j$ is methanesulfonyloxy, —SC(S)OEt, —SS-pyridin-2-yl;

(aa) 4-(aldehydo)benzyloxy-PEG-SS-pyridin-2-yl;

(bb) 4-(aldehydo)benzyloxy-PEG-CH$_2$CH$_2$OC(O)(CH$_3$)=CH$_2$;

(cc) cyano-CH$_2$—PEG-OH, H$_2$N—CH$_2$CH$_2$-PEG-OH;

(dd) HO-PEG-O(allyl), (alkoxy)-PEG-O(allyl), or (cycloalkoxy)-PEG-O(allyl);

(ee) (alkoxy)-PEG-CH$_2$CH$_2$CH$_2$SCH$_2$CH$_2$NH$_2$, (cycloalkoxy)-PEG-CH$_2$CH$_2$CH$_2$SCH$_2$CH$_2$NH$_2$, or HO-PEG-CH$_2$CH$_2$CH$_2$SCH$_2$CH$_2$NH$_2$;

(ff) HO-PEG-N-phthalimido or HO-PEG-NH$_2$;

(gg) H$_2$N-PEG-NH$_2$;

(hh) R$^k$OOC-PEG-CO$_2$R$^k$, wherein each R$^k$ is hydrogen or alkyl; or (ii) PEGOC(O)O(N-succinimidyl).

According to yet another embodiment, for each of the excluded compounds of formula I', as set forth above as groups (f) through (hh), each PEG has between 10 to 2500 ethylene glycol monomers.

Exemplary compounds of formula I' are set forth in Table 6, below wherein each Bn refers to a benzyl group, TBS refers to a t-butyldimethylsilyl group, TBDPSi refers to a t-butyldiphenylsilyl group, BOC refers to a t-butoxycarbonyl group, and each n is as defined herein.

TABLE 6

Representative Compounds of Formula I'
(wherein each n is independently 10-2500)

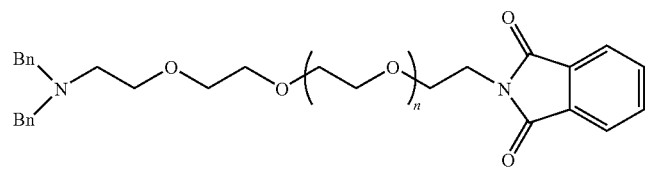

I-1

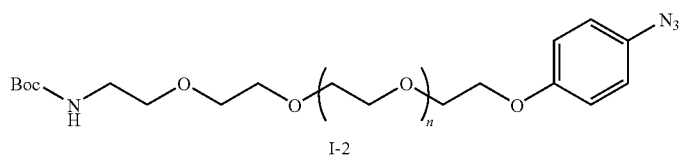

I-2

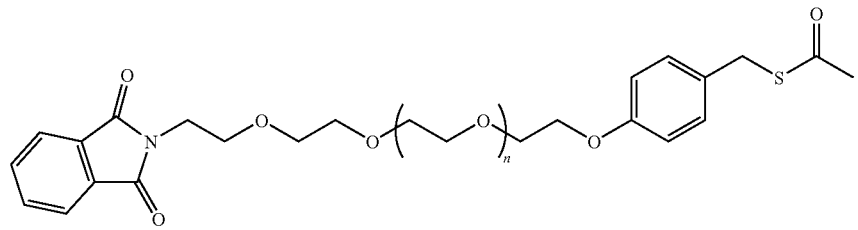

I-3

TABLE 6-continued
Representative Compounds of Formula I'
(wherein each n is independently 10-2500)
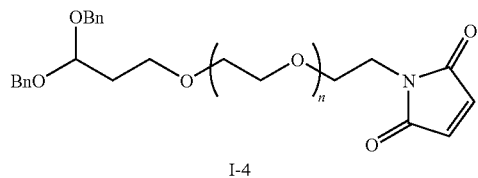
I-4
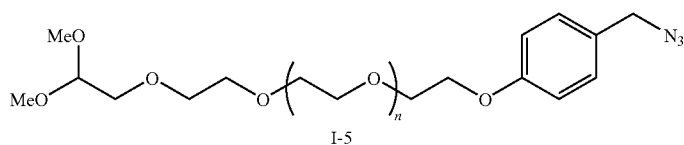
I-5
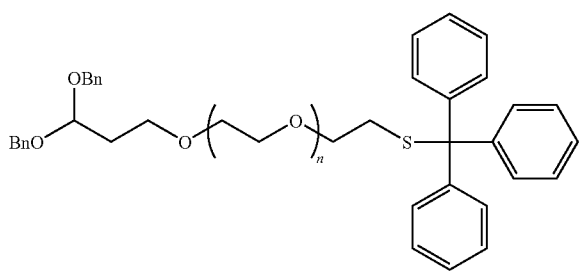
I-6
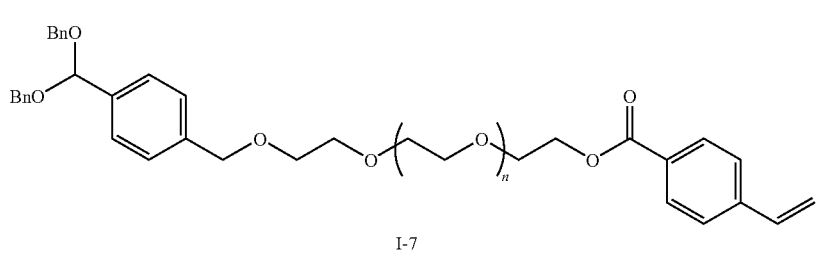
I-7
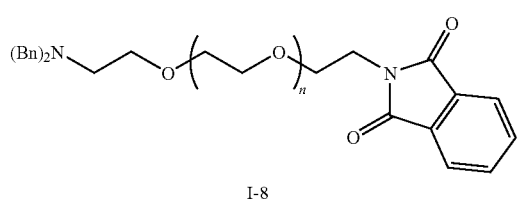
I-8
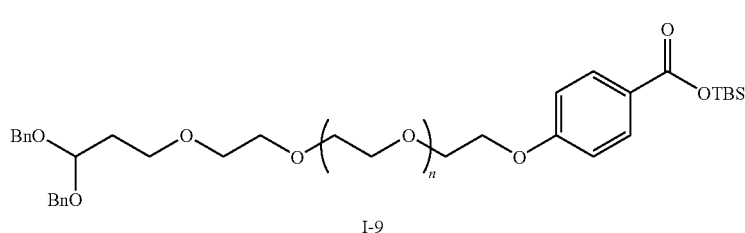
I-9
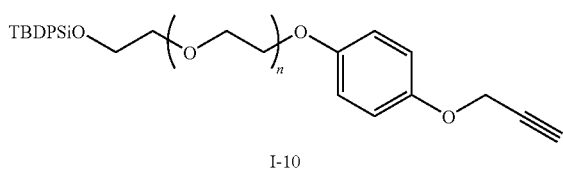
I-10

TABLE 6-continued
Representative Compounds of Formula I'
(wherein each n is independently 10-2500)
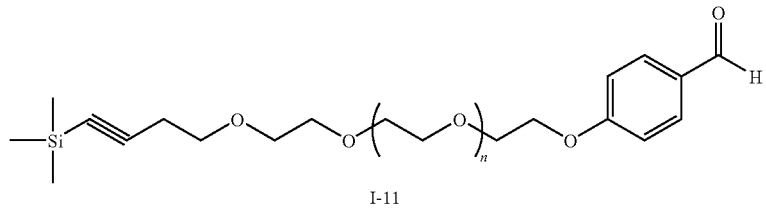
I-11
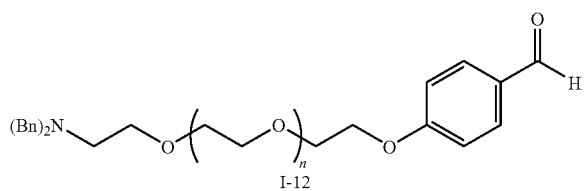
I-12
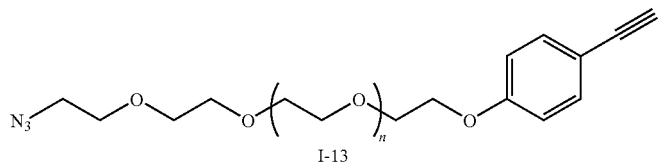
I-13
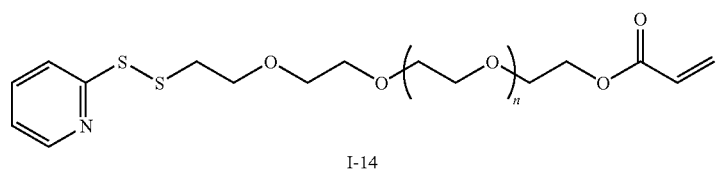
I-14
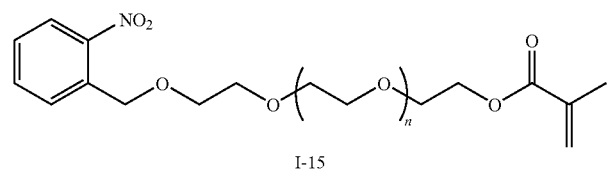
I-15
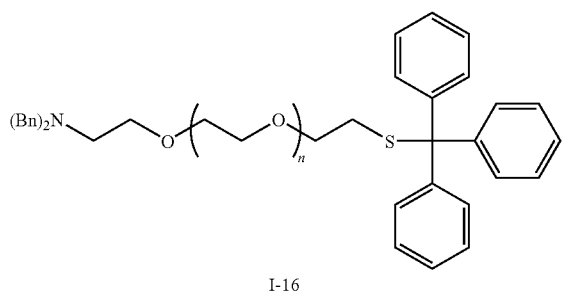
I-16
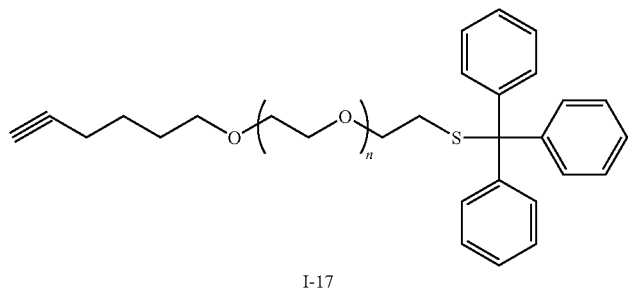
I-17

TABLE 6-continued

Representative Compounds of Formula I'
(wherein each n is independently 10-2500)

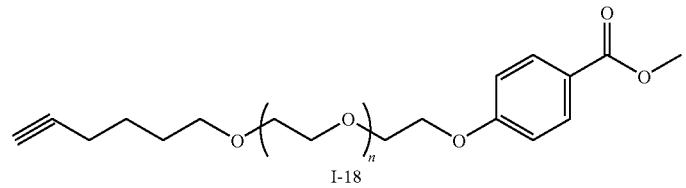

I-18

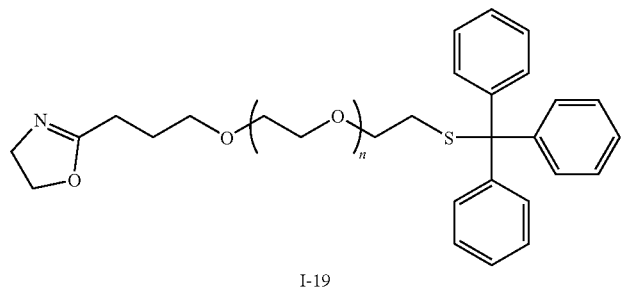

I-19

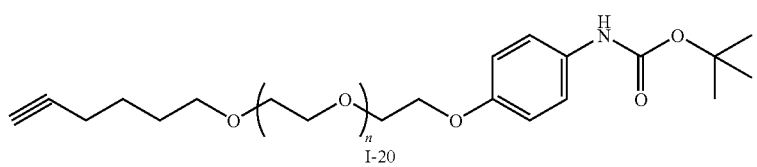

I-20

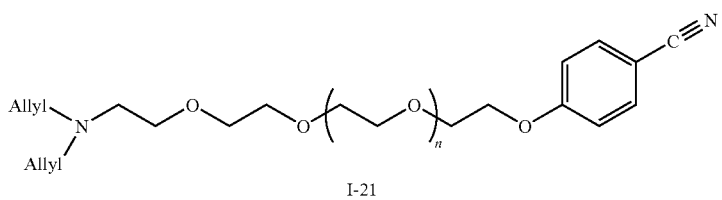

I-21

4. General Methods of Providing the Present Compounds:

The compounds of this invention may be prepared or isolated in general by synthetic methods known to those skilled in the art for analogous compounds and as illustrated by the general schemes and the preparative examples that follow.

Scheme I

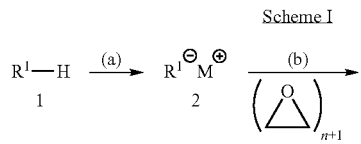

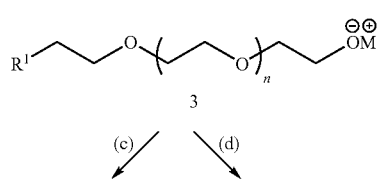

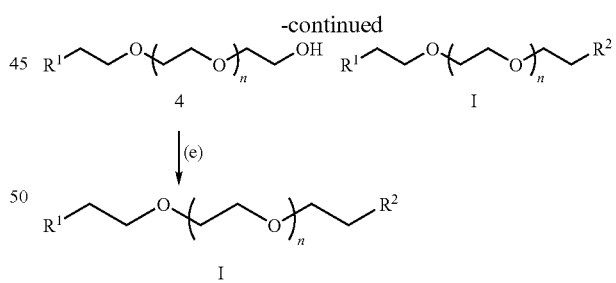

Scheme I above shows a general method for preparing the compounds of the present invention. At step (a), the polymerization initiator is treated with a suitable base to form 2. A variety of bases are suitable for the reaction at step (a). Such bases include, but are not limited to, potassium naphthalenide, diphenylmethyl potassium, triphenylmethyl potassium, and potassium hydride. At step (b), the resulting anion is treated with ethylene oxide to form the polymer 3. Polymer 3 can be transformed at step (d) to a compound of formula I directly by terminating the living polymer chain-end of 3 with a suitable polymerization terminator to afford a compound of formula I. Alternatively, polymer 3 may be quenched at step (c) to form the hydroxyl compound 4. Compound 4 is then derivatized to afford a compound of formula I by methods known in the art, including those described herein.

Although certain exemplary embodiments are depicted and described above and herein, it will be appreciated that compounds of the invention can be prepared according to the methods described generally above using appropriate starting materials by methods generally available to one of ordinary skill in the art. Additional embodiments are exemplified in more detail herein.

One of ordinary skill in the art would recognize that when $R^1$ has a terminal alkyne group, that triple bond is capable of migrating during polymerization. Without wishing to be bound by any particular theory, it is believed that when ethylene oxide is polymerized by an anionic mechanism, the deprotonating base and/or propagating chain end (PEG-O$^-$ M$^+$) can induce triple bond migration resulting in the rearrangement of the terminal acetylene functionality as shown below.

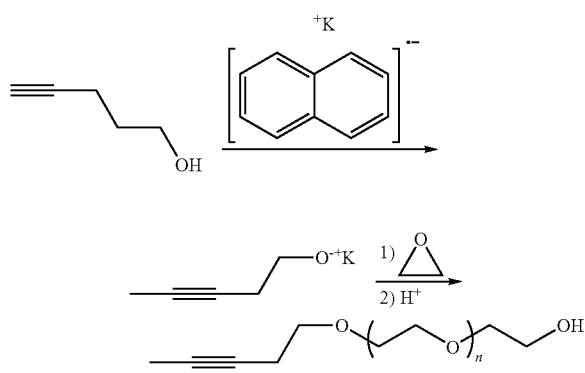

However, one of ordinary skill in the art would also recognize that this process is reversible. In general, strong bases (e.g. NaNH$_2$) can be used to reverse this process, whereby internal alkynes are converted to terminal alkynes by methods substantially similar to those described by Brown, et. al *J. Am. Chem. Soc.*, 1975, 97, 891 and Macaulay, *J. Org. Chem.*, 1980, 45, 734. Without wishing to be bound by theory, it is believed that the conversion of internal alkymes to terminal alkynes is due to the equilibrium shift caused by formation of an acetylid ion. A particularly good base for the internal to terminal alkyne conversion is potassium 3-aminopropylamide or sodium 3-aminopropylamide. This process of migration and conversion is depicted below.

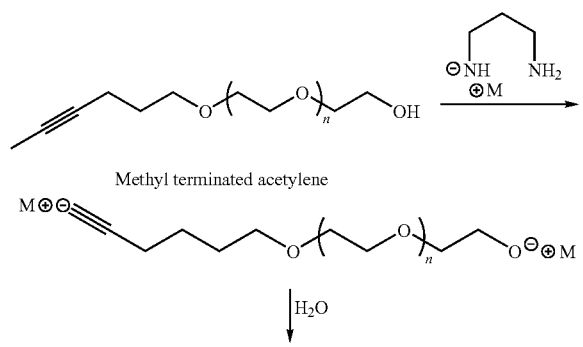

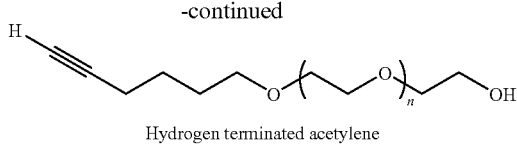

Hydrogen terminated acetylene

5. Uses, Methods, and Compositions

As discussed above, the present invention provides bifunctional PEG's, intermediates thereto, and methods of preparing the same. Such functionalized PEG's are useful for a variety of purposes in the pharmaceutical and biomedical fields. Such uses include using the bifunctional PEG's of the present invention in the process of PEGylating other molecules.

For example, U.S. Pat. No. 6,797,257 describes imaging agents prepared by PEGylating gadolinium oxide albumin microspheres. U.S. Pat. Nos. 6,790,823 and 6,764,853 describe the PEGylation of proteins by covalently bonding through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecule(s).

Accordingly, another aspect of the present invention provides a method of PEGylating a biomolecule with a compound of formula I as described generally above and in classes and subclasses defined above and herein. In certain embodiments, the present invention provides a method of PEGylating a protein, a plasmid, a dye, a peptide, a hydrogel, or a small molecule drug with a compound of formula I as described generally above and in classes and subclasses defined above and herein. According to another aspect, the present invention provides a method for PEGylating a substrate.

The bifunctional PEG's of the present invention are also useful for linking two biomolecules together wherein said biomolecules are the same of different from each other. For example, one terminus of the present compounds may be linked to a surface, other polymer, a protein, a liposome, a cell, a small molecule drug, or a detectable moiety and the other terminus of the present compounds may be linked to a surface, other polymer, a protein, a liposome, a cell, a small molecule drug, or a detectable moiety. Accordingly, the present invention also provides a method for linking two biomolecules together wherein said method comprises coupling one terminus of a compound of formula I to a first biomolecule then coupling the other terminus of a compound of formula I to a second molecule, wherein the first and second biomolecules may be the same or different from each other.

Yet another aspect of the present invention provides a drug-polymer conjugate comprising a compound of formula I and a pharmaceutically active agent. In still another aspect of the present invention, pharmaceutically acceptable compositions are provided, wherein these compositions comprise a drug-polymer conjugate as described herein, and optionally comprise a pharmaceutically acceptable carrier, adjuvant or vehicle. In certain embodiments, these compositions optionally further comprise one or more additional therapeutic agents.

One of ordinary skill in the art would recognize that the present compounds are useful for the PEGylation of small molecule drugs. Small molecule drugs suitable for PEGylation with the present compounds include, but are not limited to, those having a functional group suitable for covalently linking to the bifunctional PEG's of the present invention. Such drugs include, without limitation, chemotherapeutic agents or other anti-proliferative agents including alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), angiogenesis inhibitors (Avastin) and hormones (Tamoxifen, Leuprolide, Flutamide, and Megestrol), Gleevec, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of small molecule drugs that may be PEGylated with the compounds of this invention include treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds and compositions, according to the method of the present invention, may be administered using any amount and any route of administration effective for treating or lessening the severity of the disorder being treated. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

EXAMPLES

As depicted in the Examples below, in certain exemplary embodiments, compounds are prepared according to the following general procedures. It will be appreciated that, although the general methods depict the synthesis of certain compounds of the present invention, the following general methods, in addition to the Schemes set forth above and other methods known to one of ordinary skill in the art, can be applied to all compounds and subclasses and species of each of these compounds, as described herein.

Example 1

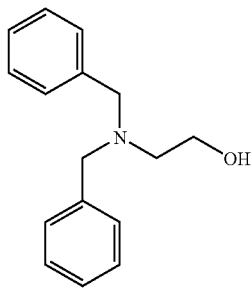

Dibenzylaminoethanol: To a 250 mL round bottom flask equipped with stirbar, reflux condenser, nitrogen inlet, and septum was added potassium carbonate (56.5 g, 0.41 mol), ethanol (80 mL), and ethanolamine (9.9 mL, 0.16 mol). The stirred solution was heated to reflux and benzyl chloride (37.9 mL, 0.33 mol) was added via syringe. The resulting solution was stirred for 16 hours at reflux, allowed to cool, then poured into water (200 mL). The solution was extracted with chloroform (3×300 mL). The combined organic layers were dried with magnesium sulfate, filtered, then evaporated to dryness. Recrystallization from hexanes yielded the product as colorless crystals (32.8 g, 83%). $^1$H NMR (300 MHz, CDCl$_3$) δ 7.33 (10H), 3.60 (4H), 3.58 (2H), 2.67 (2H). $^{13}$C NMR (75 MHz, CDCl$_3$) δ 138.9, 129.2, 128.6, 127.4, 58.7, 58.4, 55.0.

Example 2

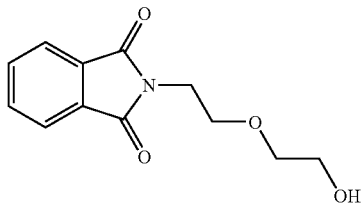

Phthalimide-diethylene glycol: To a 50 mL round bottom flask equipped with stirbar, reflux condenser, nitrogen inlet, and septum was added phthalic anhydride (10 g, 67.5 mmol), aminoethoxyethanol (6.8 mL, 67.5 mmol), and toluene (10 mL). The stirred solution was heated to reflux for 16 hours then cooled to room temperature and concentrated. The residue was dissolved in ethyl acetate and washed with water. The organic fraction was dried with magnesium sulfate, filtered, and concentrated. Recrystallization from hexanes/ethyl acetate yielded the product as white crystals (5.9 g, 37%). $^1$H NMR (300 MHz, CDCl$_3$) δ 7.83 (2H), 7.71 (2H), 3.90 (2H), 3.73 (2H), 3.67 (2H), 3.59 (2H), 2.46 (1H); $^{13}$C NMR (75 MHz, CDCl$_3$) δ 168.42, 133.99, 131.95, 123.29, 72.14, 68.35, 61.69, 37.51.

Example 3

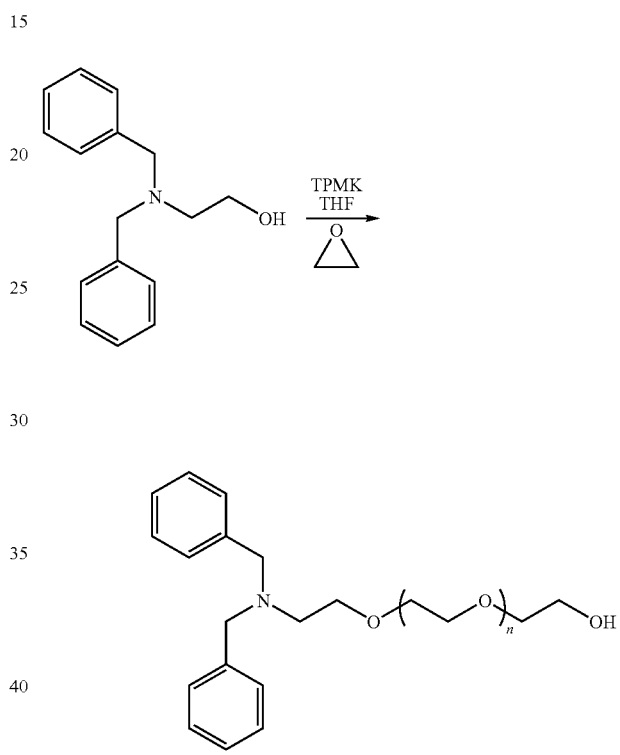

Dibenzylamino-polyethylene glycol-alcohol: To a stirred solution of dibenzylaminoethanol (242 mg, 1 mmol) in anhydrous THF (100 mL) was added a solution of triphenylmethyl potassium in THF (0.5 M, 1.6 mL, 0.8 mmol). The resulting solution was stirred for 5 minutes then cooled to 0° C. Ethylene oxide (10 g, 227 mmol) was introduced to the alkoxide solution using Schlenk techniques. Upon complete addition of the ethylene oxide, the flask was backfilled with Argon, sealed and stirred at room temperature for 24 hours. The reaction was quenched with aqueous HCl (1 M, ca. 1 mL) followed by the removal of solvent under reduced pressure. The resulting viscous liquid was purified by solid phase extraction (the liquid was loaded onto 200 mL silica gel which was rinsed with 3% MeOH in CHCl$_3$ (1 L) followed by 10% MeOH in CHCl$_3$ (1 L) which contained the polymer product) then precipitation into cold diethyl ether to give a white powder (8 g, 80% yield). $^1$H NMR (400 MHz, DMSO-d$_6$, δ) 7.4-7.2 (m, Ar—H), 4.63 (t, CH$_2$OH), 3.7-3.3 (br-m, —O—CH$_2$—CH$_2$—O—). GPC (DMF, PEG standards) M$_n$=10,800; PDI=1.10.

Example 4

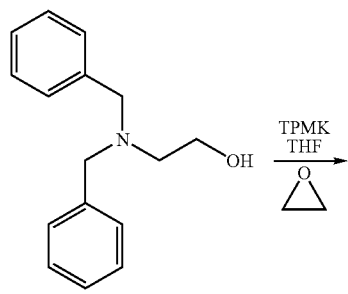

Dibenzylamino-polyethylene glycol-phthalimide: To a stirred solution of dibenzylaminoethanol (242 mg, 1 mmol) in anhydrous THF (100 mL) was added a solution of triphenyl-methyl potassium in THF (0.5 M, 1.6 mL, 0.8 mmol). The resulting solution was stirred for 5 minutes then cooled to 0° C. Ethylene oxide (10 g, 227 mmol) was introduced to the alkoxide solution using Schlenk techniques. Upon complete addition of the ethylene oxide, the flask was backfilled with Argon, sealed and stirred at room temperature for 24 hours. Phthalimide (0.7 g, 5 mmol), triphenylphosphine (1.3 g, 5 mmol) and DIAD (1 g, 5 mmol) was added to the polymerization then stirred an additional 8 hours. The solvent was then removed under reduced pressure and the resulting viscous liquid was purified by solid phase extraction (the liquid was loaded onto 200 mL silica gel which was rinsed with 3% MeOH in CHCl₃ (1 L) followed by 10% MeOH in CHCl₃ (1 L) which contained the polymer product). Pure product was obtained as a white powder following precipitation into cold ether (7.4 g, 73% yield). $^1$H NMR (400 MHz, DMSO-d$_6$, δ) 7.85 (m, phthalimide Ar—H), 7.4-7.2 (m, Ar—H), 3.7-3.3 (br-m, —O—CH$_2$—CH$_2$—O—). GPC (DMF, PEG standards) M$_n$=10,900; PDI=1.11.

Example 5

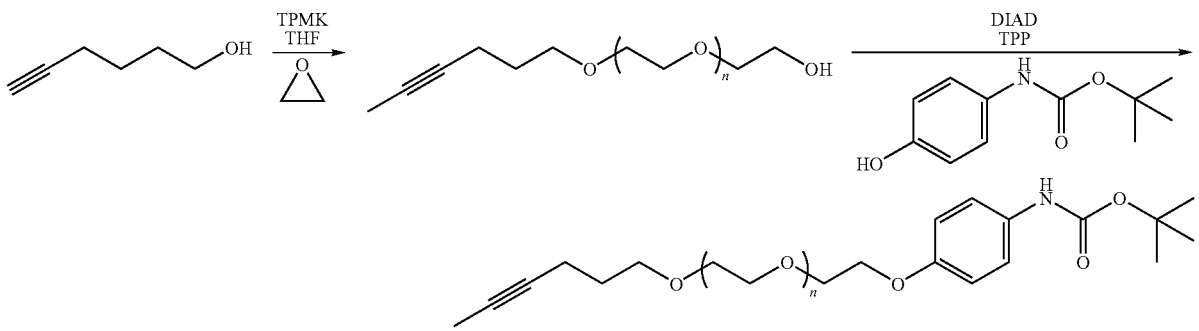

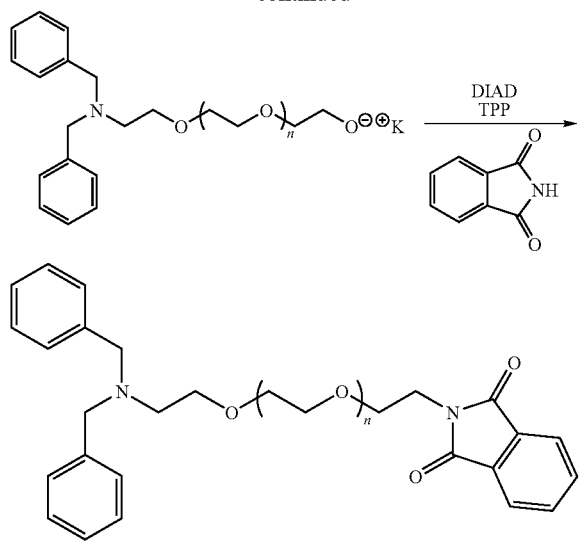

Hexyne-polyethylene glycol-BOC-aminophenoxy ether: To a stirred solution of 5-hexyn-1-ol (98 mg, 1 mmol) in anhydrous THF (100 mL) was added a solution of triphenyl-methyl potassium in THF (0.5 M, 1.6 mL, 0.8 mmol). The resulting solution was stirred for 5 minutes then cooled to 0° C. Ethylene oxide (10 g, 227 mmol) was introduced to the alkoxide solution using Schlenk techniques. Upon complete addition of the ethylene oxide, the flask was backfilled with Argon, sealed and stirred at room temperature for 24 hours. The reaction was quenched with aqueous HCl (1 M, ca. 1 mL), the solvent removed and precipitated into diethyl ether. The solid product was then added to a 100 mL round bottom flask and dissolved in anhydrous THF (40 mL). N-BOC aminophenol (1 g, 5 mmol), triphenylphosphine (1.3 g, 5 mmol) and DIAD (1 g, 5 mmol) was added to the solution then stirred for 8 hours. The solvent was then removed under reduced pressure and the resulting viscous liquid was purified by solid phase extraction (The liquid was loaded onto 200 mL silica gel which was rinsed with 3% MeOH in CHCl₃ (1 L) followed by 10% MeOH in CHCl₃ (1 L) which contained the polymer product). Pure product was obtained as a white powder following precipitation into cold ether (7.1 g, 70% yield). $^1$H NMR (400 MHz, DMSO-d$_6$, δ) 7.85 (m, phthalimide Ar—H), 7.35 (d, Ar—H), 6.85 (d, Ar—H), 3.7-3.3 (br-m, —O—CH$_2$—CH$_2$—O—), 2.14 (m, —CH$_2$), 1.73 (t, CH$_3$), 1.61 (q, —CH$_2$), 1.39 (s, —C—(CH$_3$)$_3$). GPC (DMF, PEG standards) M$_n$=10,800; PDI=1.10.

Example 6

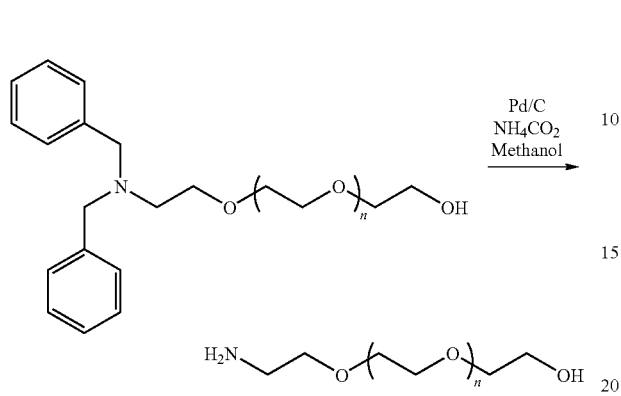

To a 250 mL round bottom flask was added 10% palladium on carbon (300 mg) and methanol (50 mL). Dibenzylamino-polyethylene glycol (10 g) and ammonium formate (2 g) was added and the reaction heated to reflux for 3 hours. The solution was cooled, diluted with chloroform (100 mL) then filtered over basic alumina. The solvent was evaporated and the polymer product precipitated into cold diethyl ether and recovered as a white powder following filtration (8.4 g, 84% yield). $^1$H NMR (400 MHz, DMSO-d$_6$, δ) 3.7-3.3 (br-m, —O—CH$_2$—CH$_2$—O—), 2.62 (m, —CH$_2$—NH$_2$).

Example 7

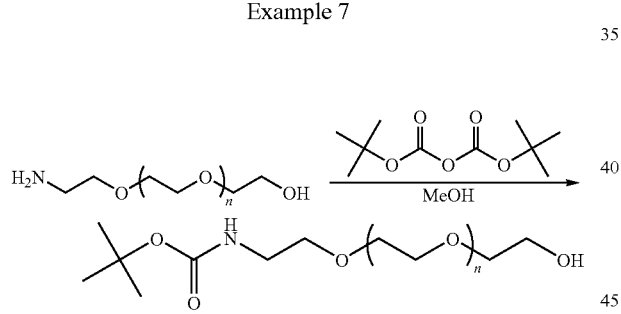

To a 250 mL round bottom flask was added amino-polyethylene glycol-alcohol (10 g) and methanol (150 mL). Di-t-butyldicarbonate (3 g) was added and the resulting solution stirred at room temperature. After 4 hours, the solvent was evaporated at reduced pressure and the polymer was purified by precipitation into cold diethyl ether. Filtration gave the desired product as a white powder (8.9 g, 89% yield). $^1$H NMR (400 MHz, DMSO-d$_6$, δ) 6.82 (br-s, CH$_2$—NH—CO—), 4.63 (t, CH$_2$OH), 3.7-3.3 (br-m, —O—CH$_2$—CH$_2$—O—), 1.40 (s, —C—(CH$_3$)$_3$).

Example 8

It will be appreciated that compounds of the present invention are prepared according to the methods of the invention, the schemes depicted herein, Examples 1-6 above, and by methods known to one of ordinary skill in the art. Exemplary non-limiting compounds that are prepared according to the present invention are set forth below as Examples 8a through 8k. In each of Examples 8a through 8k, "TPMK" refers to triphenylmethyl potassium; "DIAD" refers to diisopropylazodicarboxylate; and "TPP" refers to triphenylphosphine.

Example 8a

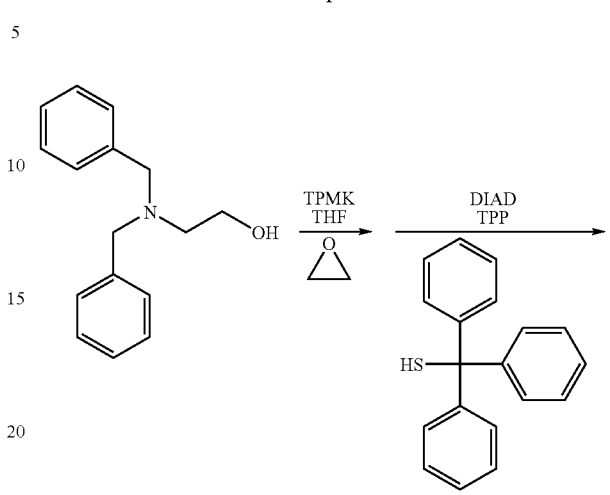

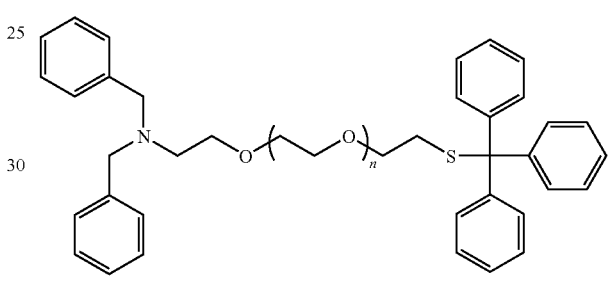

Example 8b

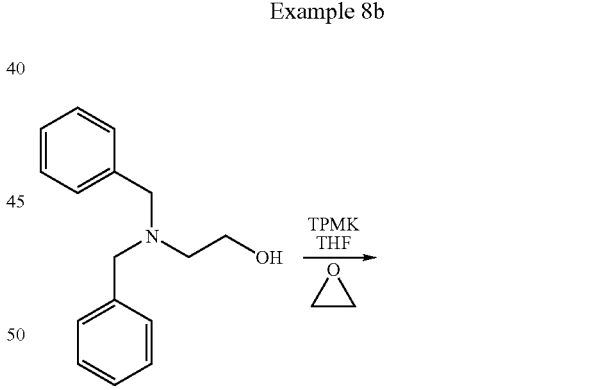

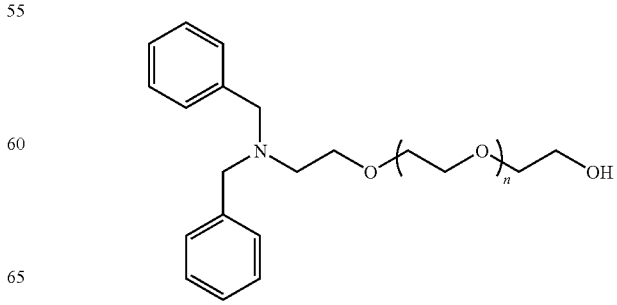

Example 8c
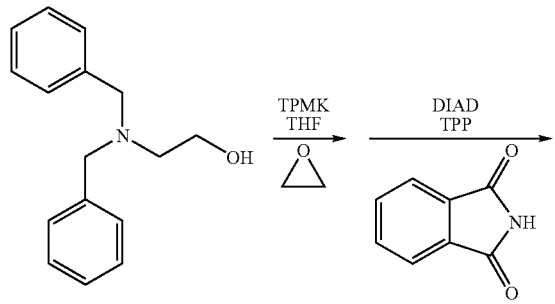
Example 8d
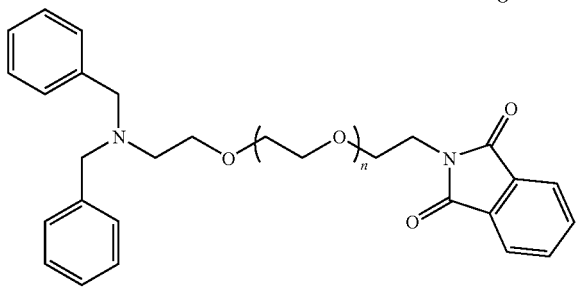
Example 8e
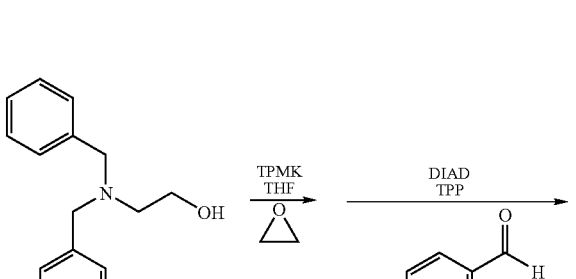
-continued
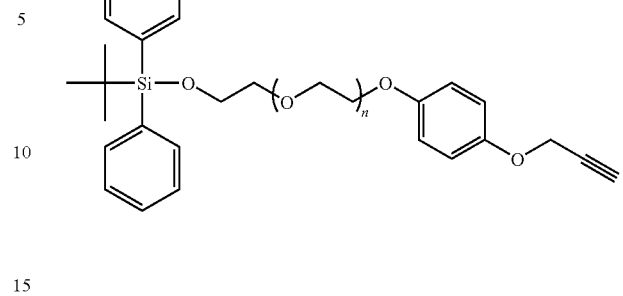
Example 8f
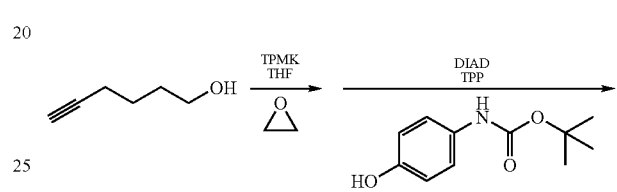
Example 8g
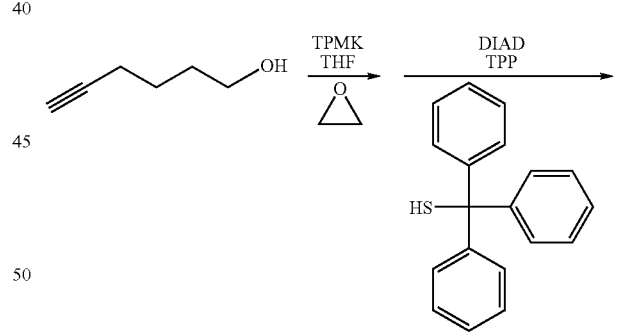
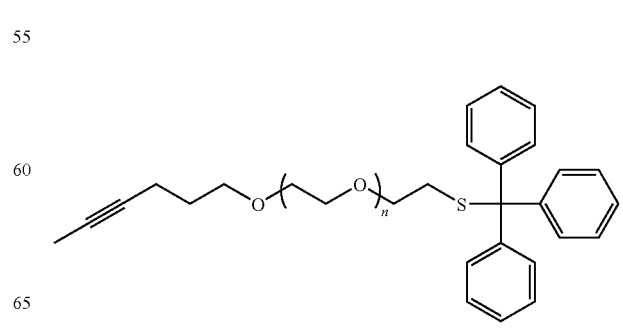

Example 8h

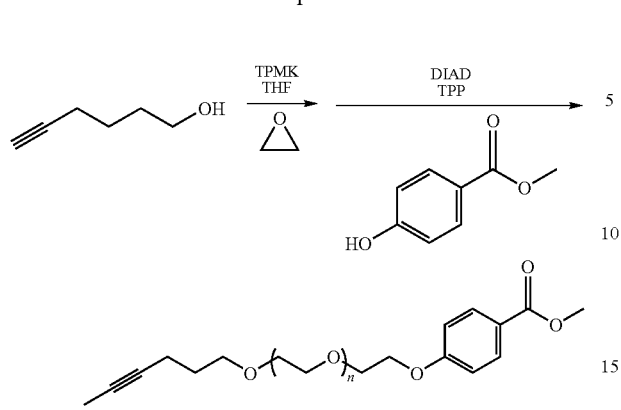

Example 8i

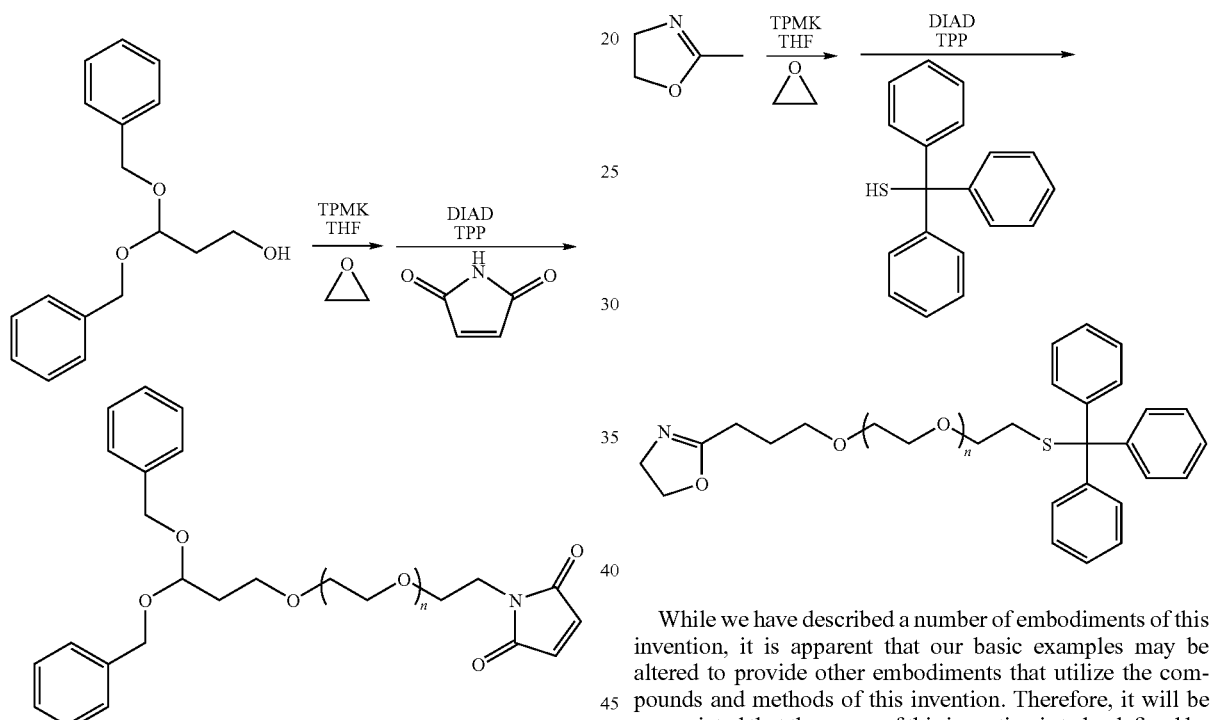

Example 8j

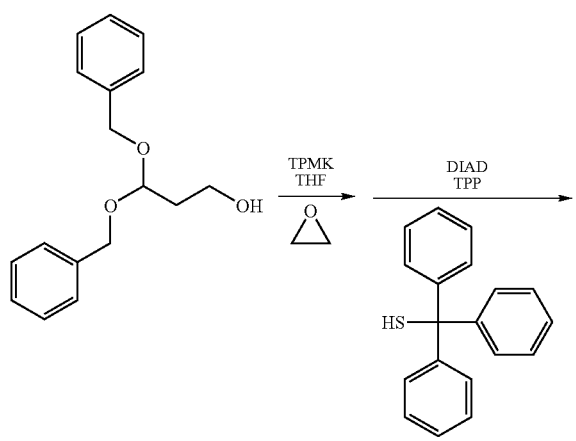

-continued

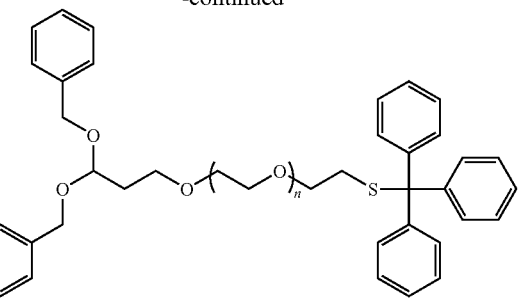

Example 8k

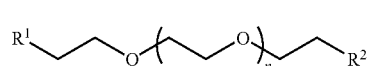

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I':

$$R^1\text{—O}\diagdown(\text{O})_n\diagdown R^2 \qquad I'$$

wherein:
n is 10-2500;
$R^1$ is —X(CH$_2$CH$_2$Y)$_m$(CH$_2$)$_{n'}$R$^3$, wherein:
X is —O—, —S—, —C≡C—, or —CH$_2$—;
each Y is independently —O— or —S—;
m is 0-10;
n_' is 0-10; and
$R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

$R^2$ is halogen, $N_3$, CN, a mono-protected amine, a di-protected amine, a protected hydroxyl, a protected aldehyde, a protected thiol, —$NHR^4$, —$N(R^4)_2$, —$SR^4$, —$O(CH_2CH_2O)_q(CH_2)_rR^5$, —$OC(O)R^4$, or —$OS(O)_2R^4$;

q and r are each independently 0-4;

each $R^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or:

two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur; and $R^5$ is hydrogen, halogen, $N_3$, CN, a mono-protected amine, a di-protected amine, a protected aldehyde, a protected hydroxyl, a protected carboxylic acid, a protected thiol, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, provided that:

(a) when either of $R^1$ or $R^2$ is $(EtO)_2CH$—, then the other of $R^1$ or $R^2$ is not —S—S-pyridin-2-yl, —OBn, —OC(O)C($CH_3$)=$CH_2$, or —OC(O)CH=CH—CH=CH-Ph;

(b) when either of $R^1$ or $R^2$ is —OBn, the other is not —OC(O)Cl;

(c) $R^1$ and $R^2$ are not simultaneously —OC(O)CH=$CH_2$;

(d) when either of $R^1$ or $R^2$ is —CN, then the other is not -phthalimido; and (e) when either of $R^1$ or $R^2$ is acetyl, then the other is not —CN or -phthalimido.

2. The compound according to claim 1, wherein the $R^1$ and $R^2$ groups of formula I' are different from each other.

3. The compound according to claim 1, wherein $R^3$ is an optionally substituted group selected from aliphatic or aryl.

4. The compound according to claim 3, wherein $R^3$ is an aliphatic group substituted with one or more groups independently selected from CN, $N_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, or 2-propargyldisulfanyl.

5. The compound according to claim 3, wherein $R^3$ is an aryl group substituted with one or more groups independently selected from CN, $N_3$, $NO_2$, —$CH_3$, —$CH_2N_3$, —CH=$CH_2$, —C≡CH, Br, I, F, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxymethyl, [1,3]dioxolan-2-yl, or [1,3]dioxan-2-yl.

6. The compound according to claim 2, wherein $R^3$ is a group suitable for Click chemistry.

7. The compound according to claim 6, wherein $R^3$ is an azide-containing group or an alkyne-containing group.

8. The compound according to claim 1, wherein said compound has a polydispersity index of about 1.0 to about 1.2.

9. The compound according to claim 1, wherein n is about 200 to about 250.

10. The compound according to claim 1, wherein n is about 100 to about 150.

11. The compound according to claim 1, wherein n is about 400 to about 500.

12. The compound according to claim 1, wherein said compound is selected from the group consisting of:

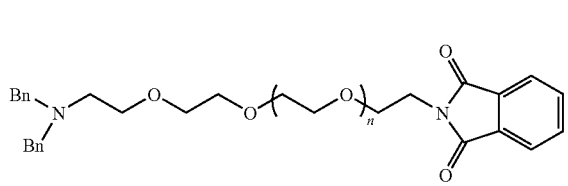

I-1

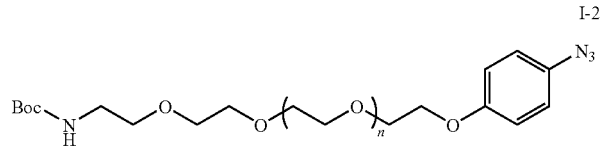

I-2

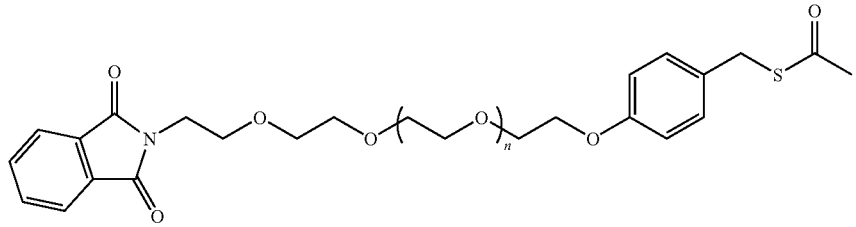

I-3

-continued
I-4
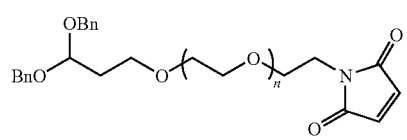
I-5
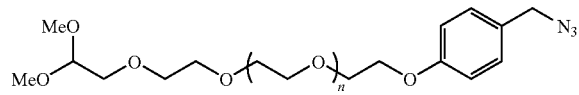
I-6
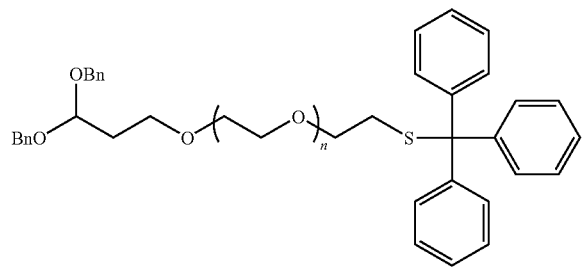
I-7
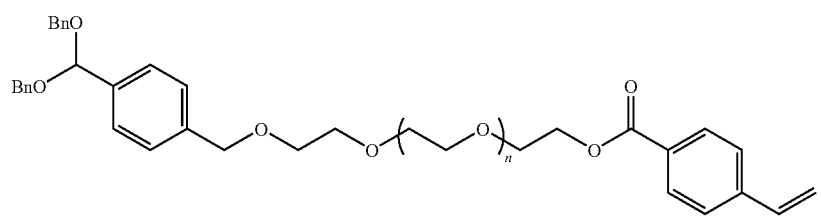
I-8
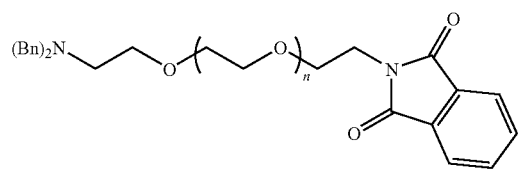
I-9
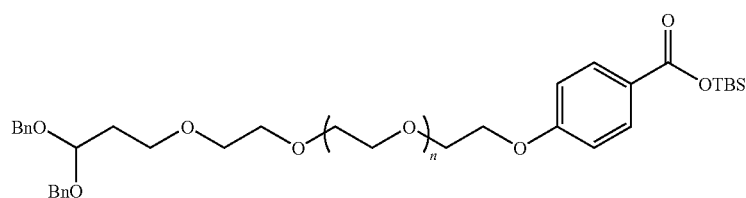
I-10
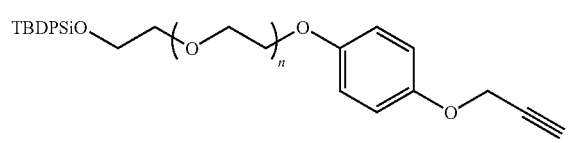
I-11
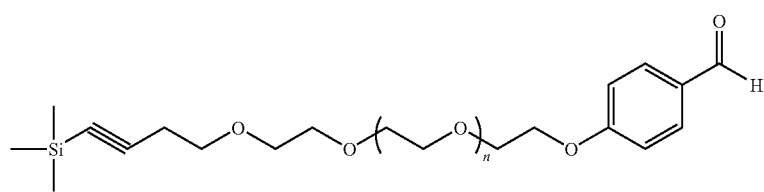
I-12
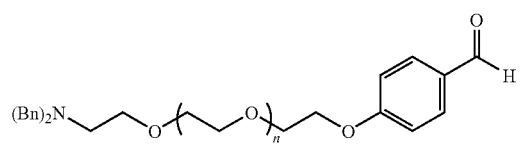
I-13
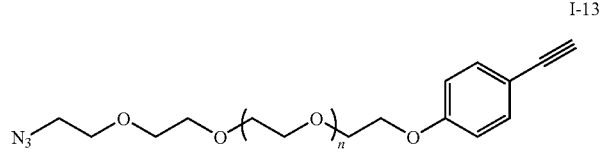

-continued

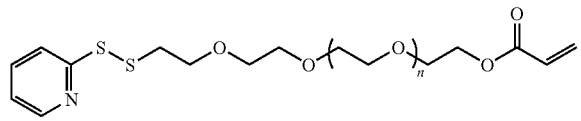
I-14

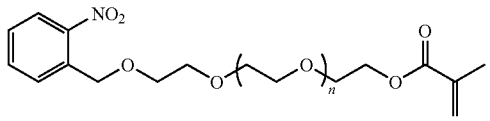
I-15

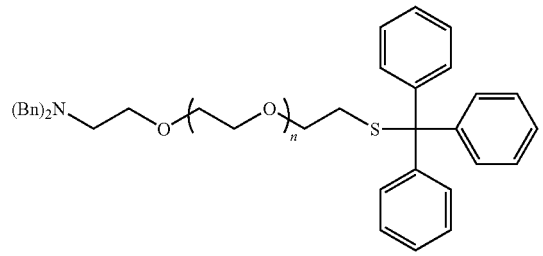
I-16

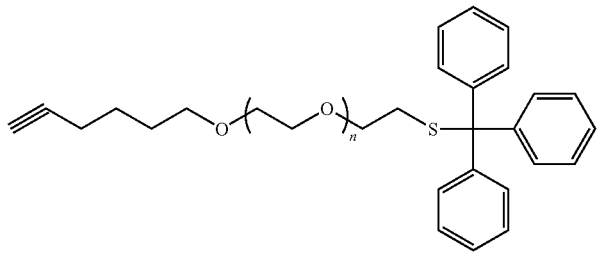
I-17

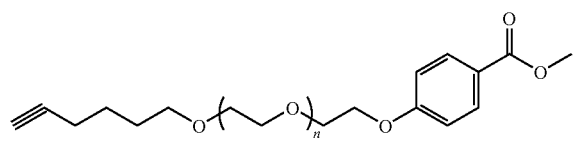
I-18

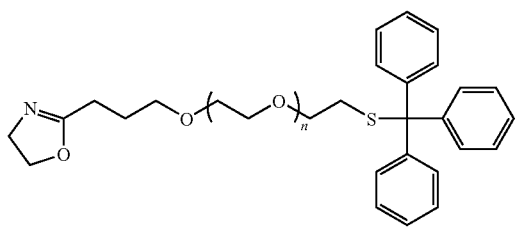
I-19

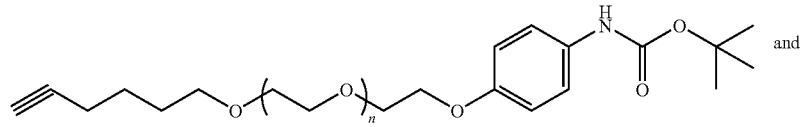
I-20 and

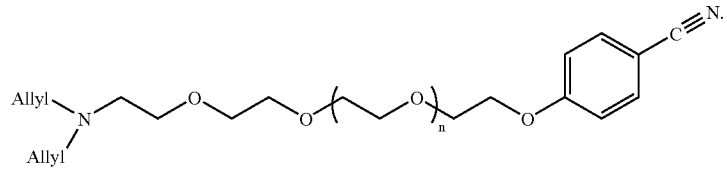
I-21

13. The compound according to claim 1, wherein $R^3$ is a mono-protected or di-protected amino group.

14. The compound according to claim 13, wherein $R^3$ is a mono-protected amino group.

15. The compound according to claim 14, wherein $R^3$ is a mono-protected amino group selected from t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino.

16. The compound according to claim 13, wherein $R^3$ is a di-protected amino group.

17. The compound according to claim 16, wherein $R^3$ is a di-protected amino group selected from di-benzylamine, di-allylamine, phthalimide, maleimide, succinimide, pyrrole, 2,2,5,5-tetramethyl-[1,2,5]azadisilolidine, and azide.

18. The compound according to any one of claims 13-17, wherein $R^2$ is —OS(O)$_2$R$^4$, wherein $R^4$ is an optionally substituted aliphatic group, or an optionally substituted 5-8-membered aryl ring.

19. The compound according to claim 18, wherein $R^2$ is p-toluenesulfonyloxy or methanesulfonyloxy.

20. The compound according to any one of claims 13-17, wherein $R^2$ is a group suitable for Click chemistry.

21. The compound according to claim 20, wherein $R^2$ is —N$_3$.

22. The compound according to claim 1, wherein $R^2$ is selected from the group consisting of:

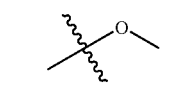
i

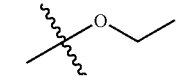
ii

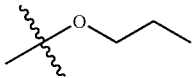
iii

-continued
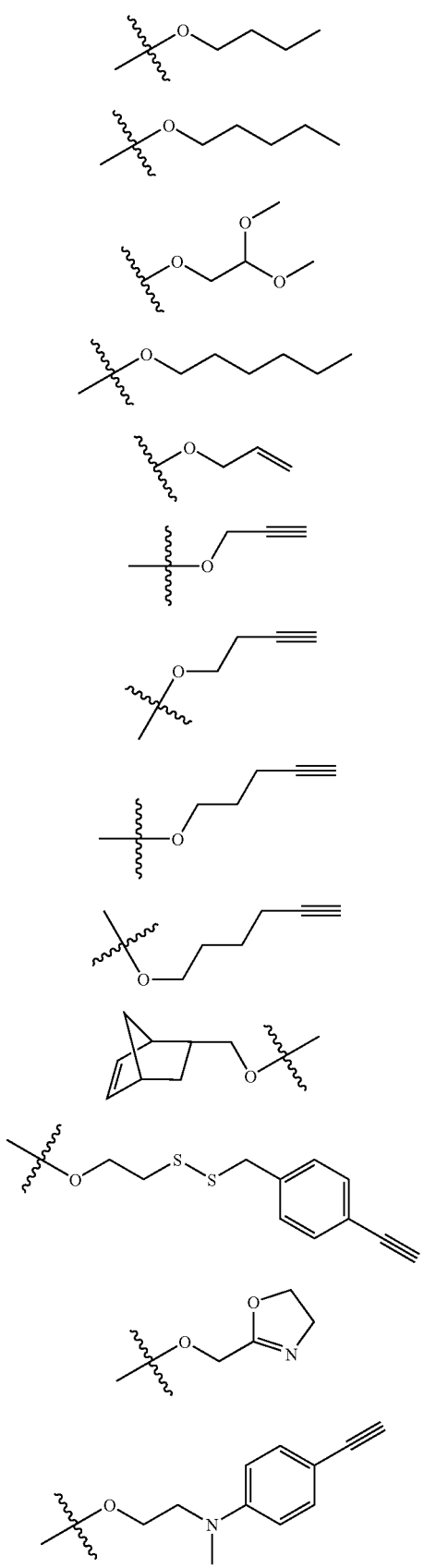
-continued
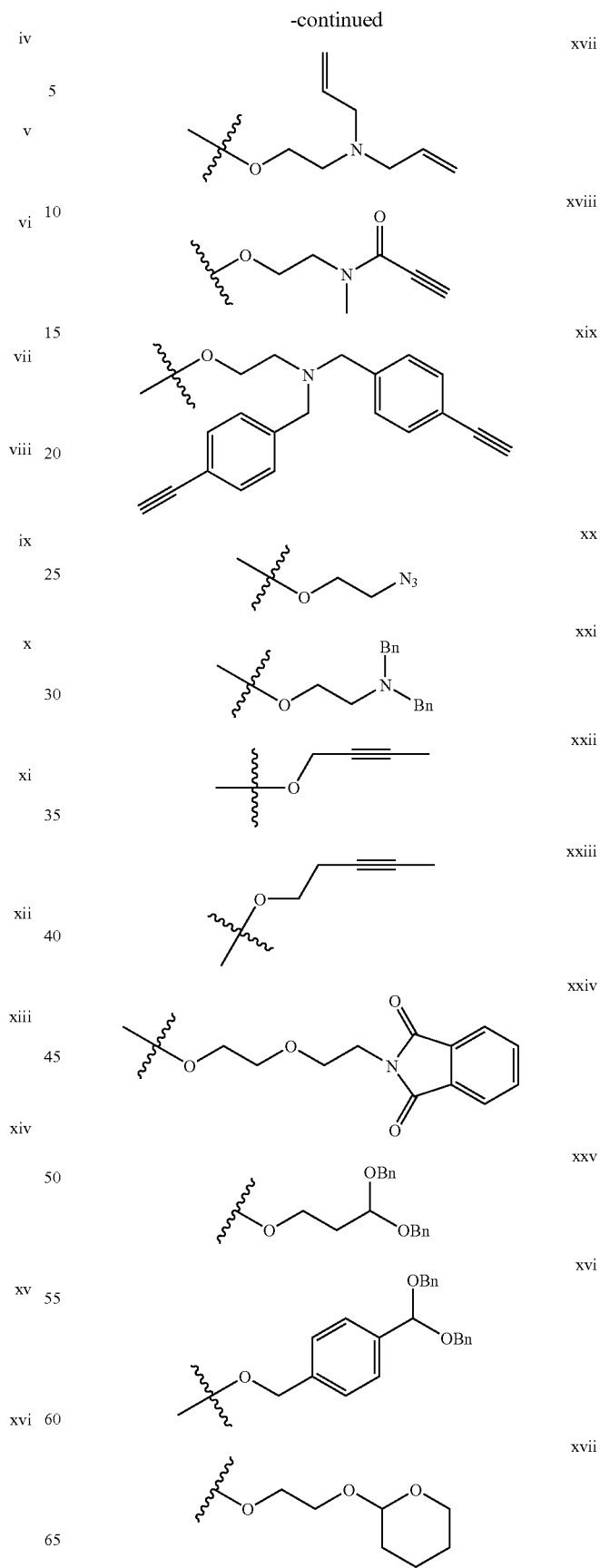

115
-continued
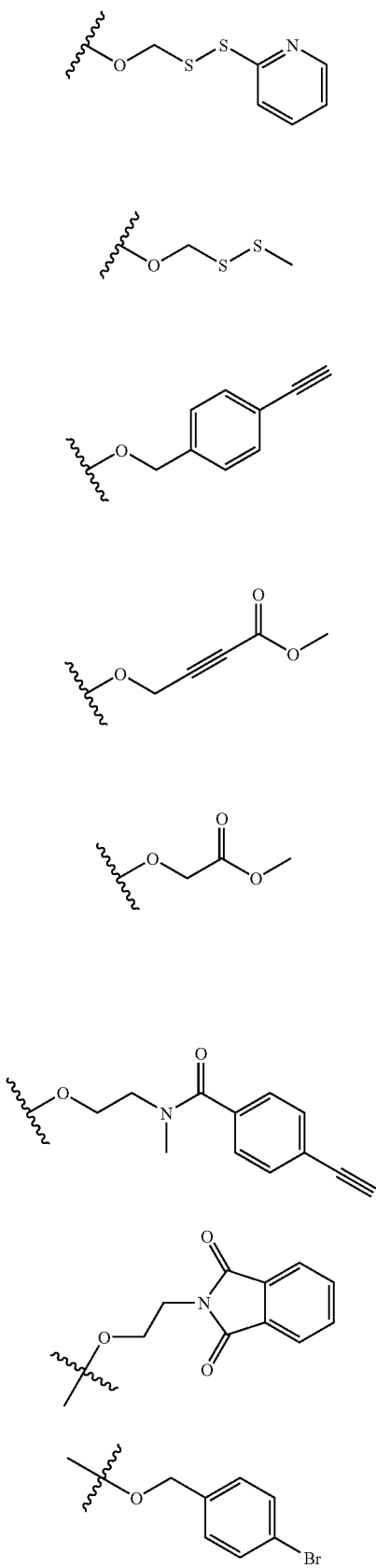
116
-continued
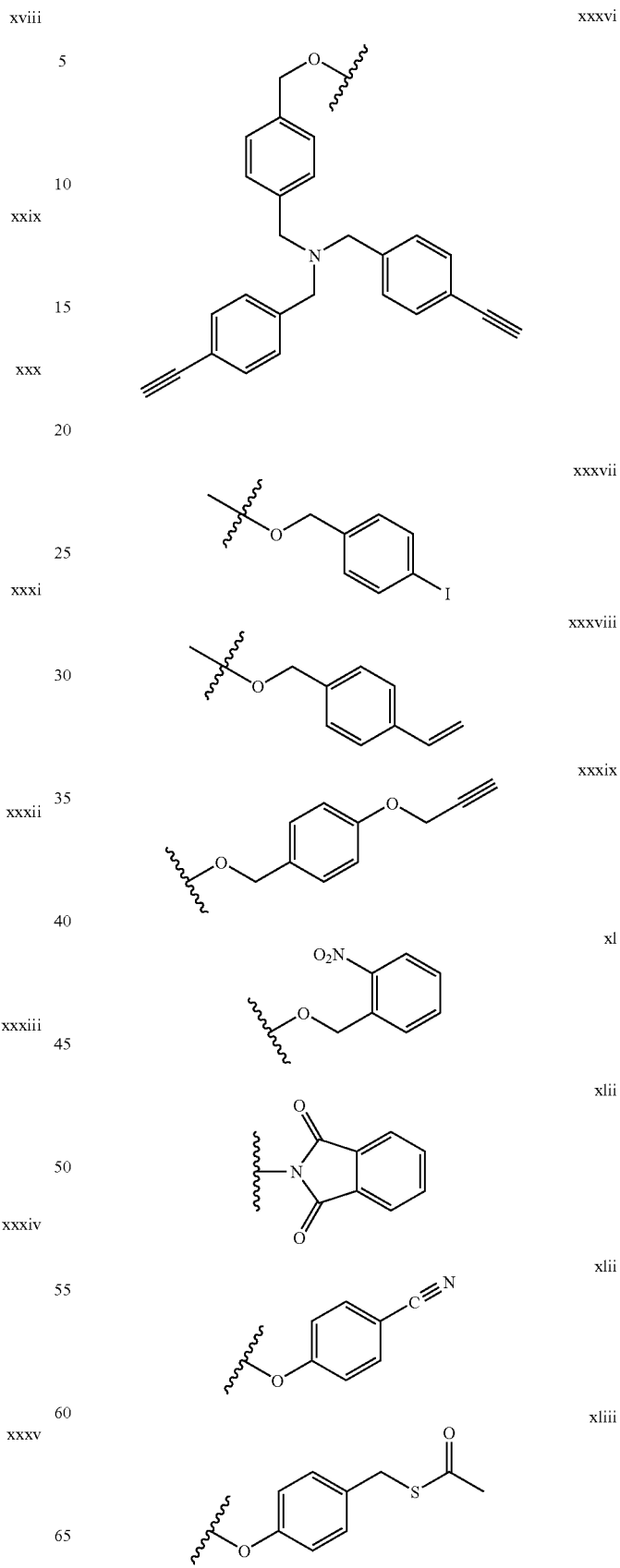

-continued
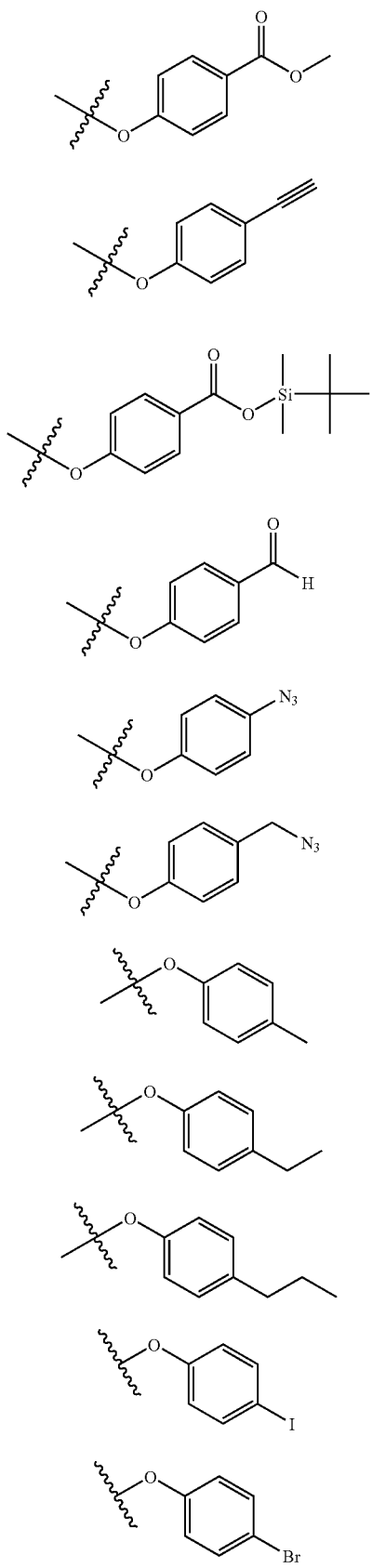
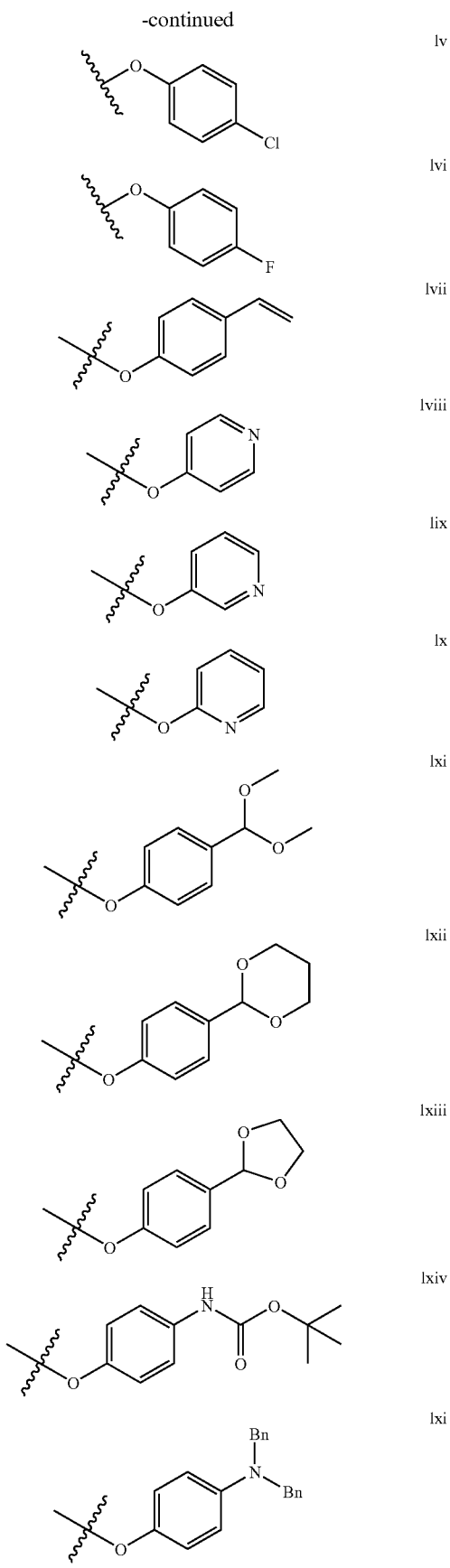

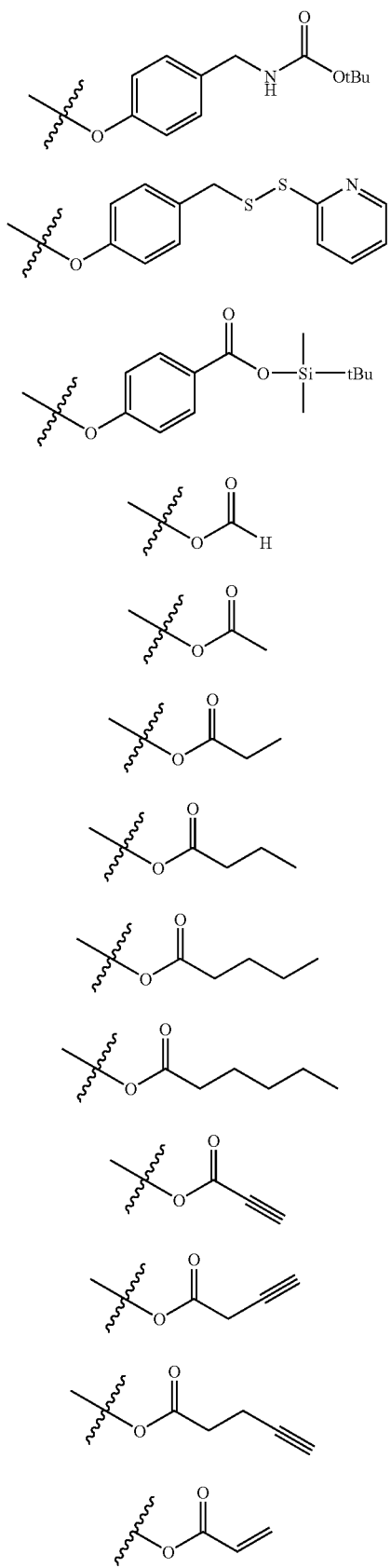
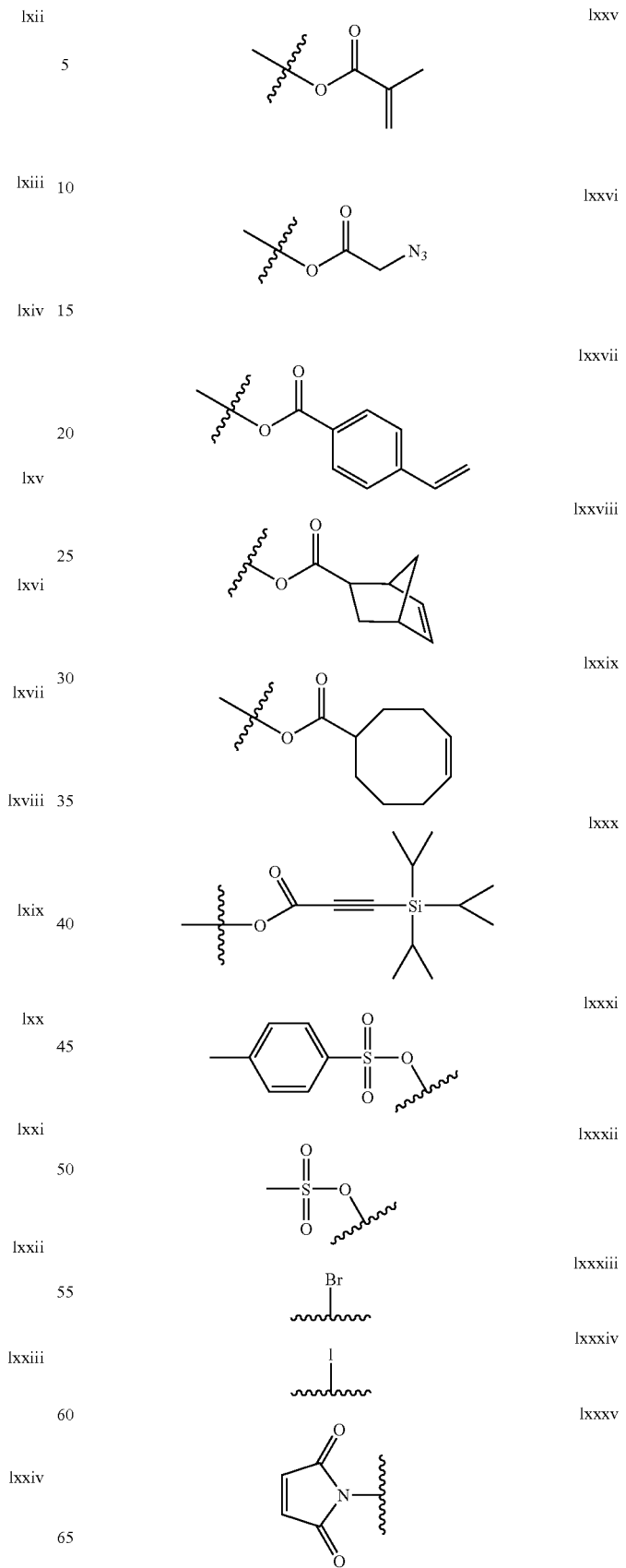

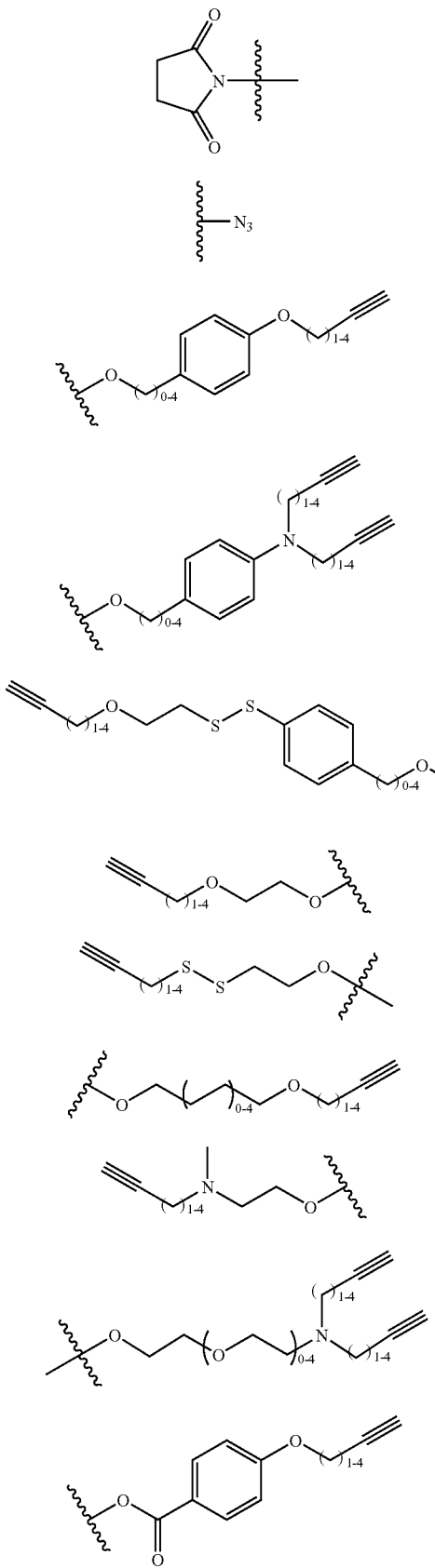
23. The compound according to claim 1, wherein $R^1$ is selected from the group consisting of:
| $R^1$ Groups |
|---|
| a |

-continued
R¹ Groups
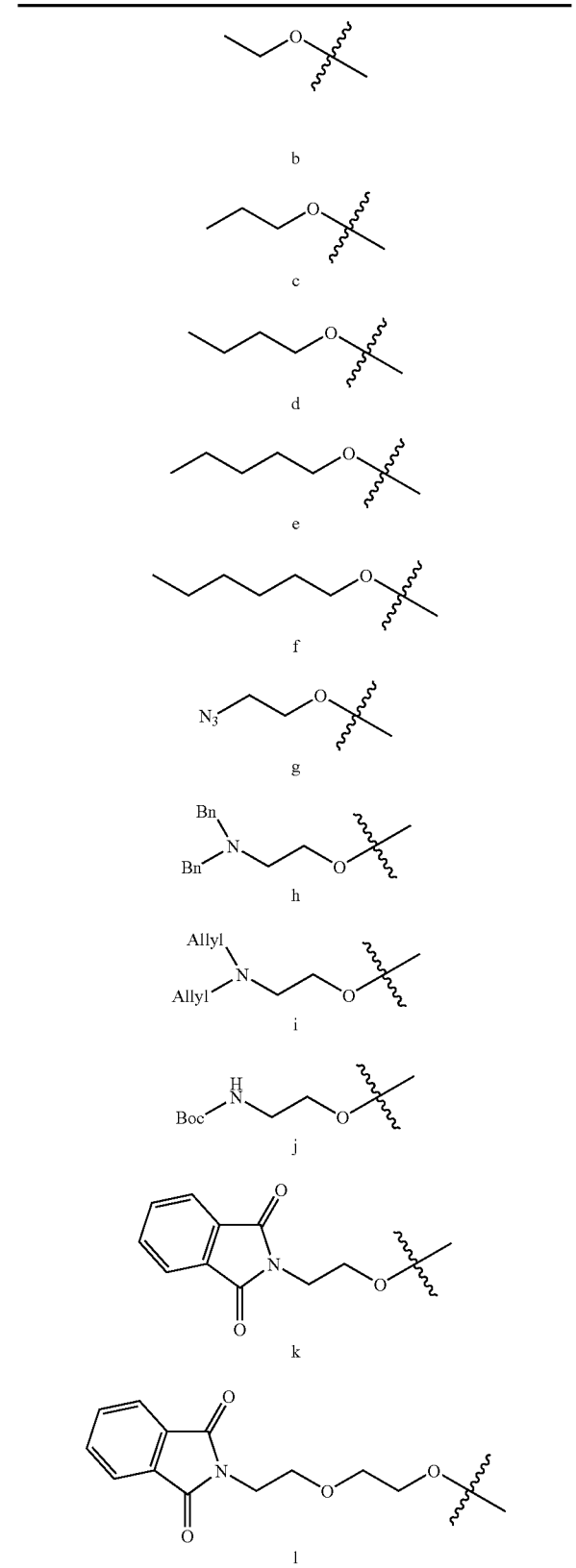
-continued
R¹ Groups
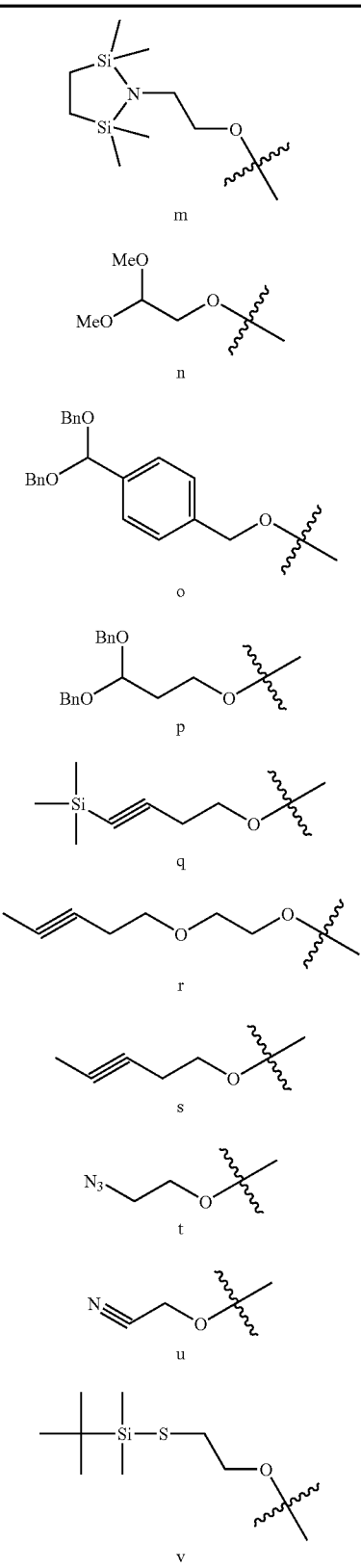

| -continued | -continued |
|---|---|
| R¹ Groups | R¹ Groups |
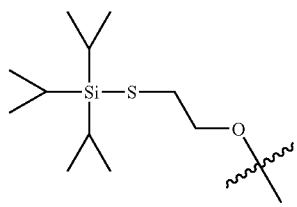
w
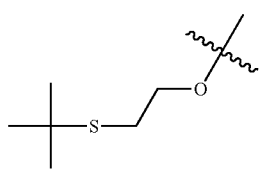
x
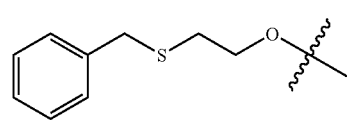
y
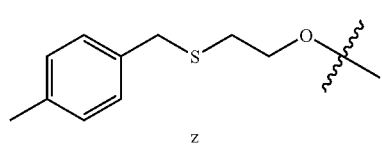
z
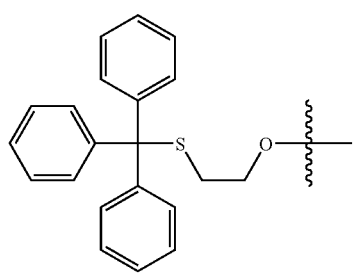
aa
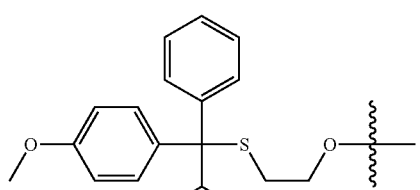
bb
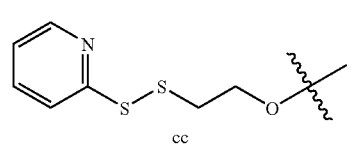
cc
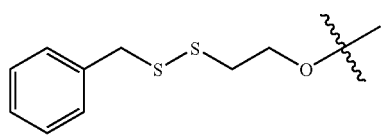
dd
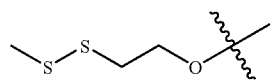
ee
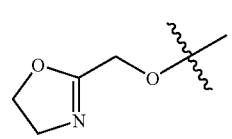
ff
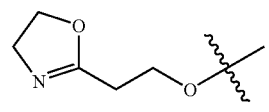
gg
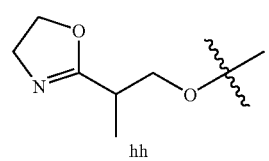
hh
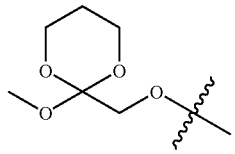
ii
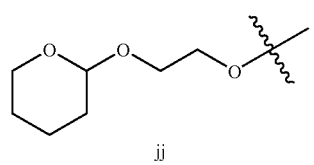
jj
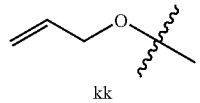
kk
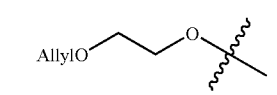
ll
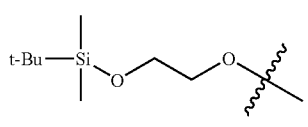
mm -continued R¹ Groups nn, oo, pp, qq, rr, ss, tt, uu, vv, ww, xx, yy, zz, aaa, bbb -continued
R¹ Groups
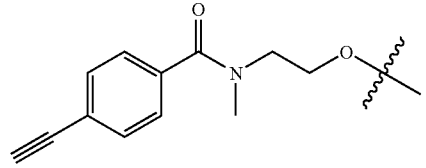
ccc
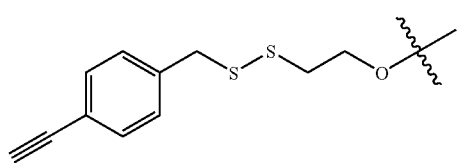
ddd
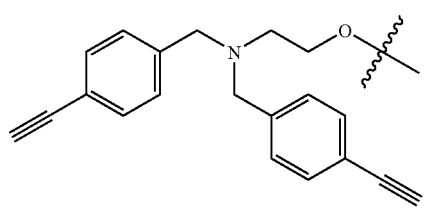
eee
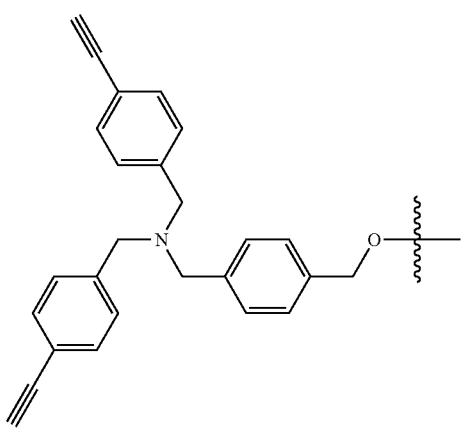
fff
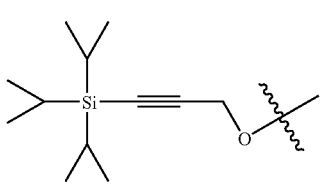
ggg
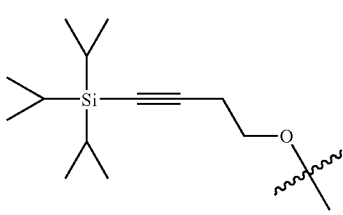
hhh
-continued
R¹ Groups
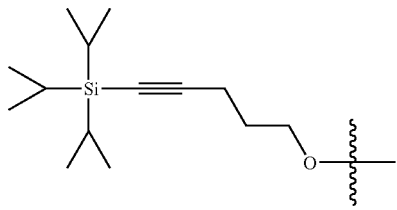
iii
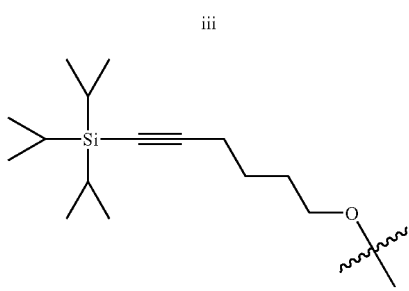
jjj
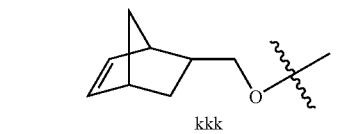
kkk
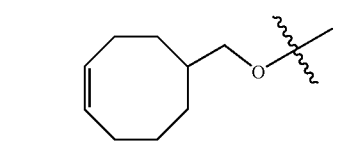
lll
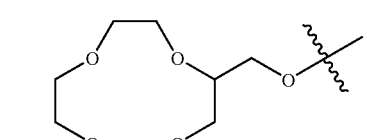
mmm
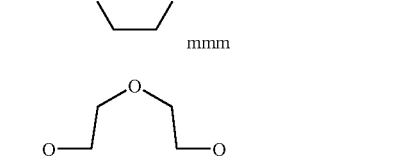
nnn
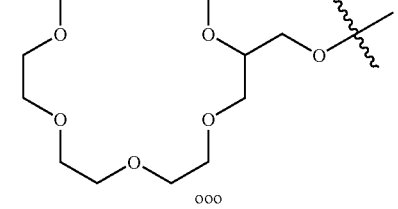
ooo

| R¹ Groups | R¹ Groups |
|---|---|
| 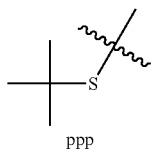<br>ppp | 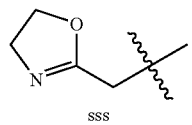<br>sss |
| 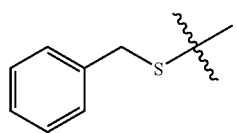<br>qqq | 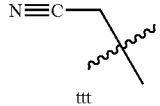<br>ttt |
| 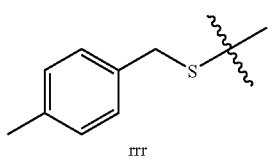<br>rrr | 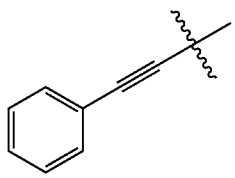<br>and uuu. |
* * * * *

UNITED STATES PATENT AND TRADEMARK OFFICE
CERTIFICATE OF CORRECTION

PATENT NO.       : 7,612,153 B2                                          Page 1 of 1
APPLICATION NO.  : 11/256735
DATED            : November 3, 2009
INVENTOR(S)      : Breitenkamp et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 696 days.

Signed and Sealed this

Nineteenth Day of October, 2010

David J. Kappos
*Director of the United States Patent and Trademark Office*